US008771741B2

(12) United States Patent
Adair et al.

(10) Patent No.: US 8,771,741 B2
(45) Date of Patent: Jul. 8, 2014

(54) IN VIVO PHOTODYNAMIC THERAPY OF CANCER VIA A NEAR INFRARED AGENT ENCAPSULATED IN CALCIUM PHOSPHATE NANOPARTICLES

(75) Inventors: James H. Adair, State College, PA (US); Mark Kester, Harrisburg, PA (US); Peter C. Eklund, Boalsburg, PA (US); Karen L. Eklund, legal representative, Boalsburg, PA (US); Erhan I. Altinoglu, State College, PA (US); Brian M. Barth, Hummelstown, PA (US); Timothy J. Russin, San Diego, CA (US); James M. D. Kaiser, Harrisburg, PA (US); Thomas T. Morgan, Pepperell, MA (US)

(73) Assignee: The Penn State Research Foundation, University Park, PA (US)

( * ) Notice: Subject to any disclaimer, the term of this patent is extended or adjusted under 35 U.S.C. 154(b) by 628 days.

(21) Appl. No.: 12/657,556

(22) Filed: Jan. 22, 2010

(65) Prior Publication Data

US 2010/0247436 A1    Sep. 30, 2010

Related U.S. Application Data

(60) Provisional application No. 61/147,003, filed on Jan. 23, 2009.

(51) Int. Cl.
*A61K 9/14*    (2006.01)
(52) U.S. Cl.
USPC .......................................................... 424/489
(58) Field of Classification Search
None
See application file for complete search history.

(56) References Cited

U.S. PATENT DOCUMENTS

| 5,556,992 A * | 9/1996 | Gaboury et al. ............... 549/227 |
| 2003/0167033 A1* | 9/2003 | Chen et al. ...................... 604/20 |
| 2007/0218049 A1 | 9/2007 | Chen et al. | |

OTHER PUBLICATIONS

Altinoglu et al., "Near-Infrared Emitting Fluorophore-Doped Calcium Phosphate Nanoparticles for In Vivo Imaging of Human Breast Cancer", Nano Letters 2(10):2075-2084 (2008).
Gil et al., "Composite Nanoparticles Take Aim at Cancer", Nano Letters 2(11):2200-2205 (2008).
Kester et al., "Calcium Phosphate Nanocomposite Particles for In Vitro Imaging and Encapsulated Chemotherapeutic Drug Delivery to Cancer Cells", Nano Letters 8(12):4116-4121 (2008).
Morgan et al., "Encapsulation of Organic Molecules in Calcium Phosphate Nanocomposite Particles for Intracellular Imaging and Drug Delivery", Nano Letters 8(12):4108-4115 (2008).
Rao, "Shedding Light on Tumors Using Nanoparticles", 2(10):1984-1986 (2008).
Gao et al., "Nanoparticles for two-photon photodynamic therapy in living cells", Nano Letters, 6(11):2383-2386 (2006).

(Continued)

*Primary Examiner* — Paul Dickinson
(74) *Attorney, Agent, or Firm* — McKee, Voorhees & Sease, P.L.C.

(57) ABSTRACT

Nano-encapsulated photosensitizers and their use in the treatment of tumors and/or imaging is described. Preferably, the photosensitizers are encapsulated in a calcium phosphate nanoparticle (CPNP). Encapsulating the PS in a CPNP increases the half-life of the PS, increases absorption of the PS into the target cell tissue, increases the photostability of the PS, increases the photoefficiency of the PS, increases in vivo retention of the PS, or combinations thereof, ultimately making it a highly efficacious agent for use in photodynamic therapy, imaging target tissues, vessels, or tumors, and/or detecting or locating tumors.

26 Claims, 20 Drawing Sheets
(20 of 20 Drawing Sheet(s) Filed in Color)

(56) References Cited

OTHER PUBLICATIONS

Kester et al., "Supporting Information—Calcium Phosphate Nanocomposite Particles for In Vitro Imaging and Encapsulated Chemotherapeutic Drug Delivery to Cancer Cells", XP002581648 (Oct. 30, 2008), retrieved from the Internet: URF:http://pubs.acs.org/doi/suppl/10.1021/nl802098g/suppl_file/nl802098g_si_001.pdf.

Klesing et al., "Positively charged calcium phosphate/polymer nanoparticles for photodynamic therapy", J. of Materials Science. Materials in Medicine 21:(3):887-892 (2009).

Morgan et al., "Supporting Information—Encapsulation of Organic Molecules in Calcium Phosphate Nanocomposite Particles for Intracellular Imaging and Drug Delivery", XP002581649 (Oct. 30, 2008), retrieved from the Internet: URL: http://pubs.acs.org/doi/suppl/10.1021/nl8019888/suppl_file/nl8019888_si_001.pdf.

Muddana et al., "Photophysics of Cy3-encapsulated calcium phosphate nanoparticles", Nano Letters, 9 (4):1559-1566 (2009).

Muddana et al., "Supporting Information—Photophysics of Cy3-encapsulated calcium phosphate nanoparticles", XP002581650 (Mar. 4, 2009), retrieved from the Internet: URL:http://pubs.acs.org/doi/suppl/10.1021/nl803658w/suppl_file/nl803658w_si_001.pdf.

Saxena et al., "Enhanced photo-stability, thermal-stability and aqueous-stability of indocynine green in polymeric nanoparticulate systems", J. of Photochemistry and Photobiology B: Biology, Elsevier Science S.A., Basel, CH LNKD, 74(1):29-38 (2004).

Schwiertz et al., "Calcium phosphate nanoparticles as efficient carriers for photodynamic therapy against cells and bacteria", Biomaterials, 30(19):3324-3331 (2009).

Search Report for co-pending PCT/US2010/021812 listing relevant art cited by the International Searching Authority.

\* cited by examiner

IN VIVO PHOTODYNAMIC THERAPY OF CANCER VIA A NEAR INFRARED AGENT ENCAPSULATED IN CALCIUM PHOSPHATE NANOPARTICLES

CROSS-REFERENCE TO RELATED APPLICATIONS

This application claims priority under 35 U.S.C. §119 of a provisional application Ser. No. 61/147,003 filed Jan. 23, 2009, which application is hereby incorporated by reference in its entirety.

GRANTS

This invention was made with government support under Grant No. DGE-0338240 awarded by National Science Foundation, Grant HL-074311 to VR-V awarded by the National Institutes of Health. The government has certain rights in the invention.

BACKGROUND OF THE INVENTION

Pancreatic, lung cancer, ovarian cancer, brain cancer, and ovarian cancer remain some of the most difficult cancers to treat. As an example, pancreatic cancer is the fourth leading cause of cancer related deaths (ACS). In 2008 an estimated 37,680 people will be diagnosed with pancreatic cancer and 34,290 will die from the disease (ACS). The high rate of mortality for pancreatic cancer is mainly attributed to the tendency for late diagnoses as symptoms may not occur until the disease has metastasized as well as the lack of effective systemic therapies. This leaves surgery as an option in only 10-20% of pancreatic cancer patients and chemotherapy and radiation as the main therapeutic measures. Of those who are surgical candidates, less than 40% of the surgeries are curative, with most experiencing either recurrent pancreatic tumors or tumors that have metastasized to the liver. Both radiation and chemotherapy treatment options result in severe side effects that affect the patient's quality of life and many times fail to provide significant improvement in the disease. The standard chemotherapy treatment for advanced pancreatic cancer, gemcitabine, most commonly causes side effects of nausea, pain, fatigue, increased susceptibility to infection, renal toxicity and liver toxicity. The effectiveness of gemcitabine can also be limited by drug efflux mechanisms in tumor cells resulting in incomplete tumor responses. Although many clinical trials have been undertaken, gemicitabine has remained the standard of treatment for pancreatic cancer for the past decade. There is a clear need for improved therapies that have better efficacy and reduced side effects in the treatment of pancreatic cancer and other difficult to treat cancers.

The reaction achieved with Photodynamic Therapy (PDT) combines three individually non-toxic components, the photosensitizer, light and tissue oxygen to selectively destroy tissue. For tumor types other than skin cancer, PDT treatment involves an intravenous injection of photosensitizer, which is allowed to circulate within the body for a period of time to accumulate within the tumor site. This is followed by irradiation of the tumor site with light, most conveniently a laser, at the wavelength corresponding to the excitation maxima of the photosensitizer that was used. The light excites the photosensitizer to interact with tissue oxygen creating singlet oxygen species. The singlet oxygen species can then damage tumor cells directly, or via conversion to other reactive oxygen species, not limited to superoxide, hydroxyl radicals, peroxynitrates, hydrogen peroxide, and lipid peroxides. In this way, the localization of photosensitizer to tumor tissue, tissue oxygenation and dose of light are all critical factors in the outcome of PDT. Although PDT is currently approved for the treatment of esophageal cancer, lung cancer and skin cancers in the U.S. it is still limited in use due to short lifetimes of photosensitizers, an inability to penetrate sufficient light through tissue, and an inability to preferentially target cancerous tissues with photosensitizers (Allison, R. R., Bagnato, V. S., Cuenca, R., Downie, G. H., and Sibata, C. H. (2006) The future of photodynamic therapy in oncology. *Future Oncol.* 2: 53-71.).

Although several clinical trials are underway, Photofrin is the only FDA-approved photosensitizer for PDT cancer treatment. While Photofrin provides several advantages for the treatment of esophageal cancer, lung cancer and Barrett's esophagus, it still suffers from a short half-life and a lack of effective tumor localization. This results in suboptimal efficacy as well as systemic photosensitivity side effects. The development of the "second generation" photosensitizers which are now in clinical trials has focused on compounds with decreased photosensitivity reactions. However, these "second generation" photosensitizers as well as Photofrin, have maximum excitations at wavelengths less than 700 nm. This limits the tissue depth that current photosensitizers can be effectively used at since lower wavelengths have limited tissue penetration due to absorption by endogenous chromophores. For these and other reasons, there is a need for the present invention.

BRIEF SUMMARY OF THE INVENTION

The present invention provides methods and composition for the treatment of tumors and/or imaging of target tissue, vessels, or tumors. In one aspect, the method includes administering an effective amount of a nanoencapsulated near-infrared (>500 nm) photosensitizer (PS). Preferably, the PS is nano-encapsulated in a calcium phosphate nanoparticle (CPNP). The invention also provides for a composition for the treatment of tumors. In one aspect, the composition includes an effective amount of the PS-encapsulated CPNP to treat tumors. Also provided herein is a composition for the imaging of target tissues, vessels, or tumors. In one aspect, the composition includes an effective amount of the PS-encapsulated CPNP to perform imaging of the target tissue, vessel, or tumor.

It is a primary object feature or advantage of the present invention to improve over the state of the art.

A further object, feature, or advantage of the invention is to provide a novel method and/or composition for the localized treatment of tumors.

A still further object, feature, or advantage of the invention is to provide a novel method and/or composition for the treatment of tumors that greatly reduces toxic side effects to the patient compared to conventional cancer treatments.

Another object, feature, or advantage of the invention is to provide a novel method and/or composition for the treatment of tumors that induces a patient's immunity.

Another object, feature, or advantage of the invention is to provide a novel method and/or composition for the treatment of metastasized tumors.

Yet another object, feature, or advantage of the invention is to provide a cost-effective novel method and/or composition for the treatment of tumors.

An object, feature, or advantage of the present invention is to provide a novel method and/or composition for the treatment of tumors that utilizes a non-toxic composition.

It is a further object, feature, or advantage of the present invention to provide a novel method and/or composition for the treatment of tumors that utilizes a resorbable composition.

Yet another object, feature, or advantage of the invention is to provide a novel method and/or composition for the treatment of tumors that utilizes a composition that is small enough in size to be administered intravenously.

Still another object, feature, or advantage of the invention is to provide a novel method and/or composition for the treatment of tumors that utilizes a composition that remains colloidally stable in physiological solutions.

An object, feature, or advantage of the present invention is to provide a novel method and/or composition for the treatment of tumors that inhibits tumor growth.

An additional object, feature, or advantage of the present invention is to provide a novel method and/or composition for the treatment of tumors that prevents tumor regrowth.

A further object, feature, or advantage of the present invention is a novel method and/or composition for the treatment of tumors that results in tumor reduction.

A still further object, feature, or advantage of the present invention is to provide a novel method and/or composition for the treatment of tumors that may be used to treat various types of tumors.

A further object, feature, or advantage of the invention is to provide a novel method and/or composition for the treatment of tumors that has little effect on the patient's healthy tissue.

A still further object, feature, or advantage of the invention is to provide a novel method and/or composition for the treatment of tumors that may be used prior to, concurrently with, or subsequent to surgery.

Yet another object, feature, or advantage of the invention is to provide a novel method and/or composition for the protection from challenge of the same tumor type.

One or more of these and/or other objects, features, or advantages of the present invention will become apparent from the specification and claims that follow. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure. No single embodiment of the invention need fulfill all or any of the objects stated herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention can be more fully understood from the following detailed description and the accompanying figures.

DETAILED DESCRIPTION

Figure 1:
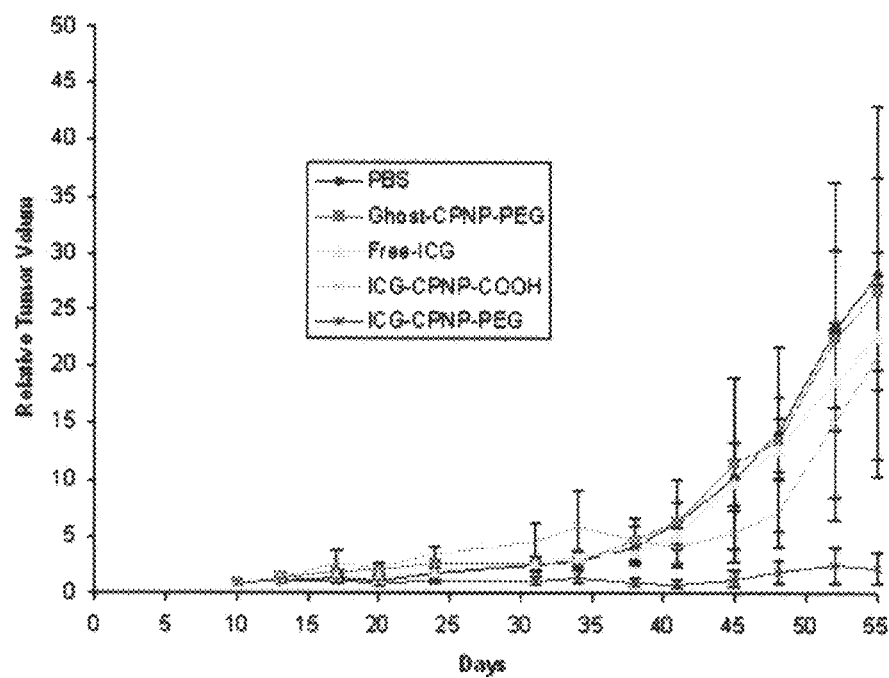
FIG. 1 shows tumor growth following photodynamic therapy with a single injection of PEGylated calcium phosphate nanoparticles containing indocyanine green, and a single near-infrared laser treatment.

The present invention now will be described more fully hereinafter with reference to the accompanying examples, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the invention set forth herein will come to mind to one skilled in the art to which this invention pertains, having the benefit of the teachings presented in the descriptions and the drawings herein. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The articles "a" and "an" are used herein to refer to one or more than one (i.e., to at least one) of the grammatical object of the article. By way of example, "an element" means one or more than one element.

Photodynamic therapy has been described as an alternative to chemotherapy or radiation therapy in the treatment of malignant tumors. Photodynamic therapy consists of three components: a photosensitizer (PS), light, and oxygen. When exposed to light of a specific wavelength, a photosensitizer is excited, and a subsequent energy transfer to molecular oxygen produces singlet oxygen (Allison, R. R., Bagnato, V. S., Cuenca, R., Downie, G. H., and Sibata, C. H. (2006) The future of photodynamic therapy in oncology. *Future Oncol.* 2: 53-71.). Highly reactive singlet oxygen rapidly reacts with nearby cellular components, ultimately leading to cell death.

The disadvantages of photodynamic therapy are mostly associated with short lifetimes of photosensitizers, an inability to penetrate sufficient light through tissue, and an inability to preferentially target cancerous tissues with photosensitizers (Allison, R. R., Bagnato, V. S., Cuenca, R., Downie, G. H., and Sibata, C. H. (2006) The future of photodynamic therapy in oncology. *Future Oncol.* 2: 53-71.). More recent studies, including a phase three clinical trial studying hepatocellular carcinoma, have explored minimally invasive procedures to tunnel light directly to tumors (A phase 3 study of talaporfin sodium and interstitial light emitting diodes treating hepatocellular carcinoma (HCC). ClinicalTrials.gov. Available at http://clinicaltrials.gov/ct2/show/NCT00355355. Accessed Dec. 22, 2008.). Likewise, deep tissue imaging necessary for the detection of cancer presents similar shortfalls (Altinoglu, E. I., Russin, T. J., Kaiser, J. M., Barth, B. M., Eklund, P. C., Kester, M., and Adair, J. H. (2008) Near-infrared emitting fluorophore-doped calcium phosphate nanoparticles for in vivo imaging of human breast cancer. *ACS Nano.* 2: 2075-2084.), namely, short lifetimes of fluorescent imaging agents, and insufficient photoefficiency; altogether limiting detection of small solid tumors. Based upon current protocols in existing literature and physical limitations of conventional PS, there is no reason to suspect that photosensitizers such as near-infrared fluorescing agents, including indocyanine green, could be used as a viable in vivo photosensitizer for cancer.

The present invention relates to compositions and methods for the treatment of tumors using PDT. Generally, the methods include the use of a nano-encapsulated photosensitizer. Preferably the PS is encapsulated in a calcium phosphate nanoparticle (CPNP). Advantageously, encapsulating the PS in a CPNP increases the half-life of the PS, increases absorption into the target cell tissue, increases the photostability of the PS, increases the photoefficiency of the PS, increases in vivo retention of the PS, or combinations thereof, ultimately making it a highly efficacious agent for use in photodynamic therapy, imaging target tissues, vessels, or tumors, and/or detecting or locating tumors. Any suitable vessels such as an artery or a vein may be imaged to obtain data regarding atherosclerosis, restenosis or graft disease. As used herein the term, "half-life" refers to the amount of time required in which half of the signal or emission from an excited PS in circulation, in tissue, or in cells, e.g. tumor cells, disappears and one half of the signal or emission remains. As used herein the term, "absorption into the target cell or target cell tissue" refers the movement of the PS into target cell or target cell tissue.

In some examples, nanoencapsulation of the PS in the CPNP increases the half-life of the PS by about 100%, 150%, 200%, 250%, 300%, 350%, 400%, 450%, 500%, 550%, or 600% or more relative to the half life of a control. The term "control" provides a reference point for measuring changes in phenotype of the PS nano-encapsulated in a CPNP. A control may comprise, for example: (a) a free PS, a non-encapsulated PS that is the same PS nanoencapsulated in the CPNP of the present invention; (b) a nano-encapsulated PS having the same PS as in the nanoencapsulated-PS of the present invention but having a different matrix or nanoencapsulation than calcium phosphate, e.g. the control may be a PS nano-encapsulated in a silica nanoparticle or nanoparticle with a matrix of PLGA; or (c) a CPNP which does not contain a PS.

In some examples, nanoencapsulation of the PS in the CPNP increases the absorption of the PS into the target cell tissue by about 30%, 40%, 50%, 60%, 70%, 75%, 80%, 85%, 90%, 95%, or 100% relative to the absorption of a control.

In some examples, nanoencapsulation of the PS in the CPNP increases the photostability of the PS by about 100%, 150%, 200%, 250%, 300%, 350%, 400%, 450%, 500%, 550%, or 600% or more relative to the photostability of a control.

In some examples, nanoencapsulation of the PS in the CPNP increases the photoefficiency of the PS by about 25%, 50%, 75%, 100%, 125%, 150%, 175%, 200%, 225%, 250%, 275%, 300%, 350%, 400%, 450%, 500%, 550%, or 600% or more relative to the photostability of a control.

Nano-encapsulating the PS in a CPNP significantly enhances biological and physical half-life of near infrared (NIR) PS, as well as enhancing quantal efficiencies. Advantageously, in contrast to conventional PS, the nano-encapsulated PS of the present invention may be useful for deep tissue imaging, for example, to image tissue to a depth greater than 1 cm, 2 cm, 3 cm or more in muscle or to a depth greater than 1 cm, 2 cm, 3 cm, 4 cm, 5 cm, 6 cm, 7 cm, 8 cm, 9 cm, 10 cm or more in breast tissue. Accordingly, nano-encapsulated PS's may be used in imaging, such as imaging target tissue, vessels, deep tissue, deep tissue tumors and also used in PDT.

Accordingly, the compositions and methods of the present invention can be used to treat a variety of mammalian tumors. As used herein, the term "treating" refers to: (i) preventing a disease, disorder or condition from occurring in a mammal, animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. For example, with respect to cancer, treatment may be measured quantitatively or qualitatively to determine the presence/absence of the disease, or its progression or regression using, for example, reduction in tumor size, a reduction in the rate of metastasis, and/or a slowing of tumor growth, and/or no worsening in disease over a specified period of time or other symptoms associated with the disease or clinical indications associated with the pathology of the cancer.

As used herein, the term "nano-encapsulated" refers to enclosing or embedding the photosensitizer within a nano matrix, e.g. within a nanoparticle. The photosensitizer may be encapsulated within any suitable matrix of a nanoparticle. As used herein, the term "nanoparticle" includes a nanosphere and/or a nanocolloid. In a preferred embodiment, the nanoparticle comprises a calcium phosphate matrix to produce a calcium phosphate nanoparticle (CPNP). CPNP includes nano-sized calcium phosphate-based composite particles. It is preferred that the nanoparticles are composed of non-toxic, resorbable compounds that are colloidally stable in physiological fluids or solutions, those solutions having a pH around 7.4. e.g. phosphate buffered 0.15M saline. Physiological fluid includes but is not limited to, blood, cerebrospinal fluid, interstitial fluid, semen, sweat, saliva, urine and the like. The term colloidally stable refers to nanoparticles that are non-agglomerated, able to form a uniform and stable suspension of solids in solution or combinations thereof. As used herein, the term "nano" in reference to nanoparticles refers to nanoparticles that are less than 200 nm in diameter and typically less than 60 nm. Typically, the photosensitizer-encapsulated nanoparticles preferably have a mean diameter of less than about 200 nm, more preferably between about 10 nm and about 75 nm, with the preferred particle diameter range between about 15 to about 25 nm. The size of nanoparticles can be measured by a number of means known in the art for sizing small particles, including the use of a Malvern Zetasizer, Nanosight NTA system, Nicomp™ particle sizer or a Coulter™ Nano-Sizer (Coulter Electronics, Harpenden, Hertfordshire, UK). Without wishing to be bound by this theory, it is believed that particles greater than 200 nm interact with organics in the bloodstream to agglomerate and do not survive the immune response.

The methods and compositions of the invention may be practiced with a variety of photosensitizers, many of which are described in D. Kessel, Editor, Photodynamic Therapy of Neoplastic Disease, Vols. I and II, CRC Press, Boca Raton, Fla., 1990) and known to one ordinarily skilled in the art. Typically, the photosensitizers are dye molecules that are photoactive substances that when exposed to light produce cytotoxic oxygen or generate bioactive lipid products from damaged cellular membranes that are useful in killing tumor cells. In some examples, the PS's act as an imaging contrast agent for use in bioimaging target tissue, deep tissue, deep tissue tumors in muscle or breast tissue. Preferably the photosensitizer works in the near-infrared (NIR) spectrum (500-900 nm, preferably 700-900 nm). Preferred photosensitizers include but are not limited to indocyanine green (IC GREEN™ dye or ICG™ dye) (Akorn, Inc., Buffalo Grove, Ill.), Cy3 Amidite, Cascade Blue©, 10-(3-sulfopropyl) acridinium betaine (SAB), fluorescein sodium salt, rhodamine WT, various coumarins, porphyrins (photofrin), and the like. In one aspect, nanoparticles may encapsulate a particular PS or a mixture of several PS's. Additionally, the nanoparticles used in the invention may encapsulate other agents, including those useful in the treatment of tumors or imaging.

Generally speaking, the concentration of photosensitizer in the nanoparticles depends on the nature of the photosensitizer used. For example, the amount of photosensitizer, such as ICG, incorporated into the nanoparticle is preferably between about 5 mg PS per gram of calcium phosphate and about 590 mg PS per gram of calcium phosphate, and more preferably between about 10 mg PS per gram calcium phosphate and about 100 mg PS per gram of calcium phosphate, and even more preferably between about 10 mg PS per gram of calcium phosphate and about 15 mg PS per gram of calcium phosphate. The particle number concentration as determined by the Nanosight Nanoparticle Tracking Analyzer is between $10^9$ particles per ml and $10^{16}$ particles per ml depending on the dosage required for the particular subject. Preferably, with regards to the particle number concentration, there should be at least one particle present for each cancer cell.

The photosensitizer-encapsulated CPNP's of the invention have the unexpected property of being efficacious in the treatment of existing tumors and protecting against tumor regrowth (subsequent challenge with tumor). Surprisingly, as shown in FIG. 1, mice receiving a single injection of PEGylated calcium phosphate nanoparticles containing indocyanine green, and a single near-infrared laser treatment, displayed minimal tumor growth. In essence, the local tumor destruction by the initial PDT treatment serves as an in situ vaccination, exposing the immune system to apoptotic and necrotic tumor tissue and stimulating a protective response. In animal models, this immune stimulation has actually resulted in the eradication of distant, metastasized tumors that were not treated with PDT as well as protection from re-challenge with the same tumor type. This result was surprising as ICG is often selected for use in imaging a tumor in part for its low toxicity, not for its ability to kill tumors.

The nanoparticles protect the encapsulated photosensitizer for an extended period of time increasing their half life from minutes to hours or longer. Advantageously, with the matrix shielding-effect retarding deleterious emission loss in circulation, the nano-encapsulated photosensitizers have greater fluorescence emission and extended circulation times for the encapsulated dye or PS. Extended circulating (biological) half life of the PS will yield greater accumulation of PS within tumor, making PDT more effective. Advantageously, CPNP's are cleared from the body by enterohepatic biliary recirculation via fecal material, thus reducing non-specific accumulation of NIR CPNP's, leading to no or fewer side effects of PDT.

A comparison of signal intensity localized within the liver and along the hepato-gastrointestinal tract at the 3 hour time point shows a lower concentration of ICG-CPNPs undergoing hepatic uptake and bile secretion relative to the free dye control, further confirming that a greater concentration of ICG-CPNP remains in circulation than free dye.

The nanoparticles protect the encapsulated photosensitizer during transport to the cancerous tissue and release the photosensitizer upon pH-dependent dissolution in the endosomal compartment of cells or around solid tumors. The calcium phosphate nanoparticle dissolves in the cellular environment as calcium and phosphate do not remain solid at low pH independent of one another. In some cases, encapsulating the PS in nanoparticles results in a 175% increase in photo efficiency and 450% greater photo stability when compared to a control of the free dye in PBS. The fluorescence emission intensity of one dye-doped CPNP is approximately $10^3$ times that of one ICG dye molecule. The PS-CPNP's of the invention also have increased stability, for example, nano-encapsulated particles are shelf-stable for at least one month and readily shipped.

Additionally, the nanoparticles used in the invention may encapsulate other agents, including those useful in the treatment of tumors. Preferred agents include drugs, apoptosis inducers such as bioactive lipids, including ceramide or dihydroceramide, DNA, plasmids, shRNA, siRNA, antineoplastic chemotherapeutics, other agents that useful in inhibiting or treating tumors.

Optionally, the nanoparticles used in the invention may be conjugated to various ligands or antibodies to facilitate targeting to the target tissue. These ligands include those that are receptor-specific as well as immunoglobulins and fragments thereof. Preferred ligands include antibodies in general and monoclonal antibodies, as well as immunologically reactive fragments of both including antiCD71 and transferrrin for breast cancer, gastrin and penta-gastrin for pancreatic and colon cancer, antiCD 151 for melanoma and similar targets for other cancerous tumors.

The nanoparticles may be PEGylated for surface polyethylene glycol (PEG) functionalizaiton to facilitate their accumulation in tumors. (Altinoglu et al. (2008) Near-infrared emitting fluorophore-doped calcium phosphate nanoparticles for in vivo imaging of human breast cancer. *ACS Nano.* 2: 2075-2084.). See Example 16. In a preferred embodiment, ICG has been encapsulated into PEGylated CPNP's. See the Examples disclosed herein.

Various methods of preparing nanoparticles for encapsulating agents such as PS may be used. See, for example, Altinoğlu, E. İ., et al. "Near-Infrared Emitting Fluorophore-Doped Calcium Phosphate Nanoparticles for in Vivo Imaging of Human Breast Cancer." *ACS Nano* 2.10 (2008): 2075-84.). CPNP's may be prepared using any suitable technique, for example, from a controlled addition to a phosphate solution to a calcium solution to the use of a double microemulsions as templates for particle size. (Bisht, S.; Bhakta, G.; Mitra, S.; Maitra, A. *International Journal of Pharmaceutics* 2004, 288, 157-168; Welzel, T.; Radtke, I.; Meyer-Zaika, W.; Heumann, R.; Epple, M. *Journal of Materials Chemistry* 2004, 14, 2213-2217; Sadasivan, S.; Khushalani, D.; Mann, S. *Chemistry of Materials* 2005, 17, 2765-2770; Sarda, S.; Heughebaert, M.; Lebugle, A. *Chemistry of Materials* 1999, 11, (2722-2727). Preferably, methods utilized to prepare nanoparticles of the invention produce colloidally stable nanoparticles with diameters less than 100 nm that are well-dispersed and avoid agglomeration in physiological fluids. The CPNPs are colloidally stable in a wide range of solutions including phosphate saline (10 mM phosphate buffered to pH 7.4, 0.14M NaCl, 0.01M KCl) and various ethanolic solutions used in the processing. More importantly, the polyethylene glycol surface conjugated CPNPs demonstrated colloidal stability and the ability to remain in the circulatory of a nude mouse model for at least 96 hours, verifying the colloidal stability and non-agglomerating characteristics in this animal model.

Exemplary detailed methods for preparing CPNP's are described elsewhere herein. See Examples 4 and 12. Briefly, the general synthesis scheme of organically-doped, functionalized calcium phosphate nanoparticles (CPNPs) was adapted from recently published silica syntheses. Wang, J.; White, W. B.; Adair, J. H. *Journal of American Ceramic Society* 2006, 89, (7), 2359-2363; Wang, J.; White, W. B.; Adair, J. H. *Journal of Physical Chemistry B* 2006, 110, 4679-4685; Li, T.; Moon, J.; Morrone, A. A.; Mecholsky, J. J.; Talham, D. R.; Adair, J. H. *Langmuir* 1999, 15, 4328-4334. It is preferred that the nanoparticles are prepared using van der Waals chromatography.

As mentioned above, any suitable photosensitizers may be encapsulated within the nanoparticles, preferably those that are infrared PS. Typically, the percent of the photosensitizer incorporated into the nanoparticles is from about 0.5% and 60% (w/w) of the total weight of the nanoparticle and photosensitizer. Preferably, the amount of added photosensitizer is between about 0.1% and about 1%% and more preferably about 0.1% of the weight of the total weight of the nanoparticle and photosensitizer.

Photosensitizer-encapsulated CPNP's may be formulated in any suitable manner. In some examples, the CPNP's comprising the PS's are conveniently formulated as sterile, freeze-dried powders containing trehalose or another lyoprotectant. Photosensitizer-encapsulated nanoparticles are conveniently formulated as sterile, freeze-dried powders containing trehalose or another lyoprotectant. A typical powder preferably contains a lyoprotectant/nanoparticle ratio in the range of about 0.1 to about 5, preferably in the range of about 0.6 to 3.0, and more preferably in the range of about 0.8 to 2.0 on a weight/weight basis. A sterile freeze-dried power containing nanoparticles and optional lyoprotectant may be reconstituted in an aqueous medium for administration to a human or other animal. The aqueous medium is preferably a pharmaceutically acceptable sterile medium, for example 5% dextrose or normal saline. Alternatively, the medium may be water for injection where the amount of lyoprotectant or other additive is sufficient to render the reconstituted material suitable for pharmaceutical or therapeutic use.

The photo sensitizer-encapsulated nanoparticles of the invention may be formulated into a variety of additional compositions. These compositions may also comprise further components, such as conventional delivery vehicles and excipients including isotonising agents, pH regulators, solvents, solubilizers, dyes, gelling agents and thickeners and buffers and combinations thereof. Suitable excipients for use with photosensitizers include water, saline, dextrose, glycerol and the like.

Appropriate formulations and dosages for the administration of photosensitizers are known in the art. The particular concentration or amount of a given photosensitizer is adjusted according to its photosensitizing potency. For example, ICG may be used at $10^{-6}$M concentration compared to $10^{-6}$M amount of Cy3 Amidite. Unexpectedly, it was discovered that nano-encapsulated PS's may be used with isotonic solutions. For example, the CPNPs are colloidally stable in a wide range of solutions including phosphate saline (10 mM phosphate buffered to pH 7.4, 0.14M NaCl, 0.01M KCl) and various ethanolic solutions used in the processing. More importantly, the polyethylene glycol surface conjugated CPNPs demonstrated colloidal stability and the ability to remain in the circulatory of a nude mouse model for at least 96 hours, verifying the colloidal stability and non-agglomerating characteristics in this animal model. Accordingly, contrary to conventional teachings of colloidal chemistry, calcium phosphate nanoparticles encapsulating PS's having citrate, amine or PEG surface functionalized particles are stable in PBS and do not form agglomerates. Suitable isotonising agents are preferably nonionic isotonising agents such as glycerol, sorbitol, mannitol, aminoethanol or propylene glycol as well as ionic isotonising agents such as sodium chloride. The solutions of this invention will contain the isotonising agent, if present, in an amount sufficient to bring about the formation of an approximately isotonic solution. The expression "an approximately isotonic solution" will be taken to mean in this context a solution that has an osmolarity of about 300 miliosmol (mOsm), conveniently 300±10% mOsm. It should be borne in mind that all components of the solution contribute to the osmolarity. The nonionic isotonising agent, if present, is added in customary amounts, i.e., preferably in amounts of about 1 to about 3.5 percent by weight, preferably in amounts of about 1.5 to 3 percent by weight. Summaries of pharmaceutical compositions suitable for use with photosensitizers are known in the art and are found, for instance, in Remington's Pharmaceutical Sciences.

As mentioned above, compositions and methods of the present invention may be used in imaging of target tissue or tumors, to treat any number of cancers or tumors or both. The nanoparticles of the invention are particularly suited for the imaging and/or treatment of deep tissue tumors, such breast cancer, ovarian cancer, brain cancer, lung cancer, hepatic cancers, and the like. Types of mammalian tumors that can be treated using the compositions and methods of the present invention include, but are not limited to all solid tumors, cutaneous tumors, melanoma, malignant melanoma, renal cell carcinoma, colorectal carcinoma, colon cancer, hepatic metastases of advanced colorectal carcinoma, lymphomas (including glandular lymphoma), malignant lymphoma, Kaposi's sarcoma, prostate cancer, kidney cancer, ovarian cancer, lung cancer, head and neck cancer, pancreatic cancer, mesenteric cancer, gastric cancer, rectal cancer, stomach cancer, bladder cancer, leukemia (including hairy cell leukemia and chronic myelogenous leukemia), breast cancer, solid breast tumor growth, non-melanoma skin cancer (including squamous cell carcinoma and basal cell carcinoma), hemangioma multiple myeloma, and glioma. Preferably, the cancer is brain, breast, lung, pancreatic, hepatic, colon, melanoma, ovarian cancer, or metastases thereof. In addition, embodiments for the invention can be adapted for non-solid tumors, including leukemias or lymphomas, via whole-body PDT therapy using nano-encapsulated photosensitizers and most preferably using encapsulated NIR PS within CPNP.

In one aspect, the methods include administering systemically or locally the photosensitizer-encapsulated nanoparticles of the invention. Any suitable route of administration may be used, including, for example, topical, intravenous, oral, subcutaneous, local (e.g. in the eye) or by use of an implant. Advantageously, the small size, colloidal stability, non-agglomeration properties, and enhanced half-life of the nanoparticles renders the nano-encapsulated photosensitizer especially suitable for intravenous administration. Additional routes of administration are subcutaneous, intramuscular, or intraperitoneal injections in conventional or convenient forms. For topical administration, the photosensitizer-encapsulated nanoparticles may be in standard topical formulations and compositions including lotions, suspensions or pastes. For example, ICG encapsulated CPNP's may be administered by various means, but preferably by intravenous injection.

The dose of photosensitizer-encapsulated nanoparticles may be optimized by the skilled person depending on factors such as, but not limited to, the photosensitizer chosen, the nature of the therapeutic protocol, the individual subject, and the judgment of the skilled practitioner. Preferred amounts of photosensitizer-encapsulated nanoparticles are those which are clinically or therapeutically effective in the treatment method being used. Such amounts are referred herein as "effective amounts".

It should be noted that the various parameters used for effective PDT in the invention are interrelated. Therefore, the dose should also be adjusted with respect to other parameters, for example, fluence, irradiance, and duration of the light used in PDT. With photo sensitizer-encapsulated nanoparticles, for example, the form of administration, such as when coupled to a target-specific ligand, such as an antibody or an immunologically active fragment thereof, is one factor considered by a skilled artisan. Yet, the ability of NIR PS to biomage as well as PDT will allow for a more rigorous determination of these critical dosing parameters in real time.

Depending on the needs of the subject and the constraints of the treatment method being used, smaller or larger doses of photosensitizer-encapsulated nanoparticles may be needed. The doses may be a single administration or include multiple dosings over time. For compositions which are highly specific to the target skin tissues and cells, such as those with the photosensitizer-encapsulated nanoparticles conjugated to a highly specific monoclonal antibody preparation or specific receptor ligand, dosages in the range of 0.005-10 mg/kg of body weight are suggested. For compositions, which are less specific to the target, larger dosages, up to 1-10 mg/kg, may be desirable. The preferred range for use in mice is from 0.05 mg/kg to 10 mg/kg. The useful range in humans for the photosensitizer-encapsulated nanoparticles will generally be lower than mice, such as from 0.005 mg/kg to 2 mg/kg. The foregoing ranges are merely suggestive in that the number of variables with regard to an individual treatment regime is large and considerable deviation from these values may be expected. The skilled artisan is free to vary the foregoing concentrations so that the uptake and stimulation/restoration parameters are consistent with the therapeutic objectives disclosed above.

In addition to human subjects, the present invention may be applied to non-human animals, such as mammals, particularly those important to agricultural applications (such as, but not limited to, cattle, sheep, horses, and other "farm animals"), industrial applications (such as, but not limited to, animals used to generate bioactive molecules as part of the biotechnology and pharmaceutical industries), and for human companionship (such as, but not limited to, dogs and cats).

Each photosensitizer encapsulated in the nanoparticle requires activation with an appropriate wavelength of radiation. As such, the methods of the invention may be conducted with any irradiation, preferably in the range of visible light, which activates the photosensitizer used. Preferably, the irradiation contains one or more wavelengths which is capable of penetrating the skin to activate the photosensitizer used. The wavelength(s) of radiation or light useful in the invention depends on the activation range of the photosensitizer used as part of the treatment method. It is understood that photosensitizers are chemically distinct and fluorescence at different wavelengths. For example, with respect to Cy3, the excitation and emission wavelengths are 532 and about 570 nm, respectively. With respect to ICG, the maximum excitation and emission are at 780 and 825 in PBS, respectively. Typically, the wavelength may be from about 500 nm to about 900 nm. Wavelengths of about 780 nanometers (nm) are preferred, depending upon the photosensitizer and upon the depth of tissue penetration desired. More preferred are wavelengths from about 750 to about 800 nm, most preferred from about 770 to about 790 nm. For example, ICG, can be activated by a light source emitting a wavelengths from 700- to 800 nm.

Any suitable source of radiation that causes the particular dye to fluoresce may be used in the present methods, including but not limited to light, ultrasound, magnetic force, electromagnetic radiation in the ultra violet or visible electromagnetic spectrum or near infrared. The type and amount of radiation applied to the patient administrated the encapsulated nanoparticles of the invention must be sufficient to cause the fluorescent dye present in the patient to fluoresce. Preferably, the radiation applied does not cause excessive damage to the normal surrounding tissue. The particular energy source and amount of energy applied will depend upon the type of fluorescent dye administered to the subject.

An appropriate light source, preferably a laser, laser diode, or laser diode array, in the range of about 500 to about 900 nm, depending on the absorption spectrum of the photosensitizer, may be used for photosensitizer activation.

The light dose administered during the PDT treatment contemplated herein can vary, and can range between about 0.1 to about 200 $J/cm^2$. The light dose is chosen depending on potency of the photosensitizer, the dosage of the photosensitizer and the purpose of the photodynamic treatment. When PDT is being conducted to ablate tumor tissue, then higher doses of irradiation, in the range of 100-250 $J/cm^2$ and sometimes even higher is generally desirable. When PDT is conducted to modulate an immune response, rather than killing target tissue, it is preferred that the irradiation be at low dose to reduce unwanted side effects while still activating the photosensitizer. The irradiation dose used (referred to as "low dose PDT") is preferably of lower intensity than that used for oncogenic treatment. A preferred range is from 0.1 to 20 $J/cm^2$.

When PDT is conducted to treat (choroidal) neovasculature in the eye (such as that associated with AMD), intermediate light doses, in the range of 20 to 100 $J/cm^2$ is generally used. For example, the dosage of light recommended for Visudyne™ used in the treatment of AMD is 50 $J/cm^2$. Increases in irradiance may decrease the exposure times.

Generally, a higher dose of photosensitizer will decrease the light dose required to exert a therapeutic effect.

The time of light irradiation after administration of the photosensitizer-encapsulated nanoparticles may be important as one way of maximizing the selectivity of the treatment, thus minimizing damage to structures other than the target tumor cells. Light treatment within 9 days, and more preferably within an 1 to 2 days after administration of the photosensitizer-encapsulated nanoparticles should generally be used, to ensure accumulation of PS within tumor. However, specific irradiation schedules can be designed for each type of cancer being treated The nanoparticles are administered to the subject and the tumor or tissue in the subject is exposed for a sufficient amount of time to a photo-activating amount of light at a wavelength that activates the PS sufficient to obtain the desired response. In some cases, the desired response is being able to bioimage or detect the target tissue or tumor, or to perform PDT using the methods and compositions of the present invention for a sufficient period of time effective to inhibit or reduce tumor growth or tumor size. The desired response may be compared to a control if desired.

EXAMPLES

Example 1

Human MDA-MB-231 breast cancer cells were xenografted into athymic mice ($1 \times 10^7$ cells/site) on day 0. Following tumor establishment, mice received 100 µl injections of free- or nano-encapsulated indocyanine green (ICG), in PEGylated calcium phosphate nanoparticles (CPNP-PEG) or citrate-terminated calcium phosphate nanoparticles (CPNP-COOH) ($5 \times 10^{-7}$ M in $2 \times 10^{14}$ particles) on day 8, or equivalent injections of controls (PBS or empty nanoparticles; Ghost-CPNP-PEG). 24 hours after injections (day 9), each tumor was exposed to a single dose of near-infrared (785 nm) laser treatment (power density of 50 J/cm$^2$). Beginning on day 10, tumors were measured regularly, and tumor volumes relative to initial tumor measurements were calculated and reported. See FIG. 1 showing the results of mice receiving ICG-CPNP-PEG, and subsequent near-infrared treatment, displayed minimal tumor growth that was significantly different from all other treatment groups (2-way ANOVA, $p<0.05$, $n=3$ in each group).

Example 2

Additionally, protein carbonylation was studied as a marker for oxidation. Carbonylation is an irreversible oxidative modification, and was detected by immunodetection of specific derivatized protein carbonyls. MDA-MB-231 cells were treated with empty PEGylated nanoparticles or PEGylated nanoparticles containing indocyanine green. Cells were exposed to 9 minutes of light (785 nm excitation filter) from a Kodak Imaging Station, and lysed in protein lysis buffer. Lysates containing an equal amount of total protein were derivatized with 2,4-dinitrophenylhydrazine to label protein carbonyls. Western blotting of derivatized lysates, using a dinitrophenyl-specific primary antibody, revealed protein carbonylation.

Figure 2:
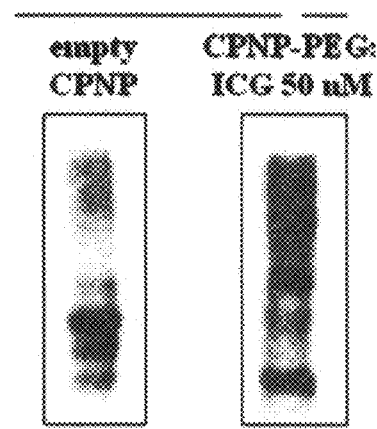
FIG. 2 shows protein oxidation induced by photodynamic therapy using PEGylated calcium phosphate nanoparticles containing indocyanine green.

FIG. 2 demonstrates that protein from cells receiving PEGylated nanoparticles (CPNP-PEG) containing indocyanine green (ICG), and subsequent near-infrared treatment, was extensively oxidized compared to protein from cells treated with empty nanoparticles, demonstrating an oxidative mechanism characteristic of photodynamic therapy. Increased carbonylation, corresponding to increased protein oxidation, is evident by an increase in high molecular weight protein bands.

Example 3

Calcium Phosphate Nanocomposite Particles for In Vitro Imaging and Encapsulated Chemotherapeutic Drug Paradigm-shifting modalities to more efficiently deliver drugs to cancerous lesions require the following attributes: nanoscale-size, targetability and stability under physiological conditions. Often, these nanoscale drug delivery vehicles are limited due to agglomeration, poor solubility or cytotoxicity. Thus, we have designed a methodology to encapsulate hydrophobic antineoplastic chemotherapeutics within a 20-30 nm diameter, pH-responsive, non-agglomerating, non-toxic calcium phosphate nanoparticle matrix. In the present study, we report on calcium phosphate nanocomposite particles (CPNP) that encapsulate both fluorophores and chemotherapeutics, are colloidally stable in physiological solution for extended time at 37° C. and can efficaciously deliver hydrophobic antineoplastic agents, such as ceramide, in several cell model systems.

Nanoparticles with fluorescent properties have been prepared by several synthetic approaches (Adair, J. H., Kumar, R., Antolino, N., Szepesi, C. J., Kimel, R. A., Rouse, S. M. In Colloidal lessons learned for dispersion of nanosize particulate suspensions, Proceedings of the World Academy of Ceramics, Faenza, Italy, 2005; Baumard, J. F., Ed. Techna Group SrI: Faenza, Italy, 2005; pp 93-145; Bisht, S.; Chattopadhyay, D.; Maitra, A. J. Biomedical Nanotechnology 2006, 2, 229-238; Ostafin, A. E.; Siegel, M.; Wang, Q.; Mizukami, H. Microporous and Mesoporous Materials 2003, 57, 47-55; Ow, H.; Larson, D. R.; Srivasatava, M.; Baird, B. A.; Webb, W. W.; Wiesner, U. Nano Letters 2005, 5, (1), 113-117; Schmidt, H. T.; Kroczynski, M.; Maddox, J.; Chen, Y.; Josephs, R.; Ostafin, A. E. Journal of Microencapsulation 2006, 23, (7), 769-781; Tan, W.; Wang, K.; He, X.; Zhao, X. J.; Drake, T.; Wang, L.; Bagwe, R. P. Medicinal Research Reviews 2004, 24, (5), 621-638; Morgan, T. T.; Muddana, H. S.; Nano Lett., 2008, 8 (12), pp 4108-4115.; Nano Lett., 2008, 8 (12), pp 4116-4121; ACS Nano, 2008, 2 (10), pp 2075-2084.), some of which exploit the benefits of self-assembly, particularly reverse micelles, to prepare a wide range of nanocolloids. (Adair, J. H.; Li, T.; Kido, T.; Havey, K.; Moon, J.; Mecholsky, J.; Morrone, A.; Talham, D. R.; Ludwig, M. H.; Wang, L. Materials Science & Engineering R-Reports 1998, 23, (4-5), 139-242; Arriagada, F. J.; Osseoasare, K. Colloid Chemistry of Silica 1994, 234, 113-128; Arriagada, F. J.; Osseoasare, K. Journal of Colloid and Interface Science 1995, 170, (1), 8-17; Hunter, R. J., Zeta Potential in Colloid Science: Theory and Practice. Academic Press: New York, N.Y., 1981; Lai, C.; Tang, S. Q.; Wang, Y. J.; Wei, K. Materials Letters 2005, 59, (2-3), 210-214; Roy, I.; Mitra, S.; Maitra, A.; Mozumdar, S. Int. J. Pharmaceutics 2003, 250, 25-33; Maitra, A. Expert Rev. Mol. Diagn. 2005, 5, (6), 893-905; Adair, J. H.; Suvaci, E. Current Opinion in Colloid and Interface Science 2000, 5, (1-2), 160-167; Bisht, S.; Bhakta, G.; Mitra, S.; Maitra, A. Int. J. Pharmaceutics 2005, 288, 157-168; Li, T.; Moon, J.; Morrone, A. A.; Mecholsky, J. J.; Adair, J. H. Langmuir 1999, 15, (13), 4328-4334; Wang, J.; White, W. B.; Adair, J. H. J Phys Chem B Condens Matter Mater Surf Interfaces Biophys 2006, 110, (10), 4679-85). For example, reverse micelle techniques have been used to produce nearly monodisperse fluorescent semiconductor quantum dots with various shapes and sizes as well as to capture organic fluorophores within silica inorganic matrices. (Bisht, S.; Chattopadhyay, D.; Maitra, A. J. Biomedical Nanotechnology 2006, 2, 229-238; Ostafin, A. E.; Siegel, M.; Wang, Q.; Mizukami, H. Microporous and Mesoporous Materials 2003, 57, 47-55; Ow, H.; Larson, D. R.; Srivasatava, M.; Baird, B. A.; Webb, W. W.; Wiesner, U. Nano Letters 2005, 5, (1), 113-117; Schmidt, H. T.; Kroczynski, M.; Maddox, J.; Chen, Y.; Josephs, R.; Ostafin, A. E. Journal of Microencapsulation 2006, 23, (7), 769-781; Tan, W.; Wang, K.; He, X.; Zhao, X. J.; Drake, T.; Wang, L.; Bagwe, R. P. Medicinal Research Reviews 2004, 24, (5), 621-638; Adair, J. H.; Kumar, R.; Antolino, N.; Szepesi, C. J.; Kimel, R. A.; Rouse, S. M. In Colloidal lessons learned for dispersion of nanosize particulate suspensions, Proceedings of the World Academy of Ceramics, Faenza, Italy, 2005; Baumard, J. F., Ed. Techna Group SrI: Faenza, Italy, 2005; pp 93-145; Jaiswal, J. K.; Simon, S. M. Trends in Cell Biology 2004, 14, (9), 497-504). While suitable for drug delivery in vitro where immune responses do not exist, semi-conductor or silica nanocomposite particles with surface decoration are not particularly efficacious for drug delivery in humans. (Adair, J. H., Kumar, R., Antolino, N., Szepesi, C. J., Kimel, R. A., Rouse, S. M. In Colloidal lessons learned for dispersion of nanosize particulate suspensions, Proceedings of the World Academy of Ceramics, Faenza, Italy, 2005; Baumard, J. F., Ed. Techna Group SrI: Faenza, Italy, 2005; pp 93-145; Tan, W.; Wang, K.; He, X.; Zhao, X. J.; Drake, T.; Wang, L.; Bagwe, R. P. Medicinal Research Reviews 2004, 24, (5), 621-638; Yao, G.; Wang, L.; Wu, Y.; Smith, J.; Xu, J.; Zhao, W.; Lee, E.; Tan, W. Anal Bioanal Chem 2006, 385, 518-524). Biodegradation of the decorated therapeutics prior to delivery can be severe. To overcome these limitations and realize the full potential of nanocomposite drug and fluorophore delivery systems, we have developed non-agglomerating nano-sized calcium phosphate-based composite particles. Reasonably high, but benign, concentrations of calcium and phosphate (1 to 5 mM) occur in all vertebrates and are naturally non-toxic as well as bioresorbable. (Bonucci, E., Calcification in Biological Systems. CRC Press: Boca Raton, 1992; p 406; Coe, F. L.; Favus, M. J.; Pak, C. Y. C.; Parks, J. H.; Preminger, G. M., Kidney Stones: Medical and Surgical Management. Lippincott-Raven Publishers: Philadelphia, 1996; p 1109; Freshney, R. I., Culture of Animal Cells: A Manual of Basic Technique. 3rd ed.; Wiley-Liss, Inc.: New York, 1994; p 486). Calcium phosphate has been widely used to provide transfection of DNA and deliver drugs via surface decoration of calcium phosphate microparticles. (Bisht, S.; Chattopadhyay, D.; Maitra, A. J. Biomedical Nanotechnology 2006, 2, 229-238; Schmidt, H. T.; Kroczynski, M.; Maddox, J.; Chen, Y.; Josephs, R.; Ostafin, A. E. Journal of Microencapsulation 2006, 23, (7), 769-781; Roy, I.; Mitra, S.; Maitra, A.; Mozumdar, S. Int. J. Pharmaceutics 2003, 250, 25-33; Maitra, A. Expert Rev. Mol. Diagn. 2005, 5, (6), 893-905; Bisht, S.; Bhakta, G.; Mitra, S.; Maitra, A. Int. J. Pharmaceutics 2005, 288, 157-168; Yih, T. C.; Al-Fandi, M. Journal of Cellular Biochemistry 2006, 97, 1184-1190). The present study reports the colloidal properties of stable, non-aggregating, 20 nm nanocomposite calcium phosphate particles embedded with fluoroprobes and a small amphiphilic neoplastic drug, ceramide, for simultaneous bioimaging and drug delivery to a range of cell types, including melanoma and breast adenocarcinoma cell lines.

One advantage of calcium phosphate as an encapsulating material relative, for example, to polymeric nanoparticles or liposomes (Yih, T. C.; Al-Fandi, M. Journal of Cellular Biochemistry 2006, 97, 1184-1190; Shabbits, J. A.; Mayer, L. D. Anticancer Res 2003, 23, (5A), 3663-9; Shabbits, J. A.; Mayer, L. D. Biochim Biophys Acta 2003, 1612, (1), 98-106 Stover, T. C.; Sharma, A.; Robertson, G. P.; Kester, M. Clinical Cancer Research 2005, 11, (9), 3465-3474; Panyam, P.; Labhassetwar, V. Advanced Drug Delivery Reviews 2003, 55, 329-347), is its variable solubility in cells. (Bisht, S.; Chattopadhyay, D.; Maitra, A. J. Biomedical Nanotechnology 2006, 2, 229-238; Schmidt, H. T.; Kroczynski, M.; Maddox, J.; Chen, Y.; Josephs, R.; Ostafin, A. E. Journal of Microencapsulation 2006, 23, (7), 769-781; Roy, I.; Mitra, S.; Maitra, A.; Mozumdar, S. Int. J. Pharmaceutics 2003, 250, 25-33; Maitra, A. Expert Rev. Mol. Diagn. 2005, 5, (6), 893-905; Yih, T. C.; Al-Fandi, M. Journal of Cellular Biochemistry 2006, 97, 1184-1190; Chander, S.; Fuerstenau, D. W. Colloids and Surfaces 1982, 4, 101-120; Magne, D.; Faucheus, C.; Grimadi, G.; Daculsi, G.; Guicheux, J. Drug Discovery Today 2002, 7, (17), 928-931; Prakash, K. H.; Kumar, R.; Ooi, C. P.; Cheang, P.; Khor, K. A. Langmuir 2006, 22, 11002-11008). Many chemotherapeutics cannot be used clinically due to insolubility, phase separation, and toxicology. (Yih, T. C.; Al-Fandi, M. Journal of Cellular Biochemistry 2006, 97, 1184-1190; Panyam, P.; Labhassetwar, V. Advanced Drug Delivery Reviews 2003, 55, 329-347). Therefore, encapsulation of insoluble therapeutics in a pH tunable soluble nanoparticle can provide a novel means of transportation to specific cells or tissues and also optimize their biological concentration at the site of action. (Bisht, S.; Chattopadhyay, D.; Maitra, A. J. Biomedical Nanotechnology 2006, 2, 229-238; Schmidt, H. T.; Kroczynski, M.; Maddox, J.; Chen, Y.; Josephs, R.; Ostafin, A. E. Journal of Microencapsulation 2006, 23, (7), 769-781). An example of such a water-insoluble therapeutic molecule is ceramide (Cer), an experimental therapeutic agent which has been shown to play an important role in the apoptosis of cancer cells. (Ogretmen, B.; Hannun, Y. A. Nature Reviews 2004, 3, 604-616). Cer is a lipid-derived second messenger (Fox, T. E.; Finnegan, C. M.; Blumenthal, R.; Kester, M. Cell Mol Life Sci 2006, 63, (9), 1017-23; Bourbon, N. A.; Sandirasegarane, L.; Kester, M. J Biol Chem 2002, 277, (5), 3286-92) that preferentially induces tumor apoptosis (Stover, T. C.; Sharma, A.; Robertson, G. P.; Kester, M. Clinical Cancer Research 2005, 11, (9), 3465-3474) by inhibiting over-expressed pro-survival AKT3, a kinase that is activated in 70% of melanomas through AKT3 amplification or PTEN loss. Stahl, J. M.; Sharma, A.; Cheung, M.; Zimmerman, M.; Cheng, J. Q.; Bosenberg, M. W.; Kester, M.; Sandirasegarane, L.; Robertson, G. P. Cancer Res 2004, 64, (19), 7002-10). It has been previously shown that as the degree of malignancy increases, the level of Cer in the cell decreases. (Riboni, L.; Campanella, R.; Bassi, R.; Villani, R.; Gaini, S. M.; Martinelli-Boneschi, F.; Viani, P.; Tettamanti, G. Glia 2002, 39, 105-113). Despite Cer's potential usefulness as an anti-cancer agent, many of these lipophilic agents, especially those with longer chains, are almost completely insoluble in water, making administration difficult even in several model systems. Currently, in pre-clinical studies, ceramides are either dissolved in dimethylsulfoxide (DMSO) or administered via liposomal micelle encapsulation. (Stover, T. C.; Sharma, A.; Robertson, G. P.; Kester, M. Clinical Cancer Research 2005, 11, (9), 3465-3474; Shabbits, J. A.; Mayer, L. D. Anticancer Res 2003, 23, (5A), 3663-9; Shabbits, J. A.; Mayer, L. D. Biochim Biophys Acta 2003, 1612, (1), 98-106).

Previous reports have described the synthesis strategy for nanocomposite colloids in detail and thus, will only be briefly described. (Morgan, T. T.; Muddana, H. S.; Altinoglu, E. I.; Rouse, S. M.; Tabakovic, A.; Nano Lett., 2008, 8 (12), pp 4108-4115.; Nano Lett., 2008, 8 (12), pp 4116-4121; ACS Nano, 2008, 2 (10), pp 2075-2084; Adair, J. H.; Li, T.; Kido, T.; Havey, K.; Moon, J.; Mecholsky, J.; Morrone, A.; Talham, D. R.; Ludwig, M. H.; Wang, L. *Materials Science & Engineering R-Reports* 1998, 23, (4-5), 139-242; Wang, J.; White, W. B.; Adair, J. H. *J Phys Chem B Condens Matter Mater Surf Interfaces Biophys* 2006, 110, (10), 4679-85; Adair, J. H.; Kumar, R.; Antolino, N.; Szepesi, C. J.; Kimel, R. A.; Rouse, S. M. In Colloidal lessons learned for dispersion of nanosize particulate suspensions, Proceedings of the World Academy of Ceramics, Faenza, Italy, 2005; Baumard, J. F., Ed. Techna Group SrI: Faenza, Italy, 2005; pp 93-145). We have adapted the double reverse-micelle strategy to synthesize amine, carboxylate-, and pegylated surface functionalized CPNP (See Examples herein). (Nano Lett., 2008, 8 (12), pp 4108-4115.; Nano Lett., 2008, 8 (12), pp 4116-4121; ACS Nano, 2008, 2 (10), pp 2075-2084.). We utilized the positively charged, amine-functionalized CPNP in all of the following studies. These nanocolloids are routinely composed of 20 nm diameter calcium phosphate particles, with a zeta potential of +30 mV. The HPLC concentration strategy yields $10^{15}$ particles per ml of solution, and removes amphiphile and cyclohexane byproducts to final concentrations of less than 0.5 mM and 15 ppm, respectively. HPLC-concentrated CPNP are readily dispersed for extended time in phosphate buffered saline (PBS), 10 mM phosphate buffered at pH 7.4, 0.14M NaCl, and 0.01M KCl, solutions without agglomeration. Using this formulation, CPNP have been introduced into a variety of cell culture media including those that have fetal bovine serum present.

Figure 3:
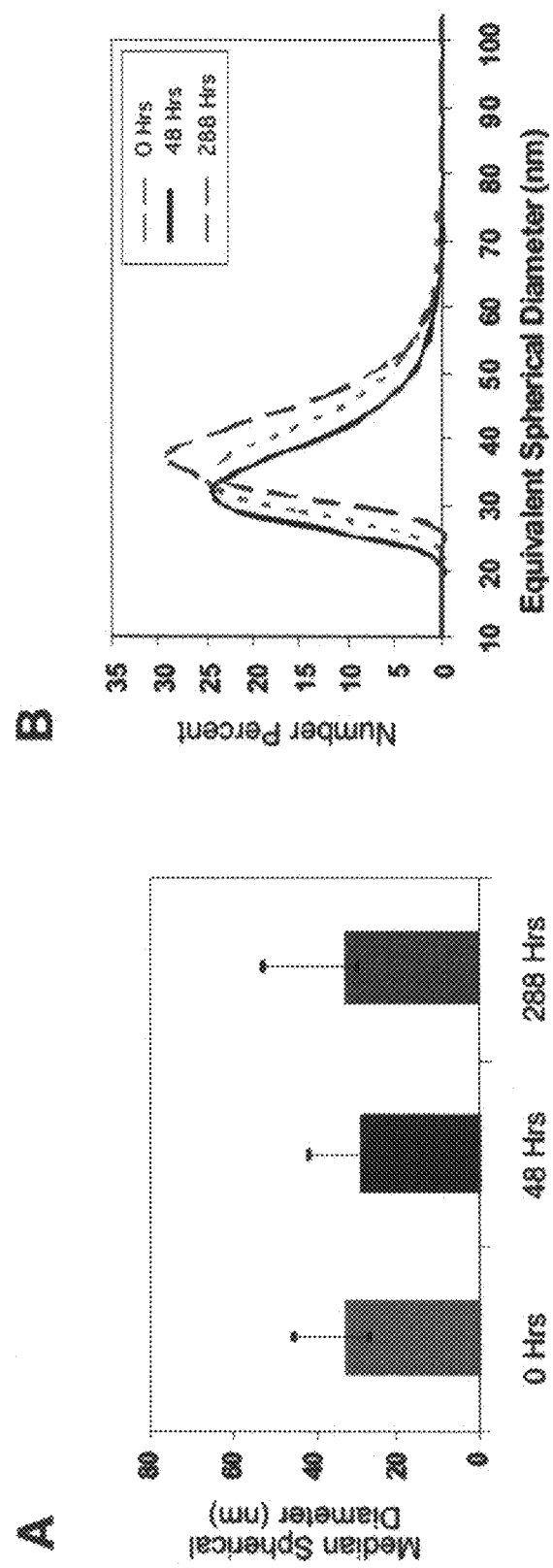
FIG. 3. shows the colloidal stability of CPNPs. The hydrodynamic diameter of the CPNPs in PBS was evaluated as a function of time at 37° C. to evaluate colloidal stability. (A) Mean hydrodynamic diameter (±standard deviation) for the CPNPs at 0 time, 48 hours, and 288 hours at 37° C.; and (B) Hydrodynamic diameter distributions for each of the times at physiological temperature.

The colloidal stability of some nanocolloids, particularly organic-based systems such as liposomes and dendrimers, can be sensitive to temperature changes because of entropic effects. (Hunter, R. J., *Zeta Potential in Colloid Science: Theory and Practice*. Academic Press: New York, N.Y., 1981; Napper, D. H., *Polymeric Stabilization of Colloidal Dispersions*. Academic Press: New York, N.Y., 1983). The colloidal stability of CPNP based on particle size distribution was evaluated in PBS at 37° C. for an extended time by quasi-elastic light scattering (QELS) (FIG. 3). The CPNP used for FIG. 3 yielded the mean diameter and lognormal standard deviation of 31.30±0.19 nm after 48 hour equilibration at 37° C. This remained relatively unchanged after 288 hours (37.40 nm±0.16). The size distributions shown in FIG. 3 are consistent with the probability analyses having significant overlap among the particle size distributions, verifying the colloidally stable CPNP suspensions. These data indicate that our approach to preparing CPNP formulations represents a highly stable nanocomposite colloid in physiological conditions for a minimum of two weeks. Our synthetic scheme offers control and design of colloid size distribution, a persistent issue in nanoparticle synthesis. Nano Lett., 2008, 8 (12), pp 4108-4115.; Nano Lett., 2008, 8 (12), pp 4116-4121; ACS Nano, 2008, 2 (10), pp 2075-2084.; Funk, J. E.; Dinger, D. R., *Predictive Process Control of Crowded Particulate Suspensions: Applied to Ceramic Manufacturing*. Kluwer Publishing: Boston, Mass., 1994

A unique feature of CPNP is the ability to simultaneously image and deliver therapeutics as a function of solution pH. Calcium phosphates, regardless of Ca:P ratio, crystallinity, or phase, are relatively insoluble at physiological pH (pH 7.4) and become increasingly soluble below pH 6.5. (Lai, C.; Tang, S. Q.; Wang, Y. J.; Wei, K. *Materials Letters* 2005, 59, (2-3), 210-214; Roy, I.; Mitra, S.; Maitra, A.; Mozumdar, S. *Int. J. Pharmaceutics* 2003, 250, 25-33; Maitra, A. *Expert Rev. Mol. Diagn.* 2005, 5, (6), 893-905; Panyam, P.; Labhassetwar, V. *Advanced Drug Delivery Reviews* 2003, 55, 329-347; Chander, S.; Fuerstenau, D. W. *Colloids and Surfaces* 1982, 4, 101-120; Prakash, K. H.; Kumar, R.; Ooi, C. P.; Cheang, P.; Khor, K. A. *Langmuir* 2006, 22, 11002-11008). We are exploiting this pH tunable solubility to deliver drugs with extreme hydrophobicity, such as ceramide ($Cer_6$ and $Cer_{10}$). Despite the efficacy of exogenous Cer delivered via DMSO or liposomes in cell culture systems or in animal models, the use of Cer as a systemic chemotherapeutic is still limited by hydrophobicity or metabolism, traits shared by many amphiphilic therapeutics. Calcium phosphates are by nature hydrophilic. If a hydrophobic drug is encapsulated, CPNP can be used as a pH-dependent vehicle to deliver the immiscible drug through the blood stream to target tissue or cells where the lower intercellular pH then dissolves the calcium phosphate nanoparticle releasing the drug. Recent submitted data demonstrate, using fluorescence correlation spectroscopy, that low pH either ex situ or in vitro induces dissolution of the CPNPs, releasing encapsulated Cy3-fluorophore. (Nano Lett., 2008, 8 (12), pp 4108-4115.; Nano Lett., 2008, 8 (12), pp 4116-4121; ACS Nano, 2008, 2 (10), pp 2075-2084). In the first set of experiments, we wanted to examine whether ceramide-doped CPNP could be employed for both simultaneous imaging and drug delivery in cultured melanoma cells.

Figure 4:
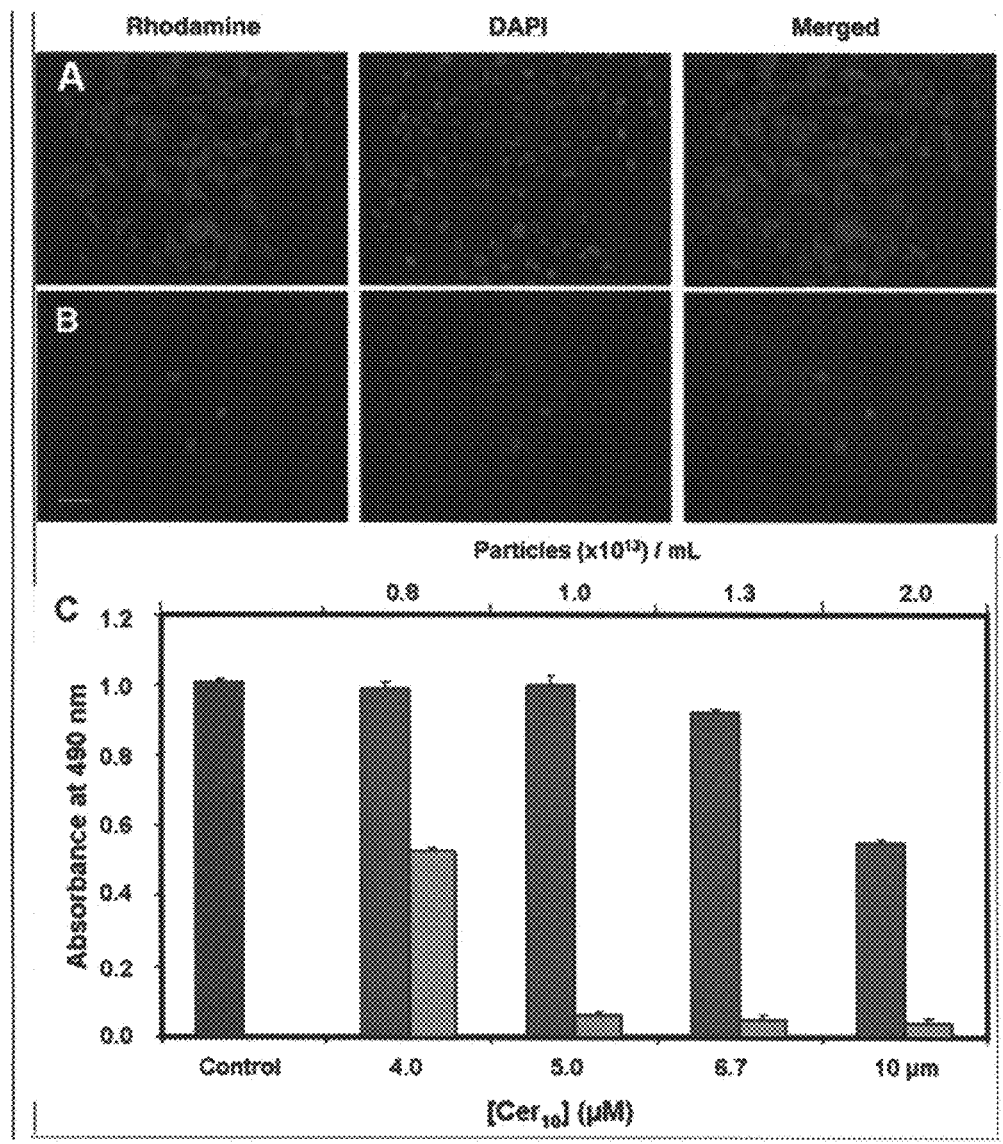
FIG. 4 shows the in vitro effect of $Cer_{10}$-CPNP on melanoma cell survival and viability. Representative images of cultured melanoma UACC 903 cells exposed to rhodamine WT-CPNP without (A) and with (B) $Cer_{10}$. Fluorescent $Cer_{10}$-CPNP, unlike control CPNP, induce melanoma cell death; and (C) MTS cytotoxicity assay demonstrating dosage responsive cytotoxic actions of $Cer_{10}$-CPNPs. Control CPNPs exhibit modest cytotoxicity at the highest particle number concentration. Values are mean±SEM for three independent experiments, each experiment replicated in triplicate. The green bar represents $Cer_{10}$ in DMSO, the purple bar represents the CPNP, and the blue bar represents $Cer_{10}$ in CPNP. The scale bars in A and B are 50 µm. The results for the CPNP (purple bar) are shown in the bar positioned to the left of the $Cer_{10}$ in CPNP (blue bar).

Cultured UACC 903 melanoma cells were chosen as a model system since they respond to exogenous Cer with increased apoptosis. (Shabbits, J. A.; Mayer, L. D. *Anticancer Res* 2003, 23, (5A), 3663-9; Stover, T. C.; Sharma, A.; Robertson, G. P.; Kester, M. *Clinical Cancer Research* 2005, 11, (9), 3465-3474). Thus, we next investigated the use of Cer-doped CPNP for simultaneous imaging and efficacy of inducing cell death in human melanoma cell lines. Decanoyl-ceramide ($Cer_{10}$) and fluorophore, rhodamine-WT (Rh-WT), were encapsulated within the calcium phosphate matrix of each particle. In these experiments, we successfully delivered one of the most hydrophobic ceramides, $Cer_{10}$, a physiological long chain ceramide that heretofore could not be administered in aqueous formulations. Control CPNP containing fluorophore, but not Cer, exhibited a perinuclear or cytosolic imaging profile in melanoma, distinct from the DAPI-stained nuclei (FIG. 4A, left). Of significance, the control CPNP did not induce any significant cellular toxicity (FIG. 4A, middle and right panel). In contrast, melanoma cells are particularly sensitive to the apoptotic effects of $Cer_{10}$-calcium phosphate nanoparticles ($2 \times 10^{13}$ particles/mL of 30 nm-diameter particles that deliver a final $Cer_{10}$ concentration of 10 μM) (FIGS. 4B and 4C). Cer concentration was determined by HPLC-MS/MS after EDTA-dissolution of the CPNPs. Cell based cytotoxicity assays (See Supporting Information) confirmed that the $Cer_{10}$-CPNP reduced melanoma cell survival to less than 5% at 5 μM (FIG. 4C). The limited cytotoxicity associated with empty control CPNP (no ceramide present) at, or above, $2 \times 10^{13}$ particles/mL is most likely due to the high concentration of amines associated with the surfaces of particles present in the cytosol of the cells. Our results indicate that an optimal concentration for the combination of ceramide and particle number in vitro can be achieved.

Figure 5:
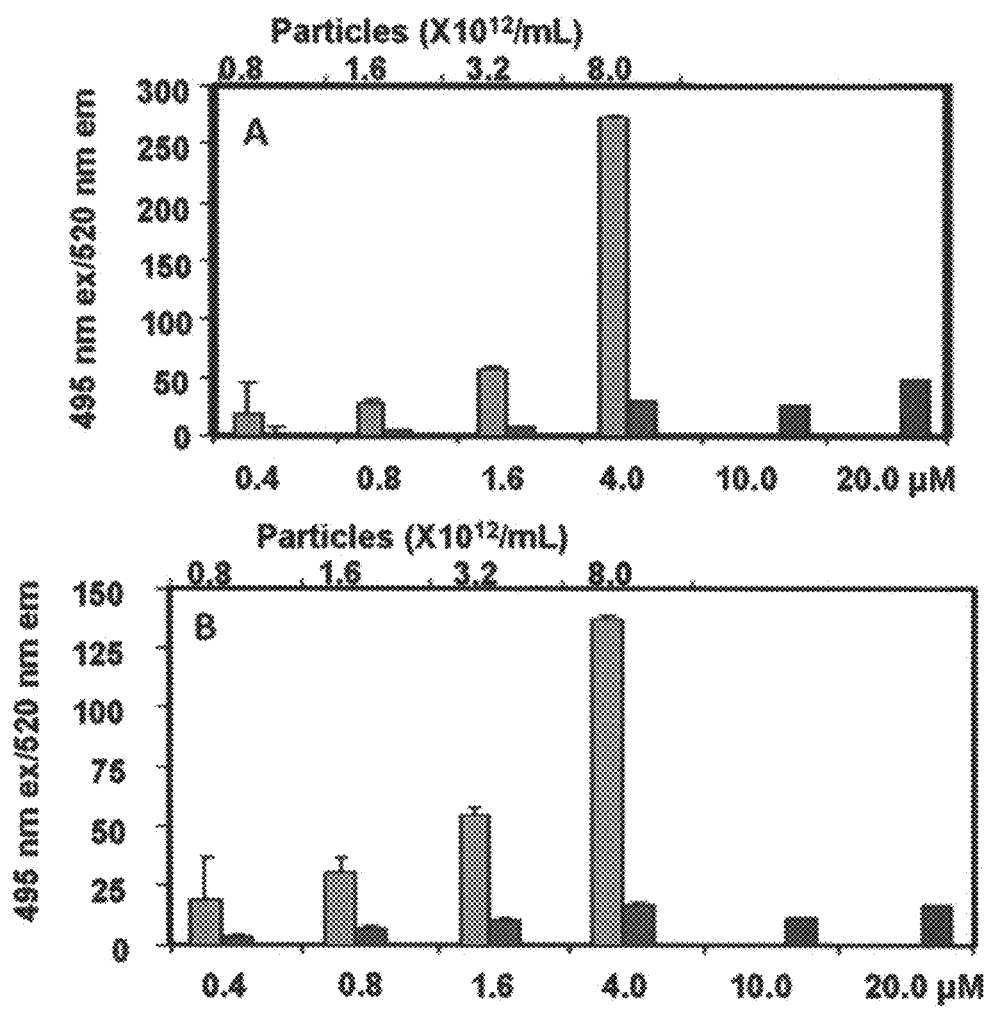
FIG. 5 shows the in vitro apoptotic effects of $Cer_{10}$-calcium phosphate nanoparticles (CPNPs) on (A) drug sensitive (MCF-7) and (B) drug resistant (MCF-7/ADR) breast adenocarcinoma cell lines. $Cer_{10}$-CPNPs, but not control CPNPs or $Cer_{10}$ in DMSO, induced robust caspase 3/7 activity, a measure of apoptosis in both drug sensitive and drug resistance cell lines. Values are mean±SEM for three independent experiments with each experiment replicated in triplicate. ±SEMs for $Cer_{10}$-CPNPs are too small to be depicted in the graph. The purple bar represents the CPNP while blue and green represent $Cer_{10}$ in CPNP and $Cer_{10}$ in DMSO respectively. The results for the CPNP (purple bar) are shown in the bar positioned to the right of the $Cer_{10}$ in CPNP (blue bar).

Consistent with our studies on melanoma cells, Cer-doped CPNP were also found highly effective for inducing apoptosis in breast cancer cell lines (FIG. 5, See Supporting information for experimental procedures). In fact, $Cer_{10}$-doped CPNP were effective in both drug-sensitive (MCF7) (FIG. 5A) and drug-resistant (MCF7/ADR, adriamycin resistant) (FIG. 5B) breast cancer cell models. This study provides the first demonstration that Cer administration can induce cellular apoptosis in a drug-resistant model of breast cancer. Specifically, 5-fold lower doses of $Cer_{10}$ in calcium phosphate nanocolloidal formulations elicited a 7-fold increase in caspase 3/7 activity (a marker of apoptosis) than $Cer_{10}$/

DMSO formulations. This is particularly exciting since Cer efficacy is often limited by P-glycoprotein multi-drug resistance receptors that metabolize Cer into less toxic metabolites. (Gouaze-Andersson, V.; Cabot, M. C. *Biochim Biophys Acta* 2006, 1758, (12), 2096-2103). Thus, Cer-encapsulated CPNP may offer a non-toxic nano-"solution" to treat drug resistant tumors. Again, there is a slight increase in apoptosis, as indicated by increasing caspase 3/7 activity, for the control formulations composed of amine-functionalized CPNP without Cer present. This finding is consistent with the studies on the melanoma cell culture, suggesting that there is an optimal, sub-toxic, threshold dosage of the CPNP for delivery of therapeutics. These in vitro breast cancer studies are the proof-of-concept studies that argue for continue investigation of the efficacy, biodistribution and cellular metabolism of Cer-doped CPNPs.

Figure 6:
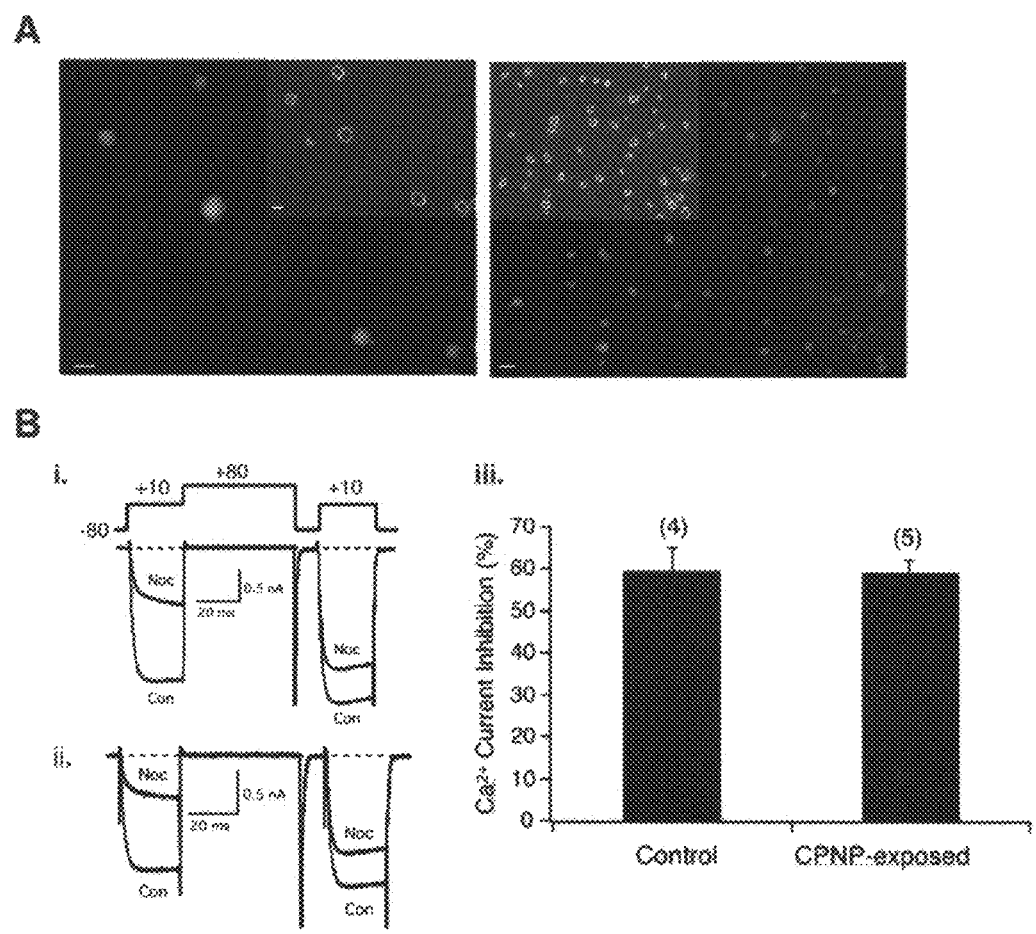
FIG. 6 shows the uptake of fluorescein-containing CPNP by rat sympathetic stellate ganglion (SG) neurons. (A) Fluorescence and phase contrast (insets) images of SG neurons following a 4 hr incubation with fluorescein-encapsulated CPNPs (8.1 ng/µL) at 37° C. SG neurons were imaged at 10× (right) and 20× (left) and fluorescence images were acquired with a filter set containing an excitation filter at 480 nm and an emission filter at 535 nm. The fluorescence images were pseudo-colored; scale bars, 20 µm. (B) i. Superimposed $Ca^{2+}$ current traces evoked with the 'double-pulse' voltage protocol (shown on top of i) in the absence (lower trace) or presence (upper trace) of nociceptin (1 µM) for a control (bi) and CPNP-exposed (ii) neuron. $Ca^{2+}$ currents were evoked every 10 s. (iii) Summary graph of mean (±SEM) $Ca^{2+}$ current inhibition produced by application of nociceptin in control and neurons incubated with fluorescein-containing CPNPs (8.1 ng/µL) for 3 hr. Inhibition was determined from the $Ca^{2+}$ current amplitude measured isochronally at 10 ms into the prepulse (+10 mV) in the absence or presence of nociceptin. Numbers in parenthesis indicate the number of experiments.

In the last set of experiments a cell culture model was chosen that could be particularly sensitive to exposure to the CPNP. Thus, we next examined whether fluorescent CPNP could be employed as imaging agents of sympathetic neurons, with little or no toxic effects. Acutely isolated adult rat stellate ganglion (SG) neurons were incubated with fluorescein-encapsulated CPNP. FIG. 6a shows fluorescence and phase contrast (inset image) images of SG neurons following 4 hr incubation with 8.1 ng/µL CPNP at 37° C. FIG. 6A shows that most of the neurons internalized the nanoparticles under these conditions. To verify the lack of CPNP-induced toxicity, the modulation of $Ca^{2+}$ currents by nociceptin (1 µM) was also examined. Nociceptin is the endogenous ligand for the opioid receptor-like 1 (ORL1) receptors expressed in SG neurons, and inhibits $Ca^{2+}$ channel currents in a voltage-dependent manner. The superimposed $Ca^{2+}$ current traces evoked every 10 sec with the 'double-pulse' voltage protocol (see Supporting Information) are given for control (FIG. 6Bi) and CPNP-treated (FIG. 6B ii) SG neurons. The upper trace in FIGS. 6Bi and 6Bii was obtained with nociceptin present while the lower trace was obtained without nociceptin. Application of nociceptin produced the typical voltage-dependent inhibition of $Ca^{2+}$ currents characterized by kinetic slowing in both groups of cells. No significant differences were observed in the magnitude of nociceptin-mediated $Ca^{2+}$ current inhibition (FIG. 6B iii) between the control and CPNP-exposed neurons. These results verify that exposure of SG neurons to CPNP did not lead to any significant changes in modulation of $Ca^{2+}$ channel currents implying little or no change in neuronal function and/or CPNP-induced toxicity following exposure to the nanoparticles.

This report demonstrates that CPNP are colloidally stable for extended times at physiological conditions and can be used to deliver fluorophores and lipophilic drugs for a variety of cell types. The metabolic pathways for $Ca^{2+}$ uptake and membrane transport are not perturbed and do not elicit acute toxicity in neural cells. Thus, CPNP have broad potential applicability as ex vivo and in vivo imaging agents as well as for drug delivery platforms. (Nano Lett., 2008, 8 (12), pp 4108-4115.; Nano Lett., 2008, 8 (12), pp 4116-4121; ACS Nano, 2008, 2 (10), pp 2075-2084). Validation of CPNP as highly efficacious, non-toxic, broadly-based, drug delivery platforms has been detailed in this study. The pH changes occurring during endocytosis leads to dissolution of CPNP and subsequent cytosolic or perinuclear release of encapsulated agents. (Nano Lett., 2008, 8 (12), pp 4108-4115.; Nano Lett., 2008, 8 (12), pp 4116-4121; ACS Nano, 2008, 2 (10), pp 2075-2084.). Thus, drugs with little or no physiological solubility can be delivered using the CPNP approach. Cer therapeutics provides an excellent demonstration of the efficacy of cellular delivery of a hydrophobic bioactive agent via the CPNP.

Despite the fact that $10^{14}$ amine functionalized CPNP/mL are systemically injected into animal models with minimal acute toxicity (data not shown), we are still concerned about chronic toxicology, especially given increasing cytotoxicity indicated by the MTS and caspase 3/7 assays with increasing particle number concentration for the control formulations. This observation is not unexpected, as for example, Sayes et al (Sayes, C. M.; Fortner, J. D.; Guo, W.; Lyon, D.; Boyd, A. D.; Ausman, K. D.; Tao, Y. J.; Sitharaman, B.; Wilson, L. J.; Highes, J. B.; West, J. L.; Colvin, V. L. *Nano Letters* 2004, 4, (10), 1881-1887) found that in vitro cytotoxicity of fullerenes was strongly associated with surface functionalization with cytotoxicity greatest for underivatized n-$C_{60}$, followed by $C_3$ and $Na^+{}_{2-3}[C_{60}O_{7-9}(OH)_{12-15}]^{(2-3)-}$, with $C_{60}(OH)_{24}$ having no cytotoxicity up to the solubility limit. Hoshino et al. (Hoshino, A.; Fujioka, K.; Oku, T.; Suga, M.; Sasaki, Y.; Ohta, T.; Yasuhara, M.; Suzuki, K.; Yamamoto, K. *Nano Letters* 2004, 4, (11), 2163-2169) found that amine-terminated quantum dot formulations gave one of the higher cytotoxicities as a function of surface speculation. However, variations in particle size distribution with surface functionality in Hoshino et al. (Hoshino, A.; Fujioka, K.; Oku, T.; Suga, M.; Sasaki, Y.; Ohta, T.; Yasuhara, M.; Suzuki, K.; Yamamoto, K. *Nano Letters* 2004, 4, (11), 2163-2169) give ambiguities regarding cytotoxicity as a function of surface groups. Our current studies are evaluating the effect of surface functionality on both cytotoxicity and biodistribution using citrate, PEG, and amine surface functionalization on the CPNPs.

Example 4

Calcium Phosphate Nanoparticle (CPNP) Preparation

CPNP manufacture uses the double reverse emulsion approach described by Adair et al. (Adair, J. H., Kumar, R., Antolino, N., Szepesi, C. J., Kimel, R. A., Rouse, S. M. In *Colloidal lessons learned for dispersion of nanosize particulate suspensions*, Proceedings of the World Academy of Ceramics, Faenza, Italy, 2005; Baumard, J. F., Ed. Techna Group Srl: Faenza, Italy, 2005; pp 93-145; Adair, J. H.; Li, T.; Kido, T.; Havey, K.; Moon, J.; Mecholsky, J.; Morrone, A.; Talham, D. R.; Ludwig, M. H.; Wang, L. *Materials Science & Engineering R-Reports* 1998, 23, (4-5), 139-242; Nano Lett., 2008, 8 (12), pp 4108-4115.; Nano Lett., 2008, 8 (12), pp 4116-4121; ACS Nano, 2008, 2 (10), pp 2075-2084). The general synthetic and dispersion scheme of organically-doped functionalized CPNP was adapted from a recently published calcium phosphate nanocomposite synthesis (Nano Lett., 2008, 8 (12), pp 4108-4115.; Nano Lett., 2008, 8 (12), pp 4116-4121; ACS Nano, 2008, 2 (10), pp 2075-2084). Two separate microemulsions were formed with a cyclohexane/nonylphenoxyl (glycolether)/water system. Typically, $10^{-2}$ M $CaCl_2$ (aq) was added to the first microemulsion and $6 \times 10^{-3}$ M $NaH_2PO_4$ (aq) (phosphate buffered to pH 7.4) was added to create the second microemulsion ($Ca^{2+}:PO_4^{3-}$ is 1.67, corresponding to the ratio found in hydroxyapatite). The dopant (in most cases an organic fluoroprobe and/or a therapeutic agent) was added to one of the microemulsions based on charge considerations. However, the dopant concentration should not be any greater than about a 1:100 molar ratio with $Ca^{2+}$ if the dopant contains $Ca^{2+}$-binding groups (e.g., $-SO_3$, $-COOH$, - and $PO_3$). Significant concentrations of a $Ca^{2+}$-binding species can inhibit precipitation of the calcium phosphate. The microemulsions were equilibrated for 3-5 minutes before being combined to form a microemulsion mixture. The combined microemulsion was then allowed to undergo micellular exchange for approximately 2 minutes, during which time doped calcium phosphate nanoparticles (typically 30 nm) were precipitated within the reverse micelle. A dispersant, typically 10 w/w 3-amino-propyltriethoxysilane (relative to the mass of the calcium phosphate) was then added to the microemulsion mixture. After 2 minutes of equilibration, a homogeneous solution was created by dispersing the amphiphilic molecules of the micelles in ethanol. Carboxylate-terminated or PEG-terminated CPNP can also be prepared. (Nano Lett., 2008, 8 (12), pp 4108-4115.; Nano Lett., 2008, 8 (12), pp 4116-4121; ACS Nano, 2008, 2 (10), pp 2075-2084).

Following micellar disruption, particles were immediately washed using an affinity/size-exclusion HPLC washing procedure. (Adair, J. H., Kumar, R., Antolino, N., Szepesi, C. J., Kimel, R. A., Rouse, S. M. In *Colloidal lessons learned for dispersion of nanosize particulate suspensions*, Proceedings of the World Academy of Ceramics, Faenza, Italy, 2005; Baumard, J. F., Ed. Techna Group SrI: Faenza, Italy, 2005; pp 93-145; Nano Lett., 2008, 8 (12), pp 4108-4115.; Nano Lett., 2008, 8 (12), pp 4116-4121; ACS Nano, 2008, 2 (10), pp 2075-2084; Wang, J.; White, W. B.; Adair, J. H. *J Phys Chem B Condens Matter Mater Surf Interfaces Biophys* 2006, 110, (10), 4679-85). The particle solution, containing functionalized, doped nanoparticles was loaded onto a chromatography column containing silica micro-spheres (Stellar Phases Inc., ~20 μm diameter, 6 nm pore size) functionalized with 1 weight percent 3-amino-propyltriethoxysilane. The nanoparticles were washed with ethanol (adjusted to pH 7.4) and eluted using a 7:3 ethanol/water ratio (also adjusted to pH 7.4). The ethanol suppressed calcium phosphate solubility during elution, which minimized impact of pH changes through the HPLC column. In addition, ethanol maintained the calcium phosphate nanoparticles in a sterile state. Eluent was monitored using UV-Vis absorption (Shimadzu SPD-6A, Shimadzu Scientific, Kyoto, Japan) appropriate for maximum absorbance wavelength of the encapsulated organic. The wash removed all detectable residual cyclohexane (typically less than 15 ppm by GC-MS), amphiphilic molecules and free dopant. Resulting calcium phosphate formulations were subsequently diluted into phosphate buffered saline (pH 7.4, 0.14M NaCl and 0.01M KCl) or cell culture media as appropriate for particular cellular assays.

Example 5

Characterization of Calcium Phosphate Nanoparticles

The morphology and size of nanoparticles were characterized using transmission electron microscopy (TEM) (JEOL 2010F, Tokyo, Japan) and quasi-elastic light scattering (QELS) (Nano S Zetasizer, Malvern Instruments Ltd., UK). Fluorescence spectra were recorded using the F-4010 Fluorescence Spectrophotometer (Hitachi, Ltd., Japan). X-ray diffraction confirmed that the only solid phase present was amorphous calcium phosphate. Additionally, zeta potential (ZP) determinations were recorded using electrophoretic light scattering (ZetaPALS, Brookhaven Instrument Corp., Holtsville, N.Y.) to verify positive surface charge from amine surface groups. Nanoparticle suspension pH was monitored during synthesis and characterization using a Sentron probe (Argus IP 65 ISFET, Sentron Inc., The Netherlands), which was calibrated against standard aqueous buffer solutions. Density measurements were made using an acoustic, handheld density meter to determine the solids loading of the washed nanocomposite suspensions (Anton Paar, DMA 35N, Graz, Austria). Loss on ignition at 105° C. was also used to confirm the solid concentration.

Example 6

Melanoma Cell Imaging and Cytotoxicity Assays $7.5 \times 10^3$ UACC 903 melanoma cells were plated in each well of six well plates containing glass cover slips. Cells were allowed to attach for 4 hrs, washed with medium, and incubated for 24 hrs. DMEM containing 10% fetal bovine serum was then replaced with media supplemented with $Cer_{10}$ (equivalent to a 10 μM final concentration) and Rhodamine WT encapsulated within CPNP ($Cer_{10}$-CPNP) or nanoparticles containing fluorophore alone (control CPNP) at approximately $2 \times 10^{13}$ particles concentration for 24 hrs. Cover slips were rinsed with PBS and adherent cells fixed in 4% paraformaldehyde for 30 min at room temperature. The cover slips were then washed 3 times with PBS, mounted on slides with Vectashield mounting media containing DAPI (Vector Laboratories, Burlingame, Calif.) and sealed with clear nail polish. Two color fluorescence images were recorded with a Nikon Eclipse 600 Microscope. The images with the DAPI were obtained with the use of a cutoff filter between the maximum excitation and emission wavelengths at 345 nm and 455 nm, respectively. Fluorescence images with the Rh-WT encapsulated CPNP at 10 ng/μL were obtained with a cutoff filter between the maximum excitation and emission wavelengths at 560 nm and 580 nm, respectively.

The antiproliferative effect of $Cer_{10}$ was measured on cultured melanoma cells, by plating $5 \times 10^3$ UACC 903 cells per well in 96-well plates and allowing cell attachment for 24 hrs. The following day, the cells were treated with growth media containing $Cer_{10}$-CPNP, control CPNP, or 0.3 volume percent ethanol (vehicle) at the indicated doses for 24 hrs. In these experiments, dilutions were prepared to deliver $2 \times 10^{13}$ to $0.8 \times 10^{13}$ particles, which in the Cer-doped CPNP corresponded to 10 to 4 μM $Cer_{10}$, respectively. Following 24 hrs of treatment, cell cytotoxicity/viability was assessed using the MTS (CellTiter 96 Aq$_{ueous}$ Non Radioactive Cell Proliferation Assay kit, Promega, Madison, Wis.) assay according to manufacturer's instructions. The assay employs a tetrazolium compound that is bio-reduced by viable cells into a soluble formazan product, which can be measured by its absorbance at 490 nm. Quantity of formazan product as measured by absorbance is directly proportional to the number of viable cells in the culture.

Example 7

Breast Adenocarcinoma Apoptosis Assays

Human MCF-7 breast adenocarcinoma cells and the adriamycin resistant MCF-7-ADR(NCl-AdrR) were grown at 37° C. in RPMI 1640 medium supplemented with 10% fetal bovine serum (FBS). MCF-7 and MCF-7-ADR cells were seeded to a density of $6 \times 10^3$ cells/well and grown for 48 hrs in culture medium containing 10% FBS. Cells were then treated with $Cer_{10}$-CPNP or control CPNP for 24 hrs in media containing 1% fetal bovine serum. Caspase-3/7 enzymatic activity levels were then measured using the Apo-ONE Homogenous Caspase-3/7 Assay (Promega) and performed following the instructions of the manufacturer. The kit provides a caspase-3/7 substrate and Rhodamine 110, which is cleaved by enzymatically active caspase-3/7 resulting in a fluorogenic cleavage product.

Example 8

Stellate Ganglion (SG) Neuron Isolation, Imaging, and $Ca^{2+}$ Current Recording Stellate ganglion (SG) neurons from adult male Wistar rats (175-225 g) were prepared using the method described previously. (Ruiz-Velasco V, P. H. L., Fuller B. C. and Sumner A. D. *J. Pharm. Exp. Ther.* 2005, 314, 987-994). The experiments carried out were approved by the Institutional Animal Care and Use Committee of Penn State College of Medicine. Neurons were enzymatically dissociated as previously described. (Ruiz-Velasco V, P. H. L., Fuller B. C. and Sumner A. D. *J. Pharm. Exp. Ther.* 2005, 314, 987-994). The isolated neurons were resuspended in Minimal Essential Medium (MEM), supplemented with 10% fetal calf serum, 1% glutamine and 1% penicillin-streptomycin solution (Invitrogen, Carlsbad, Calif.). The dissociated neurons were plated onto 35 mm polystyrene tissue culture plates coated with poly-L-lysine and stored overnight in a humidified incubator (95% air and 5% $CO_2$) at 37° C. Thereafter, SG neurons were incubated with calcium phosphate nanoparticles (50 μL of the as-received 240 ppm particles were diluted into 1000 μL MEM media for a final concentration of 8.1 ng/μL fluorescein nanoparticles per mL of MEM) for 3 to 4 hrs at 37° C.

Fluorescence images were obtained with a Nikon TE2000U (Nikon) microscope employing a 20× objective, the X-Cite 120 (EXFO Life Sciences Group, Ontario, Canada) for illumination, and acquired with an Orca-ER 1394 digital CCD camera (Hamamatsu Photonics K. K., Japan) and IPLab software (Scanalytics Inc., Fairfax, Va.). Fluorescence images of fluorescein-labeled neurons were obtained with a filter set (B-2E/C; Nikon) containing an excitation filter at 480±15 nm, a dichroic beam splitter of 505 nm (LP) and an emission filter at 535±20 nm.

$Ca^{2+}$ currents were recorded at room temperature (21-24° C.) employing the whole-cell patch-clamp technique. The recording pipettes were pulled from borosilicate glass capillaries (Corning 7052; Garner Glass, Claremont, Calif.) on a Flaming-Brown (P-97) micropipette puller (Sutter Instrument Co., Novato, Calif.), coated with Sylgard (Dow Corning, Midland, Mich.) and fire polished with a microforge. SG whole-cell $Ca^{2+}$ currents were acquired with a patch-clamp amplifier (Axopatch 200B, Axon Instruments, Foster City, Calif.), analog filtered at 5 kHz (−3 dB; 4-pole low pass Bessel filter) and digitized employing custom designed software (S4) on a PowerMacG4 computer (Apple Computer, Cupertino, Calif.) equipped with an 16-bit analog-to-digital converter board (ITC 16, Instrutech Corp., Port Wash., N.Y.). The cell's series resistance (80-85%) and membrane capacitance were electronically compensated. Data analysis was performed with Igor Pro (Lake Oswego, Oreg.) software packages. Summary graph and current traces were produced with the Igor Pro and Canvas 8.0 (Deneba Software, Miami, Fla.) software packages.

The pipette solution contained (in mM): 120 N-methyl-D-glucamine, 20-tetraethylammonium hydroxide (TEAOH), 11 EGTA, 10 HEPES, 1 $CaCl_2$, 4 Mg-ATP, 0.3 $Na_2GTP$, and 14 tris creatine phosphate. The pH was adjusted to pH 7.2 with methanesulfonic acid and the osmolality was 297 mosmol/kg. The external solution consisted of (in mM) 145 TEAOH, 140 methanesulfonic acid, 10 HEPES, 15 glucose, 10 $CaCl_2$, and 0.0003 tetrodotoxin. The pH was adjusted to pH 7.4 with TEAOH and the osmolality was 323 mosmol/kg. Stock solution of nociceptin (Tocris Cookson, Ellisville, Mo.) was prepared in $H_2O$ and diluted in the external solution to its final concentration (1 μM) prior to use.

Example 9

Encapsulation of Organic Molecules in Calcium Phosphate Nanocomposite Particles for Intracellular Imaging and Drug Delivery Encapsulation of imaging agents and drugs in calcium phosphate nanoparticles (CPNPs) has the potential to overcome the low efficiency and marginal safety of drug delivery to cells and tumors. The objectives of this study were to develop a calcium-phosphate nanoparticle encapsulation system for organic dyes and therapeutic drugs such that advanced fluorescence methods could be used to assess the efficiency of drug delivery and possible mechanisms of nanoparticle bioabsorption. Highly concentrated calcium phosphate nanoparticles (CPNPs) encapsulating a variety of organic fluorophores were successfully synthesized. Well dispersed CPNPs encapsulating Cy3 exhibited nearly a five fold increase in fluorescence quantum yield when compared to the free dye in PBS. FCS diffusion data and cell staining were utilized to show pH dependent dissolution of the particles and cellular uptake. Furthermore, an experimental hydrophobic cell growth arrester, ceramide, was successfully delivered in vitro to human vascular smooth muscle cells via encapsulation in CPNPs. These studies demonstrate that CPNPs are effective carriers of dyes and drugs for bioimaging and potentially for therapeutic intervention.

Encasement of fluorescent dyes and other organic molecules in nanoparticulate systems is of significant importance in the fields of drug delivery and biological imaging. (Vasir, J. K.; Labhestwar, V. *Advanced Drug Delivery Reviews* 2007, 59, 718-728; Ow, H.; Larson, D. R.; Srivastava, M.; Baird, B. A.; Webb, W. W.; Wiesner, U. *Nano Letters* 2005, 5, (1), 113-117; Jin, S.; Ye, K. *Biotechnology Progress* 2007, 23, 32-41; Xu, Z. P.; Zeng, Q. H.; Lu, G. Q.; Yu, A. B. *Chemical Engineering Science* 2006, 61, 1027-1040; Bisht, S., Bhakta, Gajadhar, Mitra, Susmita, Maitra, Amarnath. *International Journal of Pharmaceutics* 2004, 288, 157-168; Yao, G.; Wang, L.; Wu, Y.; Smith, J.; Xu, J.; Zhao, W.; Lee, E.; Tan, W. *Analytical Bioanalytical Chemistry* 2006, 385, 518-524 Welzel, T.; Radtke, I.; Meyer-Zaika, W.; Heumann, R.; Epple, M. *Journal of Materials Chemistry* 2004, 14, 2213-2217). Approaches to capture organic molecules in nanoparticles is an area of intense research addressing many schemes ranging from polymeric systems, (Panyam, J.; Labhestwar, V. *Advanced Drug Delivery Reviews* 2003, 55, 329-347; Park, J. S.; Han, T. H.; Lee, K. Y.; Han, S. S.; Hwang, J. J.; Moon, D. H.; Kim, S. Y.; Cho), and liposomes, (Stover, T. C.; Sharma, A.; Robertson, G. P.; Kester, M. *Clinical Cancer Research* 2005, 11, (9), 3465-3474) to inorganic oxides. (Ow, H.; Larson, D. R.; Srivastava, M.; Baird, B. A.; Webb, W. W.; Wiesner, U. *Nano Letters* 2005, 5, (1), 113-117; Xu, Z. P.; Zeng, Q. H.; Lu, G. Q.; Yu, A. B. *Chemical Engineering Science* 2006, 61, 1027-1040; Bisht, S., Bhakta, Gajadhar, Mitra, Susmita, Maitra, Amarnath. *International Journal of Pharmaceutics* 2004, 288, 157-168; Welzel, T.; Radtke, I.; Meyer-Zaika, W.; Heumann, R.; Epple, M. *Journal of Materials Chemistry* 2004, 14, 2213-2217; Bagwe, R., P.; Yang, Chaoyong; Hilliard, Lisa R.; Tan, Weihong. *American Chemical Society—Langmuir* 2005, 20, 8336-8342; Bele, M.; Siiman, O.; Matijevic, E. *Journal of Colloid and Interface Science* 2002, 254, 274-282; Fuller, J. E.; Zugates, G. T.;

Ferreira, L. S.; Ow, H. S.; Nguyen, N. N.; Wiesner, U. B.; Langer, R. S. *Biomaterials* 2008, 29, 1526-1532). However, many of these systems have significant shortcomings that limit their usefulness as bioimaging agents or as drug delivery vehicles. For example, it has been shown in polymeric nanoparticles for cellular uptake that endocytosis may be immediately followed by exocytosis once the concentration gradient of particles outside the cell is removed. (Panyam, J.; Labhestwar, V. *Advanced Drug Delivery Reviews* 2003, 55, 329-347). Exocytosis may, presumably, result from insoluble solid and amorphous nanoparticle systems, and will limit their utility as drug delivery agents. (Park, J. S.; Han, T. H.; Lee, K. Y.; Han, S. S.; Hwang, J. J.; Moon, D. H.; Kim, S. Y.; Cho, Y. W. *Journal of Controlled Release* 2006, 115, 37-45; Chithrani, B. D.; Chan, W. C. W. *Nano Letters* 2007, 7, (6), 1542-1550). Additionally, many of the systems are difficult and time consuming to synthesize. (Tan, W. B.; Zhang, Y. *Journal of Biomedical Materials Research, Part A* 2005, 75A, (1), 56-62; Joshi, H. M.; Bhumkar, D. R.; Joshi, K.; Pokharkar, V.; Sastry, M. *Langmuir* 2006, 22, (1), 300-305; Dhanikula, R. S.; Hildgen, P. *Bioconjugate Chemistry* 2006, 17, 29-41). This is particularly true for metallic and semiconductor nanoparticles, which often require post-preparative ligand exchanges for functionality, (Tan, W. B.; Zhang, Y. *Journal of Biomedical Materials Research, Part A* 2005, 75A, (1), 56-62; Joshi, H. M.; Bhumkar, D. R.; Joshi, K.; Pokharkar, V.; Sastry, M. *Langmuir* 2006, 22, (1), 300-305) and for dendrimers, which can take many hours or even days to prepare. (Dhanikula, R. S.; Hildgen, P. *Bioconjugate Chemistry* 2006, 17, 29-41). Nanometer size particles, in particular, are often difficult to disperse, especially at high ionic strength and in the presence of proteins encountered in physiological fluids, such as in the blood stream. (Adair, J. H.; Kumar, R.; Antolino, N.; Szepesi, C. J.; Kimel, R. A.; Rouse, S. M., Colloidal Lessons Learned for Dispersion of Nanosize Particulate Suspensions. In *Lessons in Nanotechnology from Traditional and Advanced Ceramics*, Baumard, J. F., Ed. Techna Group: 2005; pp 93-145).

Several inherent properties of calcium phosphate (CP) underscore the potential of this system for organic encasement with respect to drug delivery and bioimaging. CP is found throughout the body in the form of amorphous calcium phosphate (ACP) as well as crystalline hydroxyapatite (HAP), the major component of bone and tooth enamel. Additionally, both $Ca^{2+}$ and $PO_4^{3-}$ are found in relatively high concentrations at typically 1 to 5 mM in the bloodstream. (Wang, S.; McDonnell, E. H.; Sedor, F. A.; Toffaletti, J. G. *Archives of Pathology and Laboratory Medicine* 2002, 126, 947-950; Alberts, B.; Johnson, A.; Lewis, J.; Raff, M.; Roberts, K.; Walter, P., *Molecular Biology of The Cell*. Fourth ed.; Garland Science New York, 2002; Coe, F. L., Favus, M. J., Pak, C. Y. C., Parks, J. H., Preminger, G. M., *Kidney Stones: Medical and Surgical Management*. Lippincott-Raven Publishers: Philadelphia, 1996; Israelachvili, J., *Intermolecular and Surface Forces*. Second edition ed.; Academic Press: London, 1992). This natural occurrence of CP is one of the primary advantages over other synthetic drug delivery systems. As a biomineral, CP safely biodistributes, with dissolved material regulated via the kidneys. CP is relatively insoluble at physiological pH, but has increasing solubility in the acidic environments that can occur in the body, (Tung, M. S., Calcium Phosphates: Structure, Composition, Solubility, and Stability. In *Calcium Phosphates in Biological and Industrial Systems*, Amjad, Z., Ed. Kluwer Academic Publishers: Boston, 1998; pp 1-19) such as in endo-lysosomes (Panyam, J.; Labhestwar, V. *Advanced Drug Delivery Reviews* 2003, 55, 329-347; Tycko, B.; Maxfield, F. R. *Cell* 1982, 26, 643-651) or around solid tumors. (Stubbs, M.; McSheehy, P. M. J.; Griffiths, J. R.; Bashford, C. L. *Molecular Medicine Today* 2000, 6, 15-19). This pH dependent solubility provides an advantage in the delivery of multifunctional drugs, fluorescent dyes, or other organic cargo, to a cell or organelle. Fluorescent dyes can be used as a tracking device for the state of the particle, and give an indication of cargo delivery, while the CP matrix can serve to protect the cargo in vivo until it has reached the destination.

Because the formation of CP is a relatively straight-forward precipitation reaction, encasement of the cargo molecules requires only that the molecule of interest be present during the particle formation. Additionally, CP is an easily substituted matrix, and often forms amorphous particles under typical reaction conditions. (Adair, J. H.; Kumar, R.; Antolino, N.; Szepesi, C. J.; Kimel, R. A.; Rouse, S. M., Colloidal Lessons Learned for Dispersion of Nanosize Particulate Suspensions. In *Lessons in Nanotechnology from Traditional and Advanced Ceramics*, Baumard, J. F., Ed. Techna Group: 2005; pp 93-145; Tung, M. S., Calcium Phosphates: Structure, Composition, Solubility, and Stability. In *Calcium Phosphates in Biological and Industrial Systems*, Amjad, Z., Ed. Kluwer Academic Publishers: Boston, 1998; pp 1-19). This property permits the inclusion of a broad variety of substitutions such as organic fluorophores or other low molecular weight molecules.

A wide variety of calcium phosphate precipitation schemes exist, (Bisht, S., Bhakta, Gajadhar, Mitra, Susmita, Maitra, Amarnath. *International Journal of Pharmaceutics* 2004, 288, 157-168; Welzel, T.; Radtke, I.; Meyer-Zaika, W.; Heumann, R.; Epple, M. *Journal of Materials Chemistry* 2004, 14, 2213-2217; Tang, R.; Wang, L.; Nancollas, G. H. *Journal of Materials Chemistry* 2004, 14, 2341-2346; Sadasivan, S.; Khushalani, D.; Mann, S. *Chemistry of Materials* 2005, 17, 2765-2770; Sarda, S.; Heughebaert, M.; Lebugle, A. *Chemistry of Materials* 1999, 11, (2722-2727)) varying from a controlled addition of a phosphate solution to a calcium solution, (Welzel, T.; Radtke, I.; Meyer-Zaika, W.; Heumann, R.; Epple, M. *Journal of Materials Chemistry* 2004, 14, 2213-2217) to the use of double microemulsions as templates for particle size. (Bisht, S., Bhakta, Gajadhar, Mitra, Susmita, Maitra, Amarnath. *International Journal of Pharmaceutics* 2004, 288, 157-168; Sadasivan, S.; Khushalani, D.; Mann, S. *Chemistry of Materials* 2005, 17, 2765-2770; Sarda, S.; Heughebaert, M.; Lebugle, A. *Chemistry of Materials* 1999, 11, (2722-2727)). However, an organic capture based approach is not widely utilized. (Bisht, S., Bhakta, Gajadhar, Mitra, Susmita, Maitra, Amarnath. *International Journal of Pharmaceutics* 2004, 288, 157-168; Welzel, T.; Radtke, I.; Meyer-Zaika, W.; Heumann, R.; Epple, M. *Journal of Materials Chemistry* 2004, 14, 2213-2217). Furthermore, none of these schemes produce colloidally stable particles with diameters under 100 nm, and significant agglomeration is usually encountered. (Bisht, S., Bhakta, Gajadhar, Mitra, Susmita, Maitra, Amarnath. *International Journal of Pharmaceutics* 2004, 288, 157-168; Welzel, T.; Radtke, I.; Meyer-Zaika, W.; Heumann, R.; Epple, M. *Journal of Materials Chemistry* 2004, 14, 2213-2217).

A critical issue seldom reported in detail is the laundering technique(s) used to remove residual precursor contaminants. This report documents the first demonstration of the preparation of well dispersed, organically doped, nanoscale calcium phosphate particles. Maintaining well-dispersed nanoparticles is a challenge that limits many colloidal systems. (Adair, J. H.; Kumar, R.; Antolino, N.; Szepesi, C. J.; Kimel, R. A.; Rouse, S. M., Colloidal Lessons Learned for Dispersion of Nanosize Particulate Suspensions. In *Lessons in*

Nanotechnology from Traditional and Advanced Ceramics, Baumard, J. F., Ed. Techna Group: 2005; pp 93-145). Despite the importance of maintaining dispersion, many existing post-synthesis laundering schemes produce agglomerates. (Bisht, S., Bhakta, Gajadhar, Mitra, Susmita, Maitra, Amarnath. *International Journal of Pharmaceutics* 2004, 288, 157-168; Wang, J.; White, W. B.; Adair, J. H. *Journal of Physical Chemistry B* 2006, 110, 4679-4685). Dialysis has been used to remove spectator species from calcium phosphate particle suspensions. This approach, however, leads to substantial particle agglomeration. (Bisht, S., Bhakta, Gajadhar, Mitra, Susmita, Maitra, Amarnath. *International Journal of Pharmaceutics* 2004, 288, 157-168). Wang et al. investigated several other laundering schemes for silica nanocomposite colloids, which included centrifugation, filtration, Soxhlet extraction and van der Waals chromatography (via high performance liquid chromatography, HPLC). (Wang, J.; White, W. B.; Adair, J. H. *Journal of Physical Chemistry B* 2006, 110, 4679-4685). Only the van der Waals chromatography (vdW-HPLC laundering) produced stable, non-agglomerated, concentrated particles.

Figure 7:
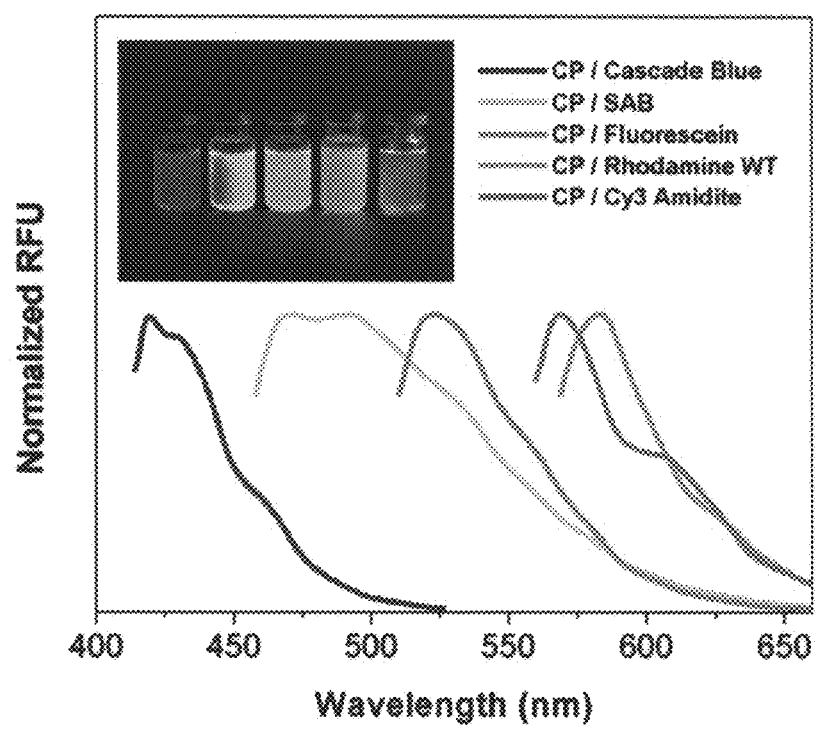
FIG. 7 is a photograph showing a range of encapsulated fluorophores that spans the visible region. The spectra show Cascade Blue© (dark blue), 10-(3-Sulfopropyl) Acridinium Betaine (SAB; light blue), fluorescein (green), rhodamine WT (orange), and Cy3 amidite (magenta) encapsulated in calcium phosphate nanoparticles. The inset is a photograph taken under UV lamp excitation displaying the fluorescence of encapsulated fluorophores. From left to right: Cascade Blue©, SAB, fluorescein, rhodamine WT, and Cy3 Amidite.

We have developed a general method for encapsulating small organic molecules in well dispersed calcium phosphate nanoparticles, which utilizes the vdW-HPLC scheme (Wang, J.; White, W. B.; Adair, J. H. *Journal of Physical Chemistry B* 2006, 110, 4679-4685) in modified form to launder the particles while maintaining dispersion. Herein we report the capture of a range of organic dyes (Cascade Blue©, 10-(3-sulfopropyl) acridinium betaine or SAB, fluorescein sodium salt, rhodamine WT, and Cy3 amidite), as a general proof of concept study for small molecule encasement. FIG. 7 displays some of the fluorescent dyes that have been successfully encapsulated using this method, and demonstrates the ability to encapsulate a wide variety of small molecules. These dyes encompass a range of solubility in water, from very soluble (>40 mg/mL for fluorescein sodium salt) to relatively insoluble (<0.05 mg/mL for Cy3 amidite), and include a variety of functional groups. We show enhanced fluorescence emission for use in cellular imaging as well as dissolution of the particles at low pH. We utilize these properties for simultaneous fluorescence imaging of and drug delivery to vascular smooth muscle cells.

The general synthesis scheme of organically-doped, functionalized calcium phosphate nanoparticles (CP-NPs) was adapted from recently published silica syntheses. (Wang, J.; White, W. B.; Adair, J. H. *Journal of Physical Chemistry B* 2006, 110, 4679-4685; Li, T.; Moon, J.; Morrone, A. A.; Mecholsky, J. J.; Talham, D. R.; Adair, J. H. *Langmuir* 1999, 15, 4328-4334). For the CPNP synthesis, two separate microemulsions (1 and 2) are formed with a cyclohexane/Igepal CO-520/water system. The molar ratio of water to surfactant is 4. Typically, 650 μL of $1\times10^{-2}$ M $CaCl_2$ in $CO_2$-free deionized water is added to 14 mL of a 29 volume percent solution of Igepal CO-520 in cyclohexane to form Microemulsion 1. Similarly, 650 μL of $6\times10^{-3}$ M disodium phosphate with $8\times10^4$ M disodium silicate in $CO_2$-free dionized water (pH 7.4) is added to 14 mL of a 29 volume percent solution of Igepal CO-520 in cyclohexane to form Microemulsion 2. Disodium silicate is present to act as a nucleation agent for the calcium phosphate. (Adair, J. H.; Nagira, T.; Brown, C. M.; Khan, S. R.; Thomas, W. C. J., Heterogeneous Deposition of Calcium Phosphates at the Silicon (Hydrous) Oxide-Water Interface. In *Urolithiasis* 2, Ryall, R.; Bias, R.; Marshall, V. R.; Rofe, A. M.; Smith, L. H.; Walker, V. R., Eds. Plenum Press: New York, 1995; pp 181-187). The addition of the aqueous solution to the cyclohexane/Igepal CO-520 solution forms a self-assembled, reverse micelle suspension. The dopant is added to one of the microemulsions based on electrostatic and stability constant considerations. For instance, negatively charged molecules, such as fluorescein and Cy3 amidite, are added to Microemulsion 2 (with the phosphate solution). This procedure is used to prevent particle nucleation and growth inhibition that can occur due to calcium binding with the carboxylate- or sulfonate-groups present on many fluorophores. Water soluble organic dyes (such as fluorescein sodium salt and rhodamine WT) are mixed with the aqueous solution before addition into the micelle. Dyes that are insoluble in water can be added in an ethanol or ethanol-water solution after the microemulsion is formed. This report will mainly focus on details of Cy3 amidite doped CP, where 1 mL of $1\times10^{-3}$ M Cy3 in neat ethanol is added to Microemulsion 2. The individual microemulsions are allowed to equilibrate for 3 minutes before 1 and 2 are mixed to form Microemulsion 3. Microemulsion 3 is allowed to undergo micellar exchange for 2 minutes, during which time doped CP nanoparticles precipitate in the micelles. A dispersant is then added to Microemulsion 3. For carboxy-functionalized particles, 225 μL of a $1\times10^{-3}$ M sodium citrate is added and allowed to react for 10 minutes. For amine functionalized particles, 125 μL of $4\times10^{-2}$ M aminopropyltriethoxysilane (APTES) solution in a 95:5:1 ethanol:water:acetic acid mixture is added and allowed to react for 24 hours. After adding the dispersant, the reverse micelles are dissolved with 50 mL of pH adjusted ethanol (pH=7) before laundering via the vdW-HPLC.

The difference between the relatively strong long range van der Waals attraction associated with condensed matter (i.e. two solid particles interacting with one another) as opposed to the short range, and weaker, van der Waals interaction between uncharged molecules and solid surfaces, (Israelachvili, J., *Intermolecular and Surface Forces*. Second edition ed.; Academic Press: London, 1992) is the basis for the vdW-HPLC approach to nanoparticle laundering. Control over the electrostatic surface charges with the mobile phase solvent provides the ability to either inhibit or promote surface charging with relatively non-polar and polar solvents, respectively. Inhibiting the surface charging with non-polar solvents, such as neat ethanol, permits the van der Waals attractive forces to dominate, and reversible particle deposition onto the stationary phase is achieved. By maintaining this non-polar environment, the weakly attracted organic molecules, such as amphiphiles and free dye, can be flushed through the column while the particles remain adhered. Shifting to a more polar solvent, in this case 70:30 ethanol:water by volume, increases the surface charging on both the stationary phase as well as the nano colloids and provides significant electrosteric repulsion to overcome the van der Waals attractive forces, allowing the particles to break off of the column and be eluted. The end result is a concentrated solution of well-dispersed nanocolloids.

Specifically, for the CPNP system the vdW-HPLC procedure is as follows: the unwashed, as-prepared nanoparticle suspension is loaded onto an appropriately functionalized column after the micelles have been dissolved with ethanol; the free organic is laundered using ethanol as the eluent; finally, the particles are eluted using 70:30 ethanol:water by volume. To launder the particles without inducing aggregation, stationary phase must be functionalized such that the particles will associate with, but not irreversibly aggregate to, the media. In the case of the amine terminated particles, the stationary phase consists of 1 w/o APTES treated 20 μm silica spheres with 6.5 nm pores. Alternately, citrate functionalized particles are washed on the as-received, negatively charged silica microspheres.

The sample, which is approximately 25 volume percent cyclohexane in ethanol after micellar dissolution, is loaded onto the silica HPLC column. The CPNP colloids adhere to the silica media because negligible surface charge is present in the low dielectric media. Thus, the relatively large van der Waals attraction of the particles to the silica media in the HPLC column leads to adhesion of the nanoparticles. Subsequent washing with neat ethanol reduces the surfactant concentration from 0.2 M Igepal CO-520 to below $1 \times 10^{-3}$ M after a single pass through the column. Virtually all of the free organic dye and the cyclohexane are removed and are below the limits of detection via fluorescence correlation spectroscopy (FCS) and GC-MS, respectively. This leaves the now laundered CPNP colloids adhered to the column.

During the washing step, the dye content is monitored at the characteristic absorption wavelength (for Cy3 this is 532 nm). The ethanol washing continues until the detector reaches baseline indicating removal of the unencapsulated dye. The particles, which remain on the column due to van der Waals attraction, are then eluted with a 70:30 ethanol:water solution with $5 \times 10^{-4}$ M NaCl (prepared with $CO_2$-free deionized water, pH=7) which provides enough charge for electrostatic repulsion to dominate the nanocolloid-silica media interaction energies. The first major peak is collected. The precursor and HLPC solutions are prepared with $CO_2$-free deionized water to avoid carbonate contamination in the CPNPs. All solution pH measurements are performed using a Sentron ISFET pH probe calibrated against aqueous standards.

For PEG surface functionalization, 0.5 mg of ethyl-3-(3-dimethylaminopropyl) carbodiimide (EDCI) and 1 mg of methoxyPEG-amine (mPEG-amine, 20 kDa) in water are added to 1 mL of laundered citrate functionalized CP nanoparticle suspension. (Sharma, R. K.; Das, S.; Maitra, A. *Journal of Colloid and Interface Science* 2004, 277, 324-346). The particles are reacted for 18 hours at 40° C. under continuous stirring to form amide linkages between the particles and the mPEG-amine. The PEGylated particles are then dialyzed to remove the excess EDCI and unreacted methoxyPEG-amine. The dialyzed particles remain well dispersed, and agglomeration is not induced at this step.

Figure 8:
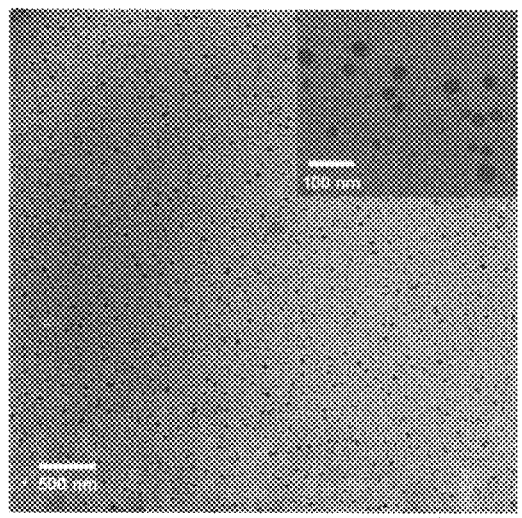
FIG. 8 is a TEM micrograph that shows well dispersed spherical particles on a carbon film grid. The inset shows the morphology in detail.

Transmission electron microscopy (TEM) images were taken on a Phillips 420 at 120 keV, and the particles were dropped onto a carbon film grid with a copper backing. In preliminary studies, particle damage due to high electron voltage and current densities was observed. To avoid this damage to the particles from the electron beam, current densities were kept below 70 pA/cm². The particles are well dispersed and show no agglomeration even after drying on the TEM grid (FIG. 8). Typical particles are shown in the inset of FIG. 8. The particles have a log normal mean and standard deviation of 26±8 nm (n=124 particles) based on diameter measurements using TEM photomicrographs. Atomic force microscopy analysis (data not shown) has been used to verify the spherical particle morphology.

The calcium and phosphate ratio was measured by ICP-MS. The molar ratio of Ca:P is 0.98:1. The ratio is low compared to the synthesis ratio (1.67:1). This is likely due to the formation of calcium-dye complexes which are excluded from the particle during the synthesis.

Fluorescence correlation spectroscopy was used to determine the solution phase behavior of the particles in order to better understand the particulate behavior in biologically-relevant solutions and to monitor only the fluorescing species. To this end we examined the free dye and the particles in DPBS (Dulbecco's phosphate buffered saline), at pH 7 and at pH 4. Low pH conditions mimicked the acidic environment of an endo-lysosome in which a particle would be enveloped during endocytosis.

Figure 9:
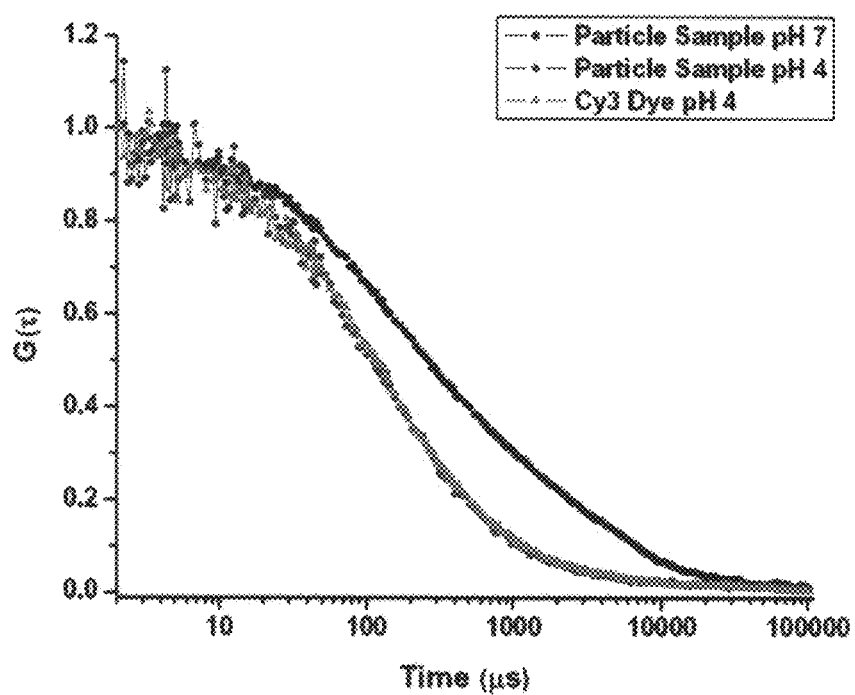
FIG. 9 shows sample autocorrelation curves of nanoparticles in pH 7 (black), nanoparticles in pH 4 (blue), and free Cy3 dye in pH 4 (red).
Figure 10:
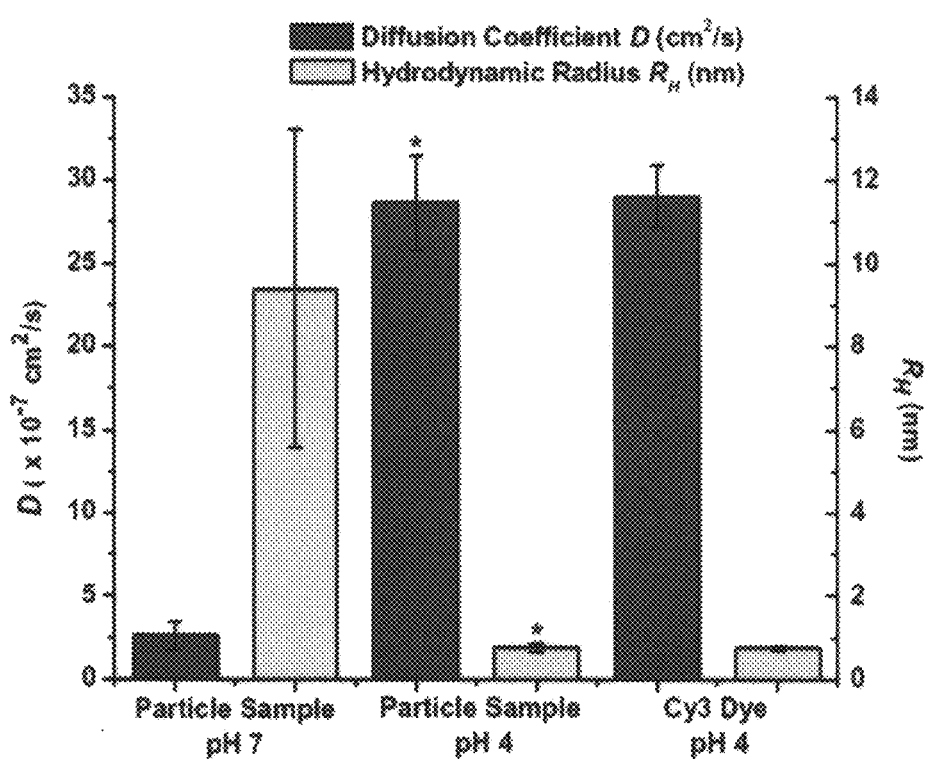
FIG. 10 shows the diffusion coefficient D (black) and hydrodynamic radius (grey) of free cy3 dye at pH 4 and nanoparticles at pH 4 and pH 7. *p<0.0001 for pH 4 vs. pH 7. No significant difference for D ($R_H$) was detected between nanoparticle samples and Cy3 for pH 4. The large standard deviation of the particle sample at pH 7 reflects the distribution in particle diameters. The diffusion coefficient D (black) is shown in the bar positioned to the left of the hydrodynamic radius bar (grey).

FCS measurements were collected for free Cy3 dye at pH 4, Cy3-doped nanoparticles at pH 4 and pH 7 in DPBS. Sample autocorrelation curves are shown in FIG. 9, where a shift of the curve to the right (greater characteristic diffusion time) signifies a lower diffusion coefficient and a larger hydrodynamic radius. In this case, the diffusion time of free Cy3 dye molecules is 127 μs and that of the nanoparticles at pH 7 is 1311 μs. The mean values and standard deviations for diffusion coefficients and hydrodynamic radii are reported in FIG. 10. Nanoparticles in DPBS show a diffusion coefficient $D=2.60\pm0.81\times10^{-7}$ cm²/s at pH 7 and $D=28.6\pm0.28\times10^{-7}$ cm²/s at pH 4; while free Cy3 dye shows a value of $D=29.0\pm0.18\times10^{-7}$ cm²/s at pH 4. The corresponding hydrodynamic radii are $R_H=9.40\pm3.83$ nm for the nanoparticles at pH 7, $R_H=0.76\pm0.09$ nm for the nanoparticles at pH 4 and $R_H=0.75\pm0.06$ nm for the free dye at pH 4. Similar results were obtained for the nanoparticles in DI water at pH 7 and pH 4 (data not shown). In addition to the diffusion data, the particle number concentration can be determined based on the number of particles that diffuse through the observation volume. The CPNP suspension has a particle number concentration of $\sim 6 \times 10^{14}$ particles/mL, based on these determinations.

These results show that in acidic solutions, the nanoparticles have a diffusion coefficient and hydrodynamic radius equivalent to that of free Cy3 supporting the conclusion that low solution pH induces dissolution of CP, and release of the encapsulated dye.

Figure 11:
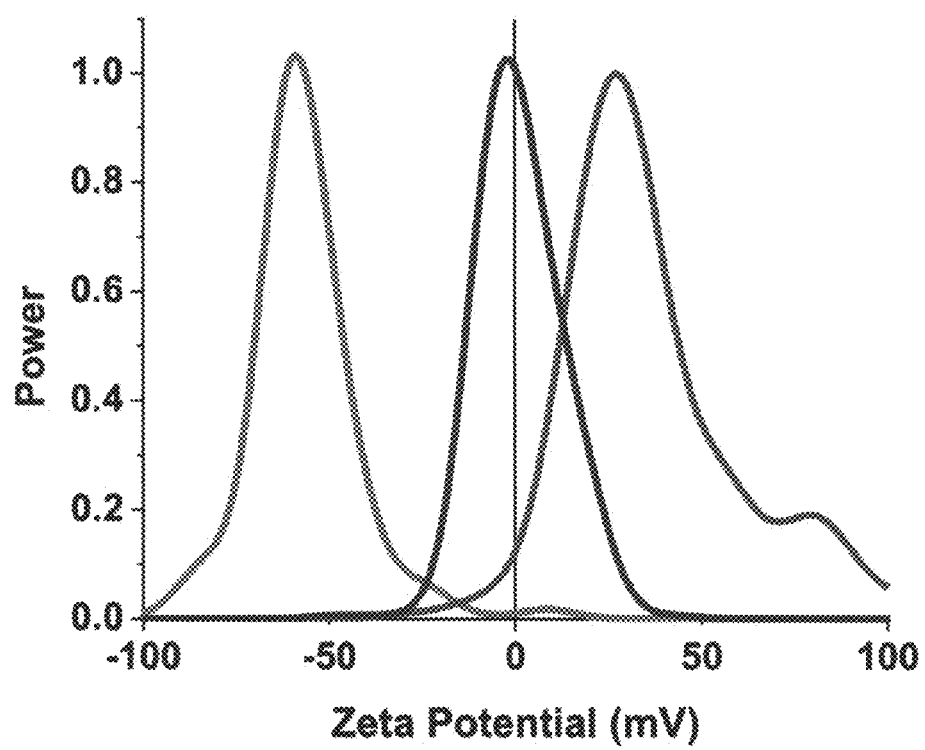
FIG. 11 shows the zeta potential distributions of the CPNPs with various surface terminations in 70:30 EtOH:H2O at pH 6-7. The COO$^-$ terminated particles (red line) have a mean zeta potential of −30±3 mV. The —NH$_3^+$ terminated particles (green line) have a mean zeta potential of +24±6 mV. The PEG terminated particles (blue line) have a mean zeta potential of 3±2 mV.

The zeta potential distributions are collected using a Brookhaven ZetaPALS zeta potential analyzer. FIG. 11 shows the effect of various surface functionalities on the surface potential. The zeta potential distributions verify a strong dependence of the charge on the surface functionality. The citrate functionalized CPNPs exhibit a reasonably high magnitude negative charge of $-29\pm3$ mV with a half-width at 16 mV. The amine and PEG terminated CPNPs have a mean charge of +24±6 mV with a half-width of 18 mV and 3±2 mV with a half-width of 14 mV, respectively. Large standard deviations are expected from neutrally charged samples due to the inherent error associated with attempts to measure particles at zero zeta potential via electrophoretic light scattering. The main utility of amino- and carboxy-surface terminations is to use them as platforms for secondary functionalization through the use of amide linkages, as demonstrated, for example in the case of PEG attachment. It should be noted, however, that in order to use the silane coupling agent for amino-functionality, a large excess of APTES was required. This results in the formation of a silica shell, which in turn will affect the solubility and bioresorbability of the particle. We found that if small quantities of APTES were added, low or neutral zeta potentials are present and the samples showed significant aggregation (data not shown). Other methods of amino-functionalization will be explored in future work, such as the use of aminoethyl dihydrogen phosphate or glycine to act as calcium binding agents.

Figure 12:
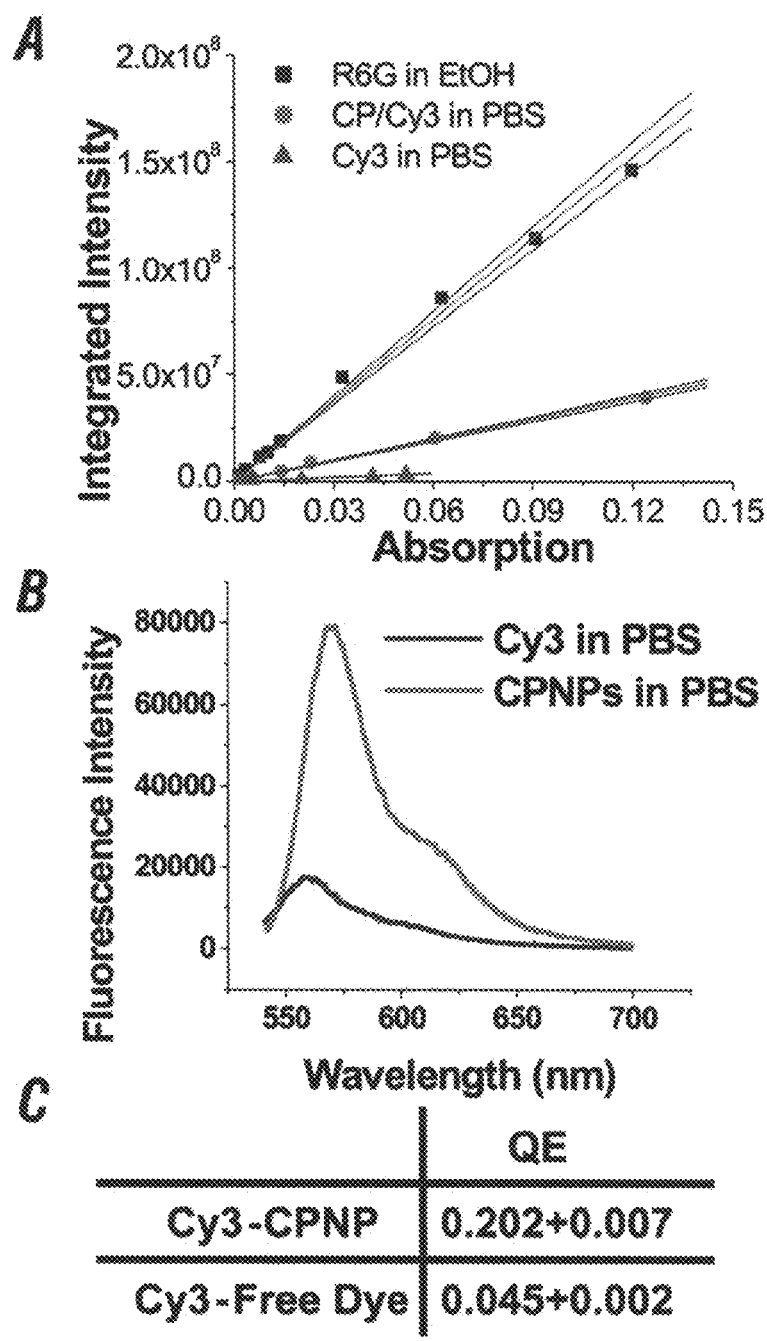
FIG. 12 (A) The integrated fluorescence intensity versus the absorption at 532 nm for Cy3-CPNPs, Cy3-Free Dye, and Rhodamine 6G as a reference. The slope of the line is used to calculated the quantum efficiency via equation 1. (B) Emission spectra of Cy3 encapsulated in calcium phosphate nanoparticles (CPNPs, red) and in free solution (blue) with an excitation of 532 nm. The solutions were tailored to have the same absorption at 532 nm. The maximum intensity of the CPNPs is more than 4.5 times the maximum intensity of the free fluorophore. (C) The quantum efficiency of the Cy3 encased in CPNPs (0.202), and the Cy3 in free solution (0.045).

As a comparison of the free dye to the encapsulated dye, the relative fluorescence quantum efficiency (QE) was determined according to techniques in the literature. (Williams, A. T. R.; Winfield, S. A.; Miller, J. N. *The Analyst* 1983, 108, 1067-1071; Kubin, R. F.; Fletcher, A. N. *Journal of Luminescence* 1982, 27, 455-462). In brief, the integrated fluorescence signals of the free Cy3 and the Cy3-doped CPNPs in PBS were compared to a known reference standard with an excitation wavelength of 532 nm and the QE was calculated using a modified relationship from Lakowicz (Lakowicz, J. R., *Principles of Fluorescence Spectroscopy*. Third ed.; Springer Science and Business Media: New York, 2006; p 54), $$\Phi = \Phi_R \frac{M}{M_R} \frac{n^2}{n_R^2} \quad [1]$$

where $\Phi$, and $\Phi_R$ are the QE for the sample and the reference respectively, M and $M_r$ are the slopes of the integrated intensity versus absorption plots (FIG. 12A) and n is the refractive index of each solvent. Rhodamine 6G in ethanol was used as a reference with a quantum efficiency of 0.95. (Kubin, R. F.; Fletcher, A. N. *Journal of Luminescence* 1982, 27, 455-462). The Cy3-doped CPNPs exhibited a quantum efficiency of 0.202±0.007 in PBS, while the free dye efficiency was 0.045±0.002 in PBS within a 95% confidence interval (FIG. 12C). Our measured QE for the free Cy3 dye is comparable to literature values ranging from 0.03 to 0.05. (Southwick, P. L.; Ernst, L. A.; Tauriello, E. W.; Parker, S. R.; Mujumdar, R. B.; Mujumdar, S. R.; Cleaver, H. A.; Waggoner, A. S. *Cytometry* 1990, 11, 418-430). FIG. 12B exemplifies this enhancement in QE by comparing the fluorescence signal of the Cy3-doped CPNPs to a solution of Cy3 free dye with the same absorption at 532 nm. There is more than a 4.5-fold increase in the maximum intensity of the CPNPs versus the free dye as well as a 9 nm red shift in the peak wavelength. This enhancement is attributed to caging effects that isolate the dye from the solvent and from specific dye-dye interactions. (Avnir, D.; Levy, D.; Reisfeld, R. *Journal of Physical Chemistry B* 1984, 88, 5956-5959). Based on the intensity per particle and the particle number concentration from the FCS measurements, there are ~5-8 dye molecules per particle.

Figure 13:
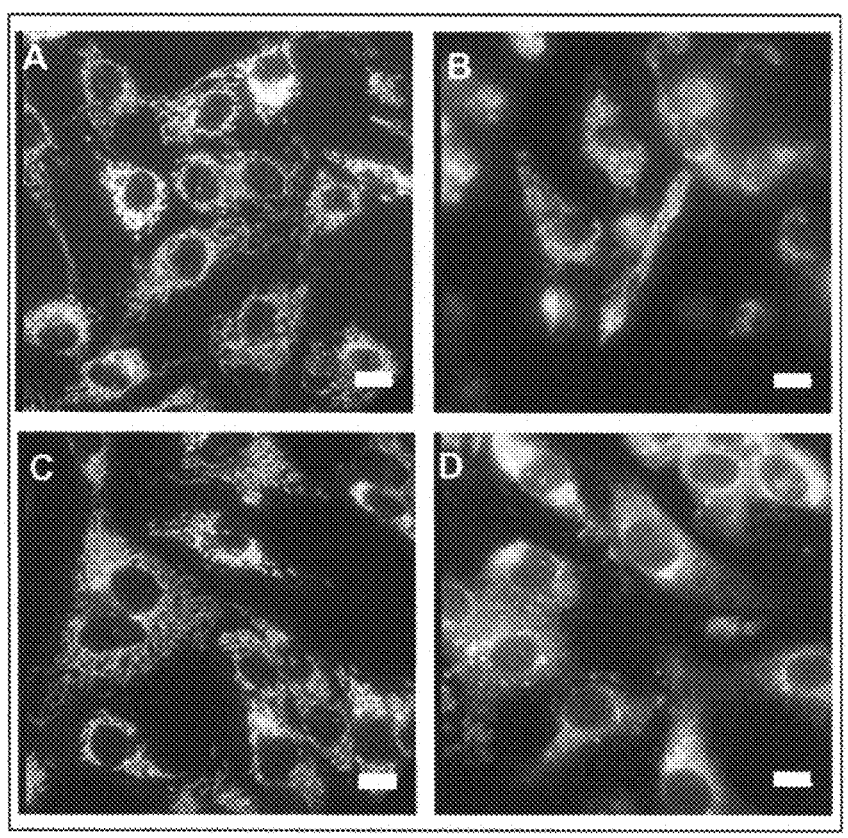
FIG. 13 shows bovine aortic endothelial cells stained with free Cy3 and either untreated (A), or treated with cytochalasin-D (Cyto-D) to inhibit vesicle transport (B). The staining patterns of the free dye were compared to the cells that were stained with Cy3-encapsulated calcium phosphate nanoparticle (Cy3-CPNP) which were either untreated (C) or treated with Cyto-D (D). The internal membranous organelles clearly show specific staining in both of the untreated sets of cells (A and C), while the cells that were treated with Ctyo-D show very different staining patterns (B and D). The Cy3-CPNPs do not stain the internal membranes when the cells were treated with Cyto-D, indicating the particles remain undissolved. The scale bars are 10 microns.

Based on the results showing pH-dependent dissolution of the CPNPs, we hypothesized that CPNPs would undergo dissolution when endocytosed by cells, due to the low pH conditions that exist in endolysosomes at late-stage endocytosis. Staining of bovine aortic cells with Cy3 free dye and Cy3-encapsulated CPNPs is shown in FIGS. 13A and 13C respectively. The staining pattern in both these cases is identical and shows specific staining of internal membranous organelles, indicating that the nanoparticles have undergone dissolution. To confirm that the process of dissolution was mediated by endocytosis, we stained cells treated with cytochalasin-D (FIGS. 13B and 13D). Cytochalasin-D drug disrupts actin polymerization which plays multiple roles in endocytosis, including coated pit formation, vesicle transport through cytoplasm, and vesicle fusion. (Qualmann, B.; Kessels, M. M.; Kelly, R. B. *Journal of Cell Biology* 2000, 150, F111-F116). Cytochalasin-D treated cells stained with nanoparticles show diffuse staining of the entire cytoplasm along with some bright speckles which might correspond to individual nanoparticles or nanoparticle-bearing endosomes (shown in FIG. 13D). No specific staining of the internal membraneous organelles could be observed. Furthermore, cytochalasin-D treated cells stained with Cy3 free dye show a similar staining pattern as the untreated cells (FIG. 13B). This evidence suggests that dissolution of CPNPs in cells is mediated by endocytosis.

Figure 14:
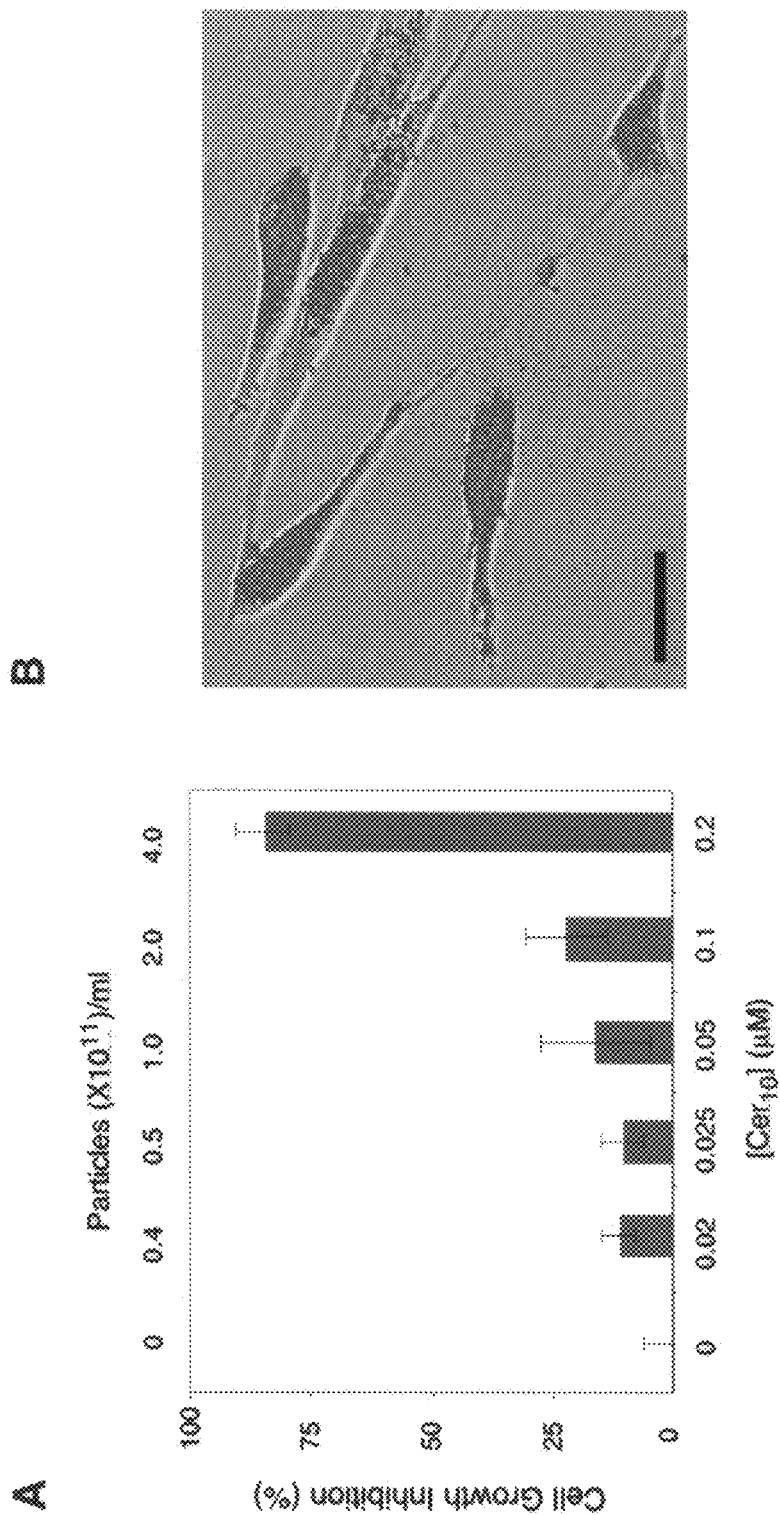
FIG. 14 (A) The growth inhibition of vascular smooth muscle cells as a function of concentration of Cer$_{10}$ delivered via CPNPs, and (B) an image of the cells showing the fluorescence overlayed with the differential interference contrast image. The cells retain their morphology indicating no apoptotic of cytotoxic effects. The scale bar is 20 microns.

To further verify their potential as drug delivery vehicles, amine terminated CPNPs encasing fluorescein sodium salt and an experimental chemotherapeutic, decanoyl-ceramide ($Cer_{10}$) were used to determine the efficacy of the particles as simultaneous imaging and drug delivery agents. Ceramides are a class of molecules currently being explored as chemotherapeutic agents that induce an apoptotic response in cancer cells, and inhibits cell growth in healthy cells. (Bourbon, N. A.; Sandirasegarane, L.; Kester, M. *J. Biol. Chem.* 2002, 277, 3286-3292). Confirmation of simultaneous imaging and drug delivery using ceramide-doped calcium phosphate nanoparticles is shown in FIG. 14. Human vascular smooth muscle cells were chosen to demonstrate simultaneous drug delivery and fluorescence imaging. Activated vascular smooth muscle cells lead to artherosclerosis or restenosis resulting in reduced luminal cross-sections in diseased arteries. Ceramide delivered via nanoliposomes reduces cell growth in these cells. (Bourbon, N. A.; Sandirasegarane, L.; Kester, M. *J. Biol. Chem.* 2002, 277, 3286-3292; Charles, R.; Sandirasegarane, L.; Yun, J.; Bourbon, N. A.; Rothstein, R.; Wilson, R.; Levinson, S. W.; Kester, M. *Circulation Research* 2000, 87, (4), 282-288). The $Cer_{10}$-fluorescein-doped CPNPs induced up to 80% cell growth inhibition at 0.2 µM ceramide (FIG. 14A), an effective dose approximately 25-fold less than if ceramide was administered in DMSO (data not shown). Significantly, 100% of the smooth muscle cells retained morphological integrity and relatively homogeneous, bright fluorescence (FIG. 14B).

In summary, 20-30 nm diameter organically doped calcium phosphate nanoparticles were prepared using a variety of fluorescent dyes. Specifically, Cascade Blue©, SAB, fluorescein sodium salt, rhodamine WT, and Cy3 amidite were successfully encapsulated displaying the ability to encapsulate several varieties of small organic molecules. Comparisons of the diameter by FCS and TEM confirm solution phase colloidal stability of the particles, as well as their spherical morphology. Additionally, the fluorescence quantum efficiency exhibited nearly a 4 fold increase from 0.045 to 0.202 for the free and encapsulated dye respectively. Dissolution of the particles at low pH was proven by a shift in the diffusion coefficient to larger values, indicating a release of encapsulated contents in environments similar to endolysosomes. As further proof of this property, bovine aortic cells were effectively stained with the particles, and dissolution was inhibited through the use of cytochalasin-D. Preliminary drug delivery results show that a hydrophobic chemotherapeutic, such as ceramide, can be delivered in vitro to human vascular cells. Both carboxy- and amino-functional nanoparticles were prepared, and the carboxy-terminal particles were successfully used as a platform for PEG functionalization. Current and future work is focused on the use of the CPNPs for both bioimaging and drug delivery.

Example 10

Fluorescence Correlation Spectroscopy Data

The diffusion coefficients and their associated hydrodynamic radii for the ten measurements collected for each sample type (the nanoparticle samples at pH 7 and pH 4, and the Cy3 free dye at pH 4) are listed in Table S1.

TABLE S1

Diffusion Coefficients and Hydrodynamic Radii of the Nanoparticle Sample and Cy3 Dye in DPBS

| Run | Nanoparticle Sample pH 7.0 | | Nanoparticle Sample pH 4 | | Cy3 Dye pH 4 | |
|---|---|---|---|---|---|---|
| | Diffusion (cm²/s) | $R_H$ (nm) | Diffusion (cm²/s) | $R_H$ (nm) | Diffusion (cm²/s) | $R_H$ (nm) |
| 1 | $2.88 \times 10^{-7}$ | 7.52 | $2.70 \times 10^{-6}$ | 0.802 | $2.87 \times 10^{-6}$ | 0.757 |
| 2 | $1.36 \times 10^{-7}$ | 15.99 | $2.23 \times 10^{-6}$ | 0.972 | $2.86 \times 10^{-6}$ | 0.757 |
| 3 | $1.35 \times 10^{-7}$ | 16.09 | $2.65 \times 10^{-6}$ | 0.818 | $3.05 \times 10^{-6}$ | 0.711 |
| 4 | $2.31 \times 10^{-7}$ | 9.37 | $3.14 \times 10^{-6}$ | 0.691 | $2.96 \times 10^{-6}$ | 0.731 |
| 5 | $3.35 \times 10^{-7}$ | 6.48 | $2.76 \times 10^{-6}$ | 0.787 | $2.91 \times 10^{-6}$ | 0.746 |
| 6 | $3.04 \times 10^{-7}$ | 7.12 | $3.03 \times 10^{-6}$ | 0.716 | $2.92 \times 10^{-6}$ | 0.743 |
| 7 | $3.56 \times 10^{-7}$ | 6.08 | $3.02 \times 10^{-6}$ | 0.718 | $2.94 \times 10^{-6}$ | 0.738 |
| 8 | $3.03 \times 10^{-7}$ | 7.15 | $2.96 \times 10^{-6}$ | 0.732 | $3.00 \times 10^{-6}$ | 0.722 |
| 9 | $3.20 \times 10^{-7}$ | 6.78 | $3.15 \times 10^{-6}$ | 0.688 | $3.09 \times 10^{-6}$ | 0.703 |
| 10 | $1.94 \times 10^{-7}$ | 11.16 | $3.00 \times 10^{-6}$ | 0.723 | $2.41 \times 10^{-6}$ | 0.901 |
| Average | $2.60 \times 10^{-7}$ | 9.37 | $2.86 \times 10^{-6}$ | 0.765 | $2.90 \times 10^{-6}$ | 0.751 |
| St. Dev. | $8.13 \times 10^{-8}$ | 3.82 | $2.83 \times 10^{-7}$ | 0.086 | $1.88 \times 10^{-7}$ | 0.056 |

Cell Culture. Bovine aortic endothelial cells (BAECs) were cultured in MCDB-131 complete medium for 2 days (~50-60% confluence) before changing the medium to DMEM (without phenol red) supplemented with 10% FBS. Nanoparticles or free dye was added to this medium to a final concentration of ~1 µM. Cells were incubated with the particles overnight at 37° C. temperature, 95% humidity, and 5% $CO_2$. For drug treatment, cells were incubated with 0.2 µg/ml of Cytochalasin-D along with the nanoparticles. Cells were rinsed at least three times in DPBS (without calcium and magnesium) before imaging them on an epi-fluorescence microscope. Cells used were between 5-10 passages.

The primary human vascular smooth muscle (HVSM) cell line (CAMBREX, East Rutherford, N.J.) was cultured in Medium 231 with 10% SMGS (smooth muscle growth supplement containing 5% fetal bovine serum, basic fibroblast growth factor, epidermal growth factor and insulin; Cascade Biologics, Portland, Oreg.) in the presence of penicillin/streptomycin at 37° C. in a humidified atmosphere of 5% carbon dioxide. All experiments were performed with cells that had been passaged fewer than ten times. For nanoparticulate uptake assays, HVSM cells were seeded into Lab-Tek® (Nunc, Rochester, N.Y.) chambered cover glass slides. Next day, cells were treated with fluorescein-doped calcium phosphate nanoparticles for 30 min. Images of cells with fluorescence were taken using the digital camera attached to Nikon Eclipse (TE 2000-S) fluorescent microscope. A cutoff filter built into the microscope between the maximum excitation wavelength (475 nm) and the maximum emission wavelength (515 nm) for fluorescein was used to obtain fluorescent images of the cells after exposure to approximately 10 ng/µL of the nanoparticles in cell culture media. For cell growth assay, HVSM cells were seeded in 6-well culture dishes ($5 \times 10^4$ cells/well). After 24 h, the media was changed to SMGS-free to induce growth arrest. After 18 h, the cells were treated with vehicle (PBS) or $C_6$-ceramide-CPNPs for 30 min and then stimulated with 10% SMGS. After 2 days, viable cells, as determined by trypan blue exclusion, were counted using a hemocytometer.

Example 11

Bioresorbable Indocyanine Green-Doped Calcium Phosphate Nanoparticles for Near-Infrared In Vivo Imaging of Human Breast Cancer

Early detection is a crucial element for the timely diagnosis and successful treatment of all human cancers, but is limited by the sensitivity of current imaging methodologies. We have synthesized and studied bioresorbable calcium phosphate nanoparticles (CPNPs) in which molecules of the near-infrared (NIR) emitting fluorophore, indocyanine green (ICG), are embedded. The ICG-CPNPs demonstrate exceptional colloidal and optical characteristics. Suspensions consisting of 20 nm average diameter particles are colloidally stable in physiological solutions (phosphate buffered 0.15M saline (PBS), pH 7.4) with carboxylate or polyethylene glycol (PEG) surface functionality. ICG doped CPNPs exhibit significantly greater intensity at the maximum emission wavelength relative to the free constituent fluorophore, consistent with the multiple molecules encapsulated per particle. The quantum efficiency per molecule of the ICG-CPNPs is 200 percent greater at 0.049±0.003 over the free fluorophore in PBS. Photostability based on fluorescence half-life of encapsulated ICG in PBS is 500 percent longer under typical clinical imaging conditions relative to the free dye. PEGylated ICG-CPNPs accumulate in solid, 5 mm diameter xenograft breast adenocarcinoma tumors via enhanced retention and permeability (EPR) within 24 hours after systematic tail vein injection in a nude mouse model. Ex situ tissue imaging further verifies the facility of the ICG-CPNPs for deep-tissue imaging with NIR signals detectable from depths up to 3 cm in porcine muscle tissue. Our ex vivo and in vivo experiments verify the promise of the NIR CPNPs for diagnostic imaging in the early detection of solid tumors.

The advantages associated with early detection of disease (Bornhop, D. J.; Contag, C. H.; Licha, K.; Murphy, C. J. *J. Biomedical Opt.* 2001, 6, 106-110) have initiated much interest in exogenous contrast agents as a means of optically imaging markers unique to specific cell types at the onset of a disease, such as breast cancer, far in advance of changes on the gross anatomic level. (Morawski, A. M.; Lanza, G. A.; Wickline, S. A. *Current Opinion in Biotechnology* 2005, 16, 89-92; Loo, C.; Lowery, A.; Halas, N.; West, J.; Drezek, R. *Nano Lett.* 2005, 5, (4), 709-711; Lin, A. W. H.; Lewinski, N. A.; West, J. L.; Halas, N. J.; Drezek, R. A. *Journal of Biomedical Optics* 2005, 10, (6)). Fluoroprobes, for example, are being developed to achieve this selective imaging sensitivity (Rao, J.; Dragulescu-Andrasi, A.; Yao, H. *Current Opinion in Biotechnology* 2007, 18, 17-25), particularly those that work in the near-infrared (NIR, 700-900 nm) spectrum, a wavelength region of low absorptivity by tissue chromophores. (Weissleder, R. *Nature Biotechnology* 2001, 19, 316-317).

This permits fluorescence signals relatively free of intrinsic background interference with detectable signal intensities through several centimeters of tissue. (Loo, C.; Lowery, A.; Halas, N.; West, J.; Drezek, R. *Nano Lett.* 2005, 5, (4), 709-711; Sevick-Muraca, E. M.; Houston, J. P.; Gurfinkel, M. *Current Opinion in Chemical Biology* 2002, 6, (5), 642-650)

Indocyanine green (ICG) is a NIR contrast agent which has been widely investigated for use in deep tissue imaging, and is the only NIR organic dye approved by the U.S. Food and Drug Administration (FDA) for human use. (Malicka, J.; Gryczynski, I.; Geddes, C. D.; Lakowicz, J. R. *Journal of Biomedical Optics* 2003, 8, (3), 472-478). ICG is an amphiphilic carbocyanine dye that exhibits absorption and emission maxima around 780 and 820 nm, respectively. (Benson, R. C.; Kues, H. A. *Physics in Medicine and Biology* 1978, 23, (1), 159; Yu, J.; Yaseen, M. A.; Anvari, B.; Wong, M. S. *Chem. Mater.* 2007, 19, (6), 1277-1284; Landsman, M. L. J.; Kwant, G.; Mook, G. A.; Zijlstra, W. G. *Journal of Applied Physiology* 1976, 40, (4), 575-583). Due to its low toxicity ($LD_{50}$ of 50-80 mg/kg for animal subjects (Taichamn, G. C.; Hendry, P. J.; Wilbert, J. K. *Texas Heart Institute Journal* 1987, 14, 133-138)), ICG is used clinically as a contrast agent for optical imaging in angiography (Schutt, F.; Fischer, J.; Kopitz, J.; Holz, F. G. *Clinical and Experimental Ophthalmology* 2002, 30, (2), 110-114) and guiding biopsies (Motomura, K.; Inaji, H.; Komoike, Y.; Kasugai, I.; Noguchi, S.; Koyama, H. *Japanese Journal of Clinical Oncology* 1999, 29, (12), 604-607), as well as for evaluating blood flow (Ishihara, H.; Okawa, H.; Iwakawa, T.; Umegaki, N.; Tsubo, T.; Matsuki, A. *Anesthesia and Analgesia* 2002, 94, (4), 781-786; Ott, P. *Pharmacology and Toxicology* 1998, 82, 1-48) and hepatic function. (Paumgartner, G.; Probst, P.; Kraines, R.; Leevy, C. M. *Annals of the New York Academy of Sciences* 1970, 170, 134-147; Caesar, J.; Shaldon, S.; Chiandussi, L.; Guevara, L.; Sherlock, S. *Clin. Sci.* 1961, 21, 43-57). It is one of the least toxic contrast agents administered to humans (Frangioni, J. V. *Current Opinion in Chemical Biology* 2003, 7, (5), 626-634), with the only known adverse reaction being rare anaphylaxis. (Olsen, T. W.; Lim, J. I.; Capone, A.; Myles, R. A.; Gilman, J. P. *Archives of Ophthalmology* 1996, 114, 97).

However, as with many organic dye molecules, ICG has a low fluorescence quantum yield due to internal conversion (Philip, R.; Penzkofer, A.; Baumler, W.; Szeimies, R. M.; Abels, C. *Journal of Photochemistry and Photobiology A: Chemistry* 1996, 96, 137-148; Soper, S. A.; Mattingly, Q. L. *Journal of the American Ceramic Society* 1994, 116, 3744-3752), and is prone to photobleaching, solvatochromic effects, and nonspecific quenching, all of which limit its utility in sensitive and prolonged in vivo imaging applications. (Sevick-Muraca, E. M.; Houston, J. P.; Gurfinkel, M. *Current Opinion in Chemical Biology* 2002, 6, (5), 642-650; Yu, J.; Yaseen, M. A.; Anvari, B.; Wong, M. S. *Chem. Mater.* 2007, 19, (6), 1277-1284; Philip, R.; Penzkofer, A.; Baumler, W.; Szeimies, R. M.; Abels, C. *Journal of Photochemistry and Photobiology A: Chemistry* 1996, 96, 137-148; Lakowicz, J. R., *Principles of Fluorescence Spectroscopy.* 3rd ed.; Springer: Baltimore, Md., 2006; Yan, J.; Estevez, C.; Smith, J.; Wang, K.; He, X.; Wang, L.; Tan, W. *Nanotoday* 2007, 2, (3), 44-50). Numerous efforts have reported the optical instability of ICG in physiologically relevant solutions such as water (Landsman, M. L. J.; Kwant, G.; Mook, G. A.; Zijlstra, W. G. *Journal of Applied Physiology* 1976, 40, (4), 575-583; Desmettre, T.; Devoisselle, J. M.; Mordon, S. *Survey of Ophthalmology* 2000, 45, (1), 15-27; Simmons, R.; Shephard, R. J. *Journal of Applied Physiology* 1971, 30, (4), 502-507), salt solutions (Landsman, M. L. J.; Kwant, G.; Mook, G. A.; Zijlstra, W. G. *Journal of Applied Physiology* 1976, 40, (4), 575-583; Gathje, J.; Steuer, R. R.; Nicholes, K. R. K. *Journal of Applied Physiology* 1970, 29, (2), 181-185), plasma Landsman, M. L. J.; Kwant, G.; Mook, G. A.; Zijlstra, W. G. *Journal of Applied Physiology* 1976, 40, (4), 575-583; Simmons, R.; Shephard, R. J. *Journal of Applied Physiology* 1971, 30, (4), 502-507; Gathje, J.; Steuer, R. R.; Nicholes, K. R. K. *Journal of Applied Physiology* 1970, 29, (2), 181-185), and blood. (Simmons, R.; Shephard, R. J. *Journal of Applied Physiology* 1971, 30, (4), 502-507; Holzer, W.; Mauerer, M.; Penzkofer, A.; Szeimies, R. M.; Abels, C.; Landthaler, M.; Baumler, W. *Journal of Photochemistry and Photobiology B: Biology* 1998, 47, (2-3), 155-164; Mordon, S.; Devoisselle, J. M.; Soulie-Begu, S.; Desmettre, T. *Microvascular Research* 1998, 55, (2), 146-152; Maarek, J. M. I.; Holschneider, D. P.; Harimoto, J. *Journal of Photochemistry and Photobiology B-Biology* 2001, 65, (2-3), 157-164). In such environments, oxidation and dimerization degrade the original molecule, resulting in decreased absorption, reduced fluorescence, and variability in the maximum absorption wavelength. (Zhang, Y.; Wang, M. *Materials Letters* 2000, 42, 86-91; Saxena, V.; Sadoqi, M.; Shao, J. *Journal of Pharmaceutical Sciences* 2003, 92, (10), 2090-2097). Furthermore, ICG often binds to proteins (Muckle, T. J. *Biochemical Medicine* 1976, 15, (1), 17-21) leading to rapid agglomeration and subsequent elimination from the body with a plasma half-life from 2 to 4 min. (Desmettre, T.; Devoisselle, J. M.; Mordon, S. *Survey of Ophthalmology* 2000, 45, (1), 15-27; Mordon, S.; Devoisselle, J. M.; Soulie-Begu, S.; Desmettre, T. *Microvascular Research* 1998, 55, (2), 146-152).

Sensitive, real-time in vivo monitoring schemes require that a fluoroprobe retain its state of dispersion in physiological environments, sustain a strong, prolonged signal intensity, accumulate in targeted regions of interest, and passively resorb into the body upon completion of function. (Rao, J.; Dragulescu-Andrasi, A.; Yao, H. *Current Opinion in Biotechnology* 2007, 18, 17-25). One of the significant advantages nanotechnology has brought to bioimaging is the capacity to improve various fluoroprobe molecules for in vivo applications. (Rao, J.; Dragulescu-Andrasi, A.; Yao, H. *Current Opinion in Biotechnology* 2007, 18, 17-25; Jin, S.; Ye, K. *Biotechnol Prog* 2006, 23, (1), 32-41). An assortment of nanoparticulate systems have been developed to encapsulate fluorescent molecules for bioimaging applications; the reader is directed elsewhere for comprehensive reviews of these various colloidal carriers. (Yan, J.; Estevez, C.; Smith, J.; Wang, K.; He, X.; Wang, L.; Tan, W. *Nanotoday* 2007, 2, (3), 44-50; Sharma, P.; Brown, S.; Walter, G.; Santra, S.; Moudgil, B. *Advances in Colloid and Interface Science* 2006, 123, 471-485). A primary significance of these particulate modifications is the extension of circulation half-life and in vivo stability relative to the free constituent fluoroprobe molecules. (Yu, J.; Yaseen, M. A.; Anvari, B.; Wong, M. S. *Chem. Mater.* 2007, 19, (6), 1277-1284; Devoisselle, J. M.; Soulie-Begu, S.; Mordon, S.; Desmettre, T.; Maillols, H. *Lasers in Medical Science* 1998, 13, (4), 279-282). Several studies also report the amplified optical emission for a single particle containing multiple fluorophores relative to a single fluorophore molecule. (Zhao, X.; Bagwe, R. P.; Tan, W. *Advanced Materials* 2004, 16, (2), 173-176; Ow, H.; Larson, D. R.; Srivastava, M.; Baird, B. A.; Webb, W. W.; Wiesner, U. *Nano Lett.* 2005, 5, (1), 113-117; Zhou, X.; Zhou, J. *Anal Chem* 2004, 76, 5302-5312; Bele, M.; Siiman, O.; Matijevic, E. *Journal of Colloid and Interface Science* 2002, 254, 274-282). Perhaps the most promising attribute of fluorophore-doped particles is the improved photostability of the encapsulate by both the inhibition of unfavorable conformational reorganization (Soper, S. A.; Mattingly, Q. L. *Journal of the American Ceramic Society* 1994, 116, 3744-3752) and reduced interactions with solvent molecules, which avoid dynamic processes that result in non-radiative energy losses. Avnir, D.; Levy, D.; Reisfeld, R. *Journal of Physical Chemistry* 1984, 88, (24), 5956-5959).

Polymer-based carriers are one of the most common types of particulate systems employed for in vivo applications (Burns, A.; Sengupta, P.; Zedayko, T.; Baird, B.; Wiesner, U. *Small* 2006, 6, 723-726) due to high biocompatibility and the facility with which resorbability is achieved. (Soppimath, K. S.; Aminabhavi, T. M.; Kulkarni, A. R.; Rudzinski, W. E. *Journal of Controlled Release* 2001, 70, 1-20). Recent years have witnessed numerous polymeric modalities to address the intrinsic issues of ICG degradation and rapid blood clearance. (Yu, J.; Yaseen, M. A.; Anvari, B.; Wong, M. S. *Chem. Mater.* 2007, 19, (6), 1277-1284; Saxena, V.; Sadoqi, M.; Shao, J. *International Journal of Pharmaceutics* 2004, 278, (2), 293-301; Yaseen, M. A.; Yu, J.; Wong, S. M.; Anvari, B. *Biotechnology Progress* 2007, 23, (6), 1431-1440; Gomes, A. J.; Lunardi, L. O.; Marchetti, J. M.; Lunardi, C. N.; Tedesco, A. C. *Photomedicine and Laser Surgery* 2006, 24, (4), 514-521). However, these efforts fall short in improving the optical performance for deep tissue imaging schemes. (Yu, J.; Yaseen, M. A.; Anvari, B.; Wong, M. S. *Chem. Mater.* 2007, 19, (6), 1277-1284). Saxena et al. (Saxena, V.; Sadoqi, M.; Shao, J. *Journal of Photochemistry and Photobiology B-Biology* 2004, 74, (1), 29-38) improved aqueous and thermal stabilities by encapsulating ICG within ~350 nm poly(lactic-co-glycolic acid) (PLGA) particles, but these carriers suffered significant leakage with 78% ICG loss within 8 hours in physiological conditions. Subsequently, a silica-polymer composite microcapsule was developed to improve encapsulated ICG retention (17% ICG leakage after 8 hours at 37° C.) (Yu, J.; Yaseen, M. A.; Anvari, B.; Wong, M. S. *Chem. Mater.* 2007, 19, (6), 1277-1284), but the addition of the nanoparticulate shell increased the particle size to 1 micron. However, the polymer network gives the encapsulated molecules little protection from dimerization or photo-isomerisation, as evidenced by the red shift in the peak absorbance wavelength (Yu, J.; Yaseen, M. A.; Anvari, B.; Wong, M. S. *Chem. Mater.* 2007, 19, (6), 1277-1284; Gomes, A. J.; Lunardi, L. O.; Marchetti, J. M.; Lunardi, C. N.; Tedesco, A. C. *Photomedicine and Laser Surgery* 2006, 24, (4), 514-521) and a significant decrease in peak fluorescence intensity. (Saxena, V.; Sadoqi, M.; Shao, J. *Journal of Photochemistry and Photobiology B-Biology* 2004, 74, (1), 29-38). Recent work has improved embedded ICG molecules performance in organically modified silicates, (Kim, G.; Huang, S.; Day, K. C.; O'Donnell, M.; Agayan, R. R.; Day, M. A.; Kopelman, R.; Ashkenazi, S. *Journal of Biomedical Optics* 2007, 12, (4) but the 100 nm silicate carriers lie on the upper limit of the preferred size range for in vivo applications. (Goldberg, M.; Langer, R.; Jia, X. *Journal of Biomaterial Science Polymer Edition* 2007, 18, (3), 241-268; Gao, H.; Shi, W.; Freund, L. B. *Proc. Natl. Acad. Sci. USA* 2005, 102, (27), 9469-9474).

Calcium phosphate (CP) is a primary biomineral that is ubiquitously present in the body (Dorozhkin, S. V.; Epple, M. *Angewandte Chemie—International Edition* 2002, 41, (17), 3130-3146) and whose functions have long been exploited in biocompatible (Weber, J. N.; White, E. W.; Lebiedzik, J. *Nature* 1971, 233, (5318), 337-339; Dubok, V. A. *Powder Metallurgy and Metal Ceramics* 2000, 39, (7-8), 381-394; Chiroff, R. T.; White, R. A.; White, E. W.; Weber, J. N.; Roy, D. M. *J. Biomed. Mater. Res.* 1977, 11, (2), 165-178) bone substitutes and biodegradable adjuvants. (He, Q.; Mitchell, A. R.; Johnson, S. L.; Wagner-Bartak, C.; Morcol, T.; Bell, S. J. D. *Clin. Diagn. Lab. Immunol.* 2000, 7, (6), 899-903). Several issues arise when employing exogenous agents for in vivo use, particularly the cytotoxicity to organelles and induction of apoptosis (Jeng, H. A.; Swanson, J. *Journal of Environmental Science and Health, Part A* 2006, 41, (12), 2699-2711), as well as the deposition and clearance from the body. (Jin, S.; Ye, K. *Biotechnol Prog* 2006, 23, (1), 32-41). Recent reports have attributed such toxicity to the intracellular degradation of the endocytosed particles into their constituent components. (Colvin, V. L. *Nature Biotechnology* 2003, 21, (10), 1166-1170; Chang, E.; Thekkek, N.; Yu, W. W.; Colvin, V. L.; Drezek, R. *Small* 2006, 2, (12), 1412-1417; Hoshino, A.; Fujioka, K.; Oku, T.; Suga, M.; Sasaki, Y. F.; Ohta, T.; Yasuhara, M.; Suzuki, K.; Yamamoto, K. *Nano Lett.* 2004, 4, (11), 2163-2169; Lovrić, J.; Bazzi, H. S.; Cuie, Y.; Fortin, G. R. A.; Winnik, F. M.; Maysinger, D. *J Mol Med* 2005, 83, 377-385). For instance, a concern for semiconductor quantum dot (QD) use lies in the presence of heavy metals such as CdSe, which are reportedly toxic to cells even at low concentrations (10 μM/mL). (Hardman, R. *Environmental Health Perspectives* 2006, 114, (2), 165-172). Unlike most of its counterparts, the constituent ions of biodegradable CP particles ($Ca^{2+}$ and $PO_4^{3-}$) are ubiquitously present at millimolar concentrations within the bloodstream. (Oyane, A.; Kim, H.; Furuya, T.; Kobuko, T.; Miyazaki, T.; Nakamura, T. *Journal of Biomedical Materials Research Part A* 2002, 65A, (2), 188-195). Due to this established compatibility and low immune response (He, Q.; Mitchell, A. R.; Johnson, S. L.; Wagner-Bartak, C.; Morcol, T.; Bell, S. J. D. *Clin. Diagn. Lab. Immunol.* 2000, 7, (6), 899-903; Radin, S.; Campbell, J. T.; Ducheyne, P.; Cuckler, J. M. *Biomaterials* 1997, 18, (11), 777-782), many recent efforts (Bisht, S.; Bhakta, G.; Mitra, S.; Maitra, A. *International Journal of Pharmaceutics* 2005, 288, 157-168; Schmidt, H. T.; Gray, B. L.; Wingert, P. A.; Ostafin, A. *Chemistry of Materials* 2004, 16, 4942-4947; Olton, D.; Li, J.; Wilson, M. E.; Rogers, T.; Close, T.; Close, J.; Huang, L.; Kumta, P. N.; Sfeir, C. *Biomaterials* 2007, 28, 1267-1279; Roy, I.; Mitra, S.; Maitra, A.; Mozumdar, S. *International Journal of Pharmaceutics* 2003, 250, 25-33; Sokolova, V.; Prymak, O.; Meyer-Zaika, W.; Colfen, H.; Rehage, H.; Shukla, A.; Epple, M. *Mat.-wiss. u. Werkstofftech* 2006, 37, (6), 441-445; Schmidt, H. T.; Ostafin, A. E. *Advanced Materials* 2002, 14, (7), 532-535) have reported CP preparation as particles for nontoxic and efficient transport of bioactive agents.

The objective of this work is to report a novel carrier system for sensitive deep-tissue NIR imaging using sub-50 nm, biocompatible CP nanoparticles (CPNPs), colloidally stable in physiological solutions, which exploit the matrix-shielding effect and thereby impart improved fluorescence properties to the encapsulated ICG suitable for sensitive, early-state diagnostic imaging.

Example 12

Synthesis and Characterization of NIR:Dye-Doped CP Nanoparticles (CPNPs)

Spherical CPNPs doped with ICG were synthesized using aqueous coprecipitation of calcium chloride and disodium hydrogen phosphate in the presence of disodium silicate within water-in-oil microemulsions as described in METHODS. ICG doping was accomplished through the designed addition of the fluorophore into the microemulsion during precipitation. Particle stability was fostered through electrosteric repulsion via citrate surface functionalization. (Adair, J. H.; Kumar, R.; Antolino, N.; Szepesi, C.; Kimel, R. A.;

Rouse, S. M., Colloidal Lessons for Dispersion of Nanosize Particulate Suspensions. In *Proceedings of the World Academy of Ceramics*, Cesenatico, Italy, 2004). Particle suspensions were then laundered via a van der Waals high performance liquid chromatography (vdW-HPLC) protocol adopted from our previous work to remove residual synthetic components and concentrate the particles in a 7:3 by volume ethanol:water mixture. (Wang, J.; White, W. B.; Adair, J. H. *Journal of Physical Chemistry B* 2006, 110, 4679-4685; Nano Lett., 2008, 8 (12), pp 4108-4115.; Nano Lett., 2008, 8 (12), pp 4116-4121; ACS Nano, 2008, 2 (10), pp 2075-2084). Colloidal characterization included the size distribution, morphology and colloidal state of dispersion of the collected nanoparticle suspensions using transmission electron microscopy (TEM).

Figure 15:
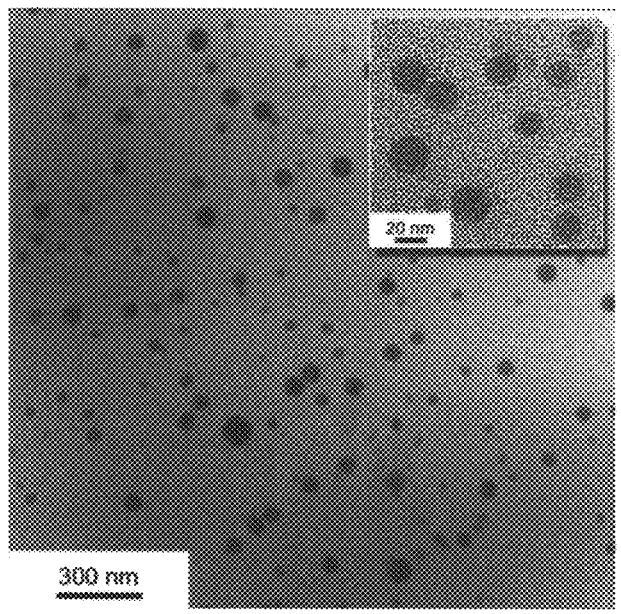
FIG. 15 is a TEM micrograph of a dye-encapsulating ICG-CPNP dispersion with magnified inset showing the particles in detail. The log normal mean and standard deviation of the particle number distribution is 20±11 nm (n=932).

FIG. 15 is a TEM micrograph of the ICG-doped CPNPs. The figure underscores the well dispersed state of the suspension, with the magnified inset illustrating the representative particle size and spherical morphology. Atomic force microscopy data (not shown) verifies the spherical morphology of the particles. The log normal mean particle diameter and standard deviation is 20±11 nm (n=932) based on TEM image analysis. This size range falls within the accepted window for the most efficient cellular uptake ($\leq$50 nm) and closely matches the optimal size of 25 nm for receptor-mediated endocytosis. (Gao, H.; Shi, W.; Freund, L. B. *Proc. Natl. Acad. Sci. USA* 2005, 102, (27), 9469-9474). The electrophoretic mobility, used to verify surface charge on the ICG-doped particles, cannot be measured with the present instrumentation due to the absorption of the 636 nm laser by the embedded ICG fluorophore. Surface charge has been determined using light scattering particle electrophoretic mobility for a variety of functional groups on CPNP surfaces; citrate functionalization gives a negative zeta potential of $-30$ mV. (Nano Lett., 2008, 8 (12), pp 4108-4115.; Nano Lett., 2008, 8 (12), pp 4116-4121; ACS Nano, 2008, 2 (10), pp 2075-2084).

Example 13

Optical Properties of NIR Dye-Doped CPNPs Emission Enhancement

Figure 16:
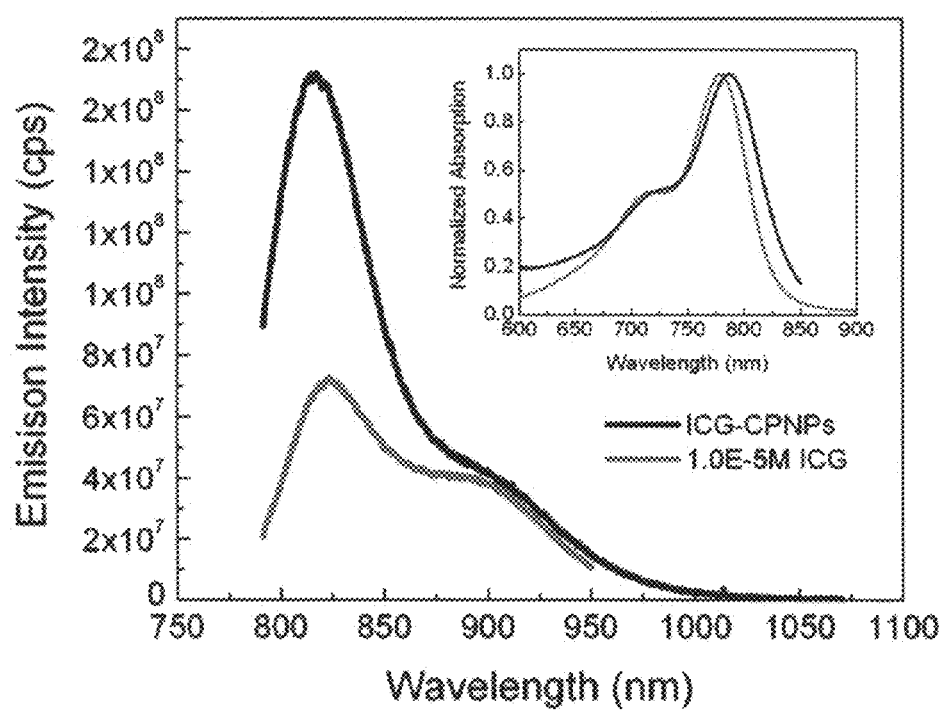
FIG. 16 shows the absorption (inset) and fluorescence spectra of free ICG (red) and ICG-CPNPs (black) in aqueous solution. The CPNP suspension ($10^{13}$ particles/mL) had an apparent fluorophore content of roughly $10^{-5}$ M based on absorption standards; a matching concentration of free dye was used for the comparison. The shape and position of both the absorption and emission spectra are similar, indicating the absence of either chemical modification or dimerization upon encapsulating the dye in the calcium phosphate matrix. Emission from the ICG-CPNPs is significantly brighter than the matching free dye solution, which suffers from quenching interactions due, in part, to free dye self-aggregation.

The fluorescence spectrum of the dye-doped CPNPs was compared to that of the corresponding free ICG dye under identical optical conditions (785 nm excitation). FIG. 16 shows that the shape of both the absorption and emission curves are similar for free ICG and the doped nanoparticles in aqueous solution. This indicates that the encapsulation of the fluorophore within the rigid CP matrix, unlike polymeric encapsulation, retains the monomeric state of the encapsulated ICG without deleterious structural or chemical alterations that adversely affect absorption and emission of the dye. These undesirable phenomena result in peak transformations or spectral shifts, respectively, which are not observed for the embedded ICG emission.

The fluorescence emission intensity of one dye-doped CPNP is approximately $10^3$ times that of one ICG dye molecule as shown in FIG. 16. The enhanced brightness is similar to reports by Zhao et al. on fluorescent silica nanoparticles. (Zhao, X.; Bagwe, R. P.; Tan, W. *Advanced Materials* 2004, 16, (2), 173-176). However, this enhanced brightness is at least partly due to the nanoparticle architecture, with multiple dye molecules encapsulated in a single particle. Thus, brightness or intensity does not provide evidence that the encapsulation provides intrinsically different fluorescence performance than the free molecules. Nonetheless, the encapsulated ICG is uniformly distributed and not self-aggregated in the calcium phosphate matrix based on the elevated intensity for the overall encapsulated $10^{-5}$M ICG. In contrast, self-aggregation and loss of emission intensity of free ICG occurs in aqueous solution at $7 \times 10^{-6}$M at pH 7 (data not shown). To assess whether the elevated brightness is intrinsic to the encapsulated ICG, the quantum efficiency per molecule is presented and discussed.

Example 14

Quantum Efficiency

The fraction of photons absorbed by a molecule that are emitted via a fluorescence photon is quantum efficiency (QE). Thus, QE is the ratio of the number of excited-state fluorophores that relax via a fluorescent transition to the total number of excited-state relaxations that occur, including fluorescence, as well as other non-radiative mechanisms such as internal conversion, vibrational relaxation, intersystem crossing, photoisomerization, or combinations thereof. (Soper, S. A.; Mattingly, Q. L. *Journal of the American Ceramic Society* 1994, 116, 3744-3752; Lakowicz, J. R., *Principles of Fluorescence Spectroscopy*. 3rd ed.; Springer: Baltimore, Md., 2006). The QE provides a metric for the potential of a fluoroprobe in imaging schemes; for sensitive or long-term imaging applications, the fluorescence of the ideal fluoroprobe dominates over competing energy loss pathways, resulting in efficient conversion of absorbed photons to emitted fluorescence signal. Despite widespread use in medical imaging, the QE for the ICG monomer in aqueous solution is only 0.027±0.005 (Philip, R.; Penzkofer, A.; Baumler, W.; Szeimies, R. M.; Abels, C. *Journal of Photochemistry and Photobiology A: Chemistry* 1996, 96, 137-148) with values as low as 0.01 reported. (Soper, S. A.; Mattingly, Q. L. *Journal of the American Ceramic Society* 1994, 116, 3744-3752). Loss for ICG is primarily due to internal conversion (Philip, R.; Penzkofer, A.; Baumler, W.; Szeimies, R. M.; Abels, C. *Journal of Photochemistry and Photobiology A: Chemistry* 1996, 96, 137-148), since intersystem crossing mechanisms amount to a negligible rate of triplet formation. (Reindl, S.; Penzkofer, A.; Gong, S. H.; Landthaler, M.; Szeimies, R. M.; Abels, C.; Baumler, W. *Journal of Photochemistry and Photobiology A: Chemistry* 1997, 105, (1), 65-68). The relative QE of dye encapsulating ICG-CPNPs in PBS was compared to free ICG molecules in the same environment, measured against the near-infrared laser dye hexamethylindotricarbocyanine (HITC) as a reference of known quantum yield (0.28). (Duggan, J. X.; DiCesare, J.; Williams, J. F., Investigations on the use of laser dyes as quantum counters for obtaining corrected fluorescence spectra in the near infrared. In *New Directions in Molecular Luminescence*, Eastwood, D., Ed. American Society for Testing and Materials: ASTM STP 822, 1983; pp 112-126). The measured free ICG QE in high ionic strength, pH 7.4 PBS (0.028±0.001) is likely a result of significant dimerization, consistent with similar reports on aggregate formation. (Philip, R.; Penzkofer, A.; Baumler, W.; Szeimies, R. M.; Abels, C. *Journal of Photochemistry and Photobiology A: Chemistry* 1996, 96, 137-148). Physically-bound ground state dimers and oligomers act as quenching centers of fluorescence due to the energy transfer between excited and non-excited states. (Penzkofer, A.; Lu, Y. *Chemical Physics* 1986, 107, (2-3), 175-184). Thus, the reduced QE in PBS of the free dye indicates an increase in non-radiative decay rates among aggregates.

However, the QE of the doped CPNPs in PBS is 2-fold greater (0.049±0.003), with the CP matrix preventing environmental effects and dimerization. Furthermore, this result presents an objective explanation for the increased brightness from the ICG-CPNPs relative to the free fluorophore. Thus, CPNPs doped with ICG exhibit intrinsically greater brightness and enhanced QE relative to the free dye for in vivo and in vitro applications.

Example 15

Solvent Protection

Figure 17:
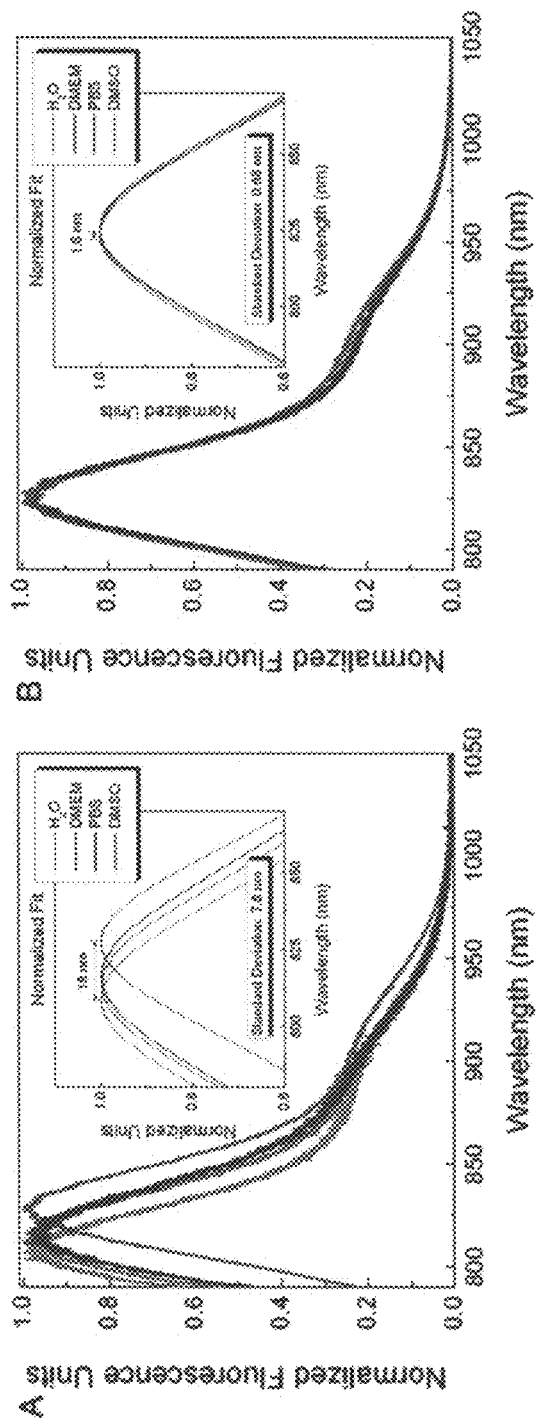
FIG. 17 shows the comparative spectral effect of four biorelevant solvents on the emission response of (A) free ICG dye and (B) dye-doped ICG-CPNPs. The normalized peaks spread across 18 nm for the free fluorophore (standard deviation of 7.8 nm), while encapsulation in CPNPs has an order of magnitude smaller 1.6 nm spread (0.68 nm standard deviation). This data confirms the largely impermeable nature of the CP matrix to the surrounding environment, shielding the encapsulated dye from solvent interaction.

The chemical stability of the encapsulated fluorophore was experimentally verified by analyzing fluorescence spectra as a function of solvent environment. The effect of four bio-relevant solvents (water, Dulbecco's modified Eagle's medium (DMEM), ethylene glycol, and dimethylsulfoxide (DMSO)) on the free ICG dye is shown in FIG. 17A, with shifts in the normalized emission spectra dependent on the solvent environment. The maximum emission wavelengths have a standard deviation of 7.8 nm over an 18 nm spread. These peak values shift toward longer wavelengths due to a combination of general solvent influences and specific solvent effects, such as molecule-molecule interactions and hydrogen bonding. (Lakowicz, J. R., *Principles of Fluorescence Spectroscopy*. 3rd ed.; Springer: Baltimore, Md., 2006).

In contrast, the emission spectra for the encapsulated dye in CPNPs are stable regardless of solvent environment. FIG. 17B (peak standard deviation of 0.68 nm, 1.6 nm spread) highlights the impermeable nature of the CP matrix to the solvent environment, which shields the dopant fluorophore from solvent interactions and prevents oxidative and solvent-induced alterations.

Example 16

Photostability

Figure 18:
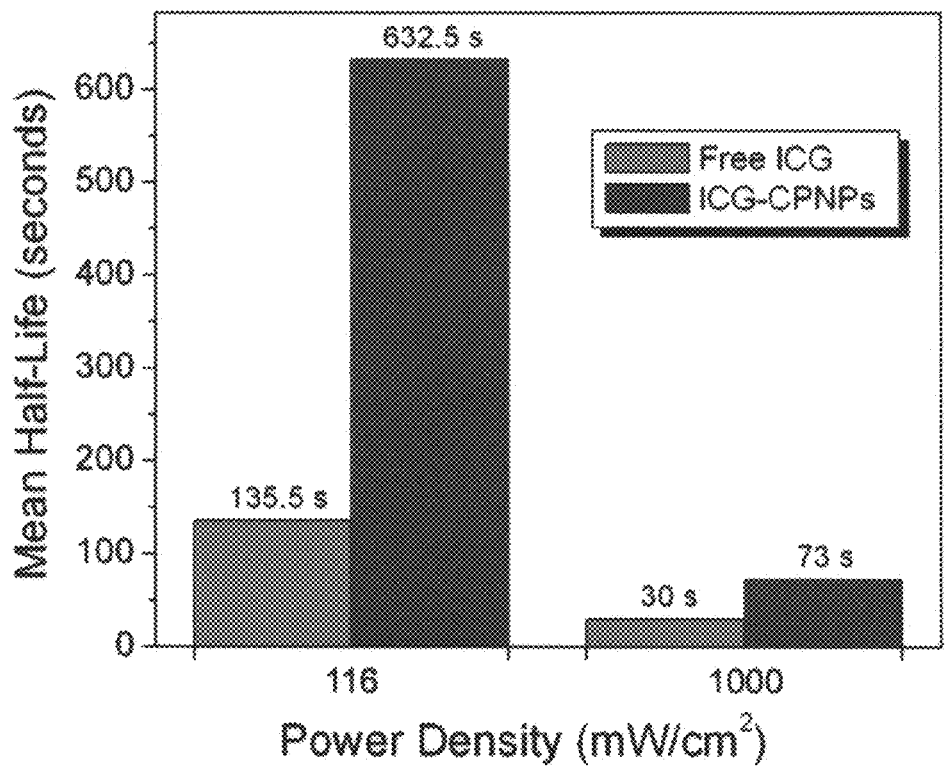
FIG. 18 shows the fluorescent half-life for a free ICG fluorophore (red) and ICG-CPNP (blue) suspension of matching absorption ($10^{-6}$ M) in PBS under 785 nm excitation at two power densities. Encapsulation provides an average of 470 percent increase in half-life at an excitation power commonly used in clinical settings (~100 mW/cm$^2$), and a 240 percent increase under even extremely high laser power density (1000 mW/cm$^2$). The free ICG fluorophore (red) is shown in the bar positioned to the left of the ICG-CPNP (blue) suspension.

Photobleaching is often a consequence of chemical and solvent interactions and is typically credited to a reaction between the fluorophore molecule and dissolved oxygen. (Soper, S. A.; Mattingly, Q. L. *Journal of the American Ceramic Society* 1994, 116, 3744-3752). The encapsulated ICG molecules are protected from environmental oxygen in the CPNP fluoroprobe system, as evidenced by a notable increase in the half-life of the encapsulated dye versus the free dye when subjected to continuous illumination (FIG. 18). The CPNP has a matrix shielding effect, which permits prolonged periods of excitation without significant degradation in emission intensity. Free ICG dye and doped CPNPs were excited under continuous illumination from a diode laser (785 nm; 450 mW/cm$^2$) at comparable concentrations in phosphate buffered saline (PBS, pH 7.4) to mimic the physiological environment. Data in FIG. 18 shows that CPNP encapsulation gives approximately a 500 percent increase in emission half-life at laser power slightly higher than typical clinical NIR imaging applications (5 to 50 mW/cm$^2$) De Grand, A. M.; Frangioni, J. V. *Technology in Cancer Research & Treatment* 2003, 2, (6), 553-562), and even provides a 240 percent increase under extremely high laser power conditions (1000 mW/cm$^2$).

Example 17

In Vivo Pharmacokinetic Distribution and Tumor Localization in Nude Mice

Figure 19:
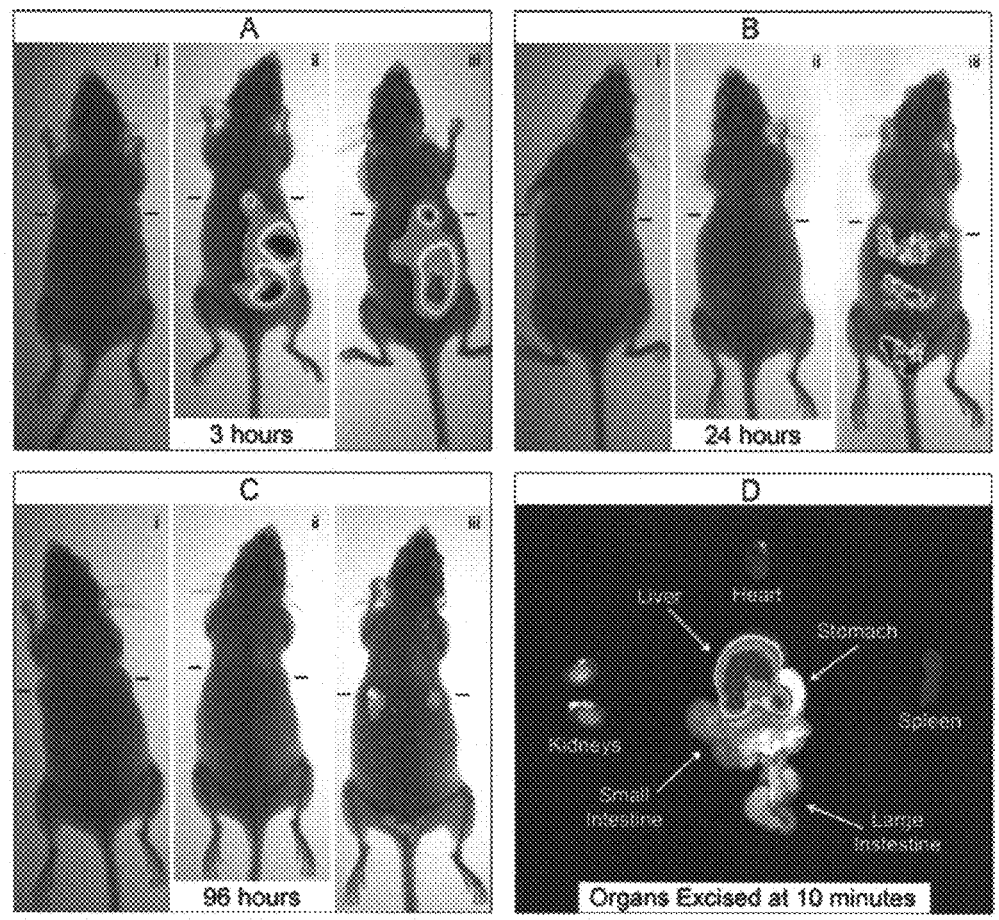
FIG. 19 shows NIR transillumination images (Ex. 755 nm, Em. 830 nm) taken at various times track fluorescence signals and pharmacokinetic distributions for the ICG-CPNPs and controls delivered systemically via tail vein injections in nude mice implanted with subcutaneous human breast adenocarcinoma tumors. Hash marks next to each mouse indicate the position of the 5 mm tumors. Two control samples (i) carboxylate-terminated CPNPs without ICG encapsulant and (ii) free ICG, match the particle concentration and fluorophore content ($10^{13}$ particles/mL and $10^{-5}$ M, respectively) of a (iii) PEGylated ICG-CPNP sample. (Bii) No fluorescence signal is detected from the free ICG at 24 hours post injection while the PEG-ICG-CPNP sample (Ciii) retains significant signal even after 96 hours. (Biii) The fluorescence signal is unmistakably localized in tumors 24 hours after administration with PEGylated ICG-CPNPs. The excised organs in panel (D) illustrate the biliary clearance route 10 minutes post-injection of PEG-ICG-CPNPs. Fluorescence signal is not seen from the stomach or spleen with minimal renal involvement.

A NIR whole animal imaging approach was used to investigate the in vivo pharmacokinetic distribution of ICG-CP-NPs in nude mice. FIG. 19 gives the fluorescence signal and intensity distribution as a function of time for ICG-CPNPs delivered systemically via tail vein injections. Two different surface functionalities of CPNPs were evaluated, as-synthesized carboxylate surface termination (not shown) and particles surface functionalized with polyethylene glycol (PEG) (series iii). The in vivo behavior of the ICG-CPNP samples were compared to two controls: a sample of carboxylated ghost CPNPs without a fluorescent encapsulate (series i) and free ICG of equivalent absorption (series ii). The fluorescence signals from the ICG-encapsulating CPNPs are significantly prolonged in vivo compared to the free fluorophore; no detectable signal was recorded from the free ICG at 24 hours after injection (FIG. 19B). In contrast, the ICG-CPNPs retained significant fluorescence signals even after 4 days (FIG. 19C). The relatively short in vivo fluorescence of the free dye is attributed to fluorescence quenching of free ICG in physiological environments (Landsman, M. L. J.; Kwant, G.; Mook, G. A.; Zijlstra, W. G. *Journal of Applied Physiology* 1976, 40, (4), 575-583; Desmettre, T.; Devoisselle, J. M.; Mordon, S. *Survey of Opthalmology* 2000, 45, (1), 15-27; Simmons, R.; Shephard, R. J. *Journal of Applied Physiology* 1971, 30, (4), 502-507; Gathje, J.; Steuer, R. R.; Nicholes, K. R. K. *Journal of Applied Physiology* 1970, 29, (2), 181-185; Mordon, S.; Devoisselle, J. M.; Soulie-Begu, S.; Desmettre, T. *Microvascular Research* 1998, 55, (2), 146-152; Maarek, J. M. I.; Holschneider, D. P.; Harimoto, J. *Journal of Photochemistry and Photobiology B-Biology* 2001, 65, (2-3), 157-164) with rapid aggregation and clearance from the body. (Desmettre, T.; Devoisselle, J. M.; Mordon, S. *Survey of Opthalmology* 2000, 45, (1), 15-27; Mordon, S.; Devoisselle, J. M.; Soulie-Begu, S.; Desmettre, T. *Microvascular Research* 1998, 55, (2), 146-152). The lipophilic character of ICG means it is taken up exclusively by hepatic parenchymal cells where it is then secreted into the bile. (Desmettre, T.; Devoisselle, J. M.; Mordon, S. *Survey of Opthalmology* 2000, 45, (1), 15-27). This clearance pathway is consistent with our observations of initial hepatic localization and eventual total clearance through the biliary tree with minimal acute renal involvement. FIG. 19D illustrates excised organs 10 minutes after systemic injection of PEGylated ICG-CPNPs. Additional dissections at longer time points affirmed this hepato-biliary clearance route with detectable signals along the gastrointestinal route. Negligible movement of fluorescence across the blood-brain barrier was observed. The hepatobiliary clearance mechanism offers yet another unique advantage of the calcium phosphate nanoparticles. The lack of long term accumulation within the liver, as well as minor renal imaging, suggests minimal potential for hepatic or renal toxicology. Moreover, the lack of brain imaging suggests that barriers, such as the blood brain barrier, are relatively impermeable to the carboxylate- or PEG-CPNPs.

Consistent with the ex situ analyses presented above, the matrix shielding effect provided by the CPNPs retards deleterious emission loss in circulation, permitting greater fluorescence emission and extended circulation times for the encapsulated dye. A comparison of signal intensity localized within the liver and along the hepato-gastrointestinal tract at the 3 hour time point (FIG. 19A) shows a lower concentration of ICG-CPNPs undergoing hepatic uptake and bile secretion relative to the free dye control, further confirming that a greater concentration of ICG-CPNP remains in circulation than free dye.

Our preliminary in vivo imaging study also underscores an additional advantage from the prolonged circulation afforded by the CPNPs. The longer retention times permit the particles to passively collect in the breast cancer tumors. Macromolecules and small particles with sufficient circulation times will eventually extravasate and accumulate in solid tumors (Kong, G.; Braun, R. D.; Dewhirst, M. W. *Cancer Research* 2000, 60, (16), 4440-4445) via a passive mechanism referred to as the enhanced permeability and retention (EPR) effect. (Maeda, H. *Advan. Enzyme Regul.* 2001, 41, 189-207; Maeda, H.; Fang, J.; Inutsuka, T.; Kitamoto, Y. *International Immunopharmacology* 2003, 3, 319-328). EPR has been attributed to the leaky nature of tumor blood vessels, which contain large interendothelial junctions, an imperfect basement membrane, an inefficient lymphatic system, and large numbers of transendothelial channels. (Dvorak, H. F.; Nagy, J. A.; Dvorak, J. T.; Dvorak, A. M. *Americal Journal of Pathology* 1988, 133, (1), 95-109). FIG. 19B shows that the PEGylated ICG-CPNPs accumulate in the two subcutaneous tumors within 24 hours after injection, which is consistent with previously reported EPR tumor accumulation periods for PEGylated gold nanoshell particles. (James, W. D.; Hirsch, L. R.; West, J. L.; O'Neal, P. D.; Payne, J. D. *Journal of Radioanalytical and Nuclear Chemistry* 2007, 271, (2), 455-459). The carboxylate functionalized CPNPs also showed distinct tumor localization (data not shown), but at significantly lower signal intensities than the PEGylated particles. The PEGylation provides physiological dispersion and inhibits protein absorption, providing maximum retention in the circulatory system to exploit the EPR effect. The in vivo imaging studies were replicated in 5 separate groups of mice.

These initial data provide strong evidence that CPNP-encapsulation of ICG is sufficient for in vivo shielding to provide prolonged fluorescence emission over 4 days post systemic injection. Furthermore, our preliminary animal imaging shows that PEGylated CPNPs have sustained in vivo circulation that provides the tumor retention that is crucial for diagnostic imaging applications.

Example 18

Tissue Imaging

Figure 20:
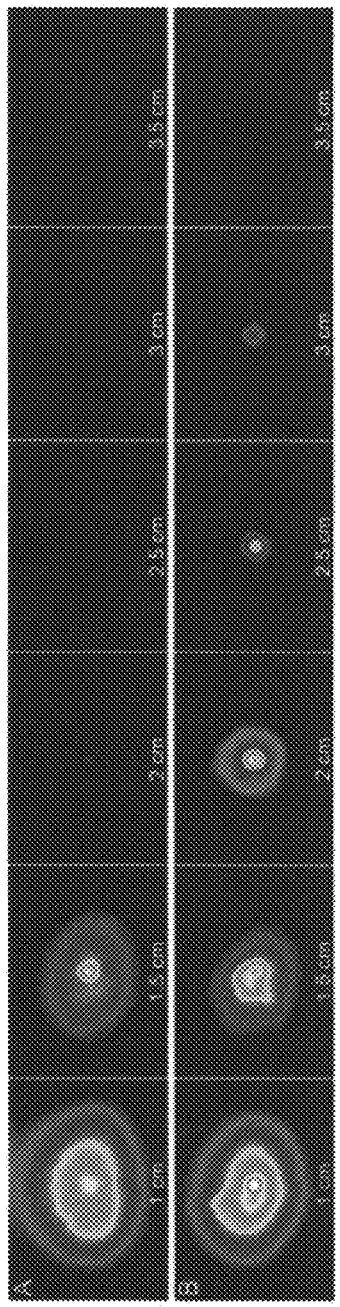
FIG. 20 shows the fluorescence signal intensity as a function of depth in dense porcine muscle tissue of (A) free ICG and (B) ICG-CPNPs of comparable absorbance ($10^{-4}$ M). A 15 mW laser diode (785 nm) and modified consumer-grade digital camera fitted with an 850 nm bandpass filter set was used for excitation and detection, respectively. Detectable penetration depths are extended to 3 cm with CPNP encapsulation compared to the free fluorophore (2 cm) under identical imaging parameters (F3.5, 7 s exposure).

Fluorescence signals through ex situ tissue were imaged under non-optimal conditions to demonstrate the deep tissue imaging capacity of the ICG-CPNPs. FIG. 20 presents the pseudocolored NIR intensities as a function of depth into porcine muscle tissue of free ICG and a sample of ICG-CPNPs of comparable absorbance ($10^{-4}$ M), both of which were front-face illuminated with excitation at 785 nm and recorded under identical imaging conditions using an 850 nm bandpass filter set on a modified NIR commercial CCD camera. Detectable penetration and emission depths are seen with ICG-CPNPs to 3 cm compared to the weakly fluorescent free fluorophore at only 2 cm. The signal intensity from the ICG-CPNPs also highlights the optically transparent nature of the CPNP carriers to the emission wavelength, an essential criterion for sensitive tissue imaging applications. The denser muscle tissue has a total optical attenuation coefficient of $\mu_t$=541 cm$^{-1}$ at 515 nm wavelength (Cheong, W. F.; Prahl, S. A.; Welch, A. J. *Quantum Electronics, IEEE Journal of* 1990, 26, (12), 2166-2185). Tissue of lower optical density, such as breast and epithelial tissues with $\mu_t$=189 cm$^{-1}$ and 243 cm$^{-1}$ at 633 nm, respectively (Cheong, W. F.; Prahl, S. A.; Welch, A. J. *Quantum Electronics, IEEE Journal of* 1990, 26, (12), 2166-2185), permit even greater detectable signal depths. Furthermore, our use of a commercial laser diode for excitation and an inexpensive commercial CCD camera for NIR imaging emphasizes the potential for ICG-CPNP imaging applications where portability and ease of operation, such as in the surgical operating theatre, are critical requirements.

Example 19

Conclusions

The optical, biophysical and chemical properties of the PEGylated ICG-CPNPs are well suited even for early stage in vivo tumor imaging. Bioresorbable calcium phosphate was used to encapsulate the near-infrared emitting fluorophore indocyanine green (ICG) as a new nanoparticulate-fluoroprobe for sensitive diagnostic imaging. Suspensions of ICG-CPNPs consist of 20 nm mean diameter particles with a carboxylate or PEG surface termination that provides electrosteric dispersion in physiological conditions. The nanoparticle-based system readily satisfies the critical size for efficient in vivo cellular uptake (<50 nm) and the colloidal criteria of robust dispersion in physiological conditions for successful use as an exogenous probe in long-term bioimaging applications. Furthermore, the ICG-encapsulating CPNPs had significantly better optical properties compared to the free fluorophore. The maximum fluorescence peak is not affected by encapsulation and exhibited higher emission intensity relative to the free fluorophore at elevated concentrations. The CP matrix is impermeable to the surrounding solvent, effectively sequestering the ICG from environmental influence. The dye-doped CPNPs have a 4.7-fold longer fluorescent half-life at clinical imaging excitation power ranges and a 2-fold increase in quantum efficiency in PBS (0.049±0.003). These properties provide increased brightness and prolonged signal intensity vital for sensitive diagnostic applications. Furthermore, the PEGylated CPNP encapsulation also provide prolonged circulation times in vivo with passive tumor accumulation of the nanoparticles seen by 24 hours after systemic administration that persisted more than 96 hours post-injection. Finally, preliminary deep tissue imaging verified the capacity of these NIR CPNPs for deep tissue imaging applications, revealing extended signal detection depths of at least 3 cm compared to the free fluorophore. Combined with the established biocompatibility and facile resorbability of calcium phosphates, the physical and optical properties of ICG encapsulating CPNPs represent an attractive new fluoroprobe for sensitive diagnostic imaging applications.

Example 20

Materials

All chemicals used in this work were purchased as described: calcium chloride dehydrate (99+%, A.C.S. Reagent), sodium hydrogen phosphate (99+%, A.C.S. Reagent), disodium citrate dehydrate (99+%, A.C.S. Reagent), sodium silicate solution (~14% NaOH, ~27% SiO$_2$), ethyl-N-(3-dimethylaminopropyl)-N' hydrochloride carbodiimide (Fluka BioChemika ≤99.0% AT), dimethylsulfoxide (≤99.9%, A.C.S. Reagent), Dulbecco's Modified Eagle's Medium, and ethylene glycol (99.8%, Anhydrous) from Sigma Aldrich (St Louis, Mo.); indocyanine green from TCI America (Portland, Oreg.); cyclohexane (99.9+%, A.C.S. Reagent), and methanol (99.9+%, OnmiSolv spectroscopic grade) from VWR International (West Chester, Pa.); Igepal® CO-520 from Rhodia Inc. (Cranbury, N.J.); ethyl alcohol (200-proof, Absolute, ACS/USP Grade) from Pharmco-AAPER (Brookfield, Conn.); methoxypolyethylene glycol amine (mPEG-amine, MW 20 kDa) from JenKem Technology USA (Allen, Tex.); 1,1',3,3,3',3'-hexamethylindotricarbocyanine iodide from Exciton (Dayton, Ohio); fetal bovine serum (35-010-CV, Regular) from Mediatech, Inc. (Manassas, Va.); Trypsin (soybean) from Invitrogen (Carlsbad, Calif.).

All HLPC solutions were prepared with $CO_2$-free deionized water (pH 7). Water was deionized in our lab using a Millipore Milli-Q purification system (Billerica, Mass.), passed through a 200 nm filter, and boiled while flushing with argon to remove $CO_2$. All pH measurements were performed using a Sentron ISFET pH probe (Argus IP 65 ISFET, Sentron Inc., The Netherlands) calibrated against aqueous standards.

Example 21

Synthesis and Characterization of NIR Dye-Doped CPNPs

Dye-doped calcium phosphate nanoparticles (CPNPs) were synthesized employing a double reverse microemulsion approach with the basic procedure described in detail elsewhere. (Nano Lett., 2008, 8 (12), pp 4108-4115.; Nano Lett., 2008, 8 (12), pp 4116-4121; ACS Nano, 2008, 2 (10), pp 2075-2084.). The two reverse microemulsions were formed by a cyclohexane/nonylphenoxyl (glycolether) (Igepal CO-520)/water system; 650 μL of $10^{-2}$ M $CaCl_2$ was added to 14 mL of a 29 volume percent solution of Igepal CO-520 in cyclohexane (Microemulsion A), while 65 μL each of $6\times10^{-3}$M disodium phosphate and $8.3\times10^{-3}$ M disodium silicate was added to a separate 14 mL of a 29 volume percent Igepal CO-520/cyclohexane mixture (Microemulsion B). The dopant fluorophore (520 μL of $3\times10^{-3}$M ICG) was added to Microemulsion B based on charge considerations to preclude coprecipitation inhibition that can occur once calcium binds to the sulfonate-groups present on the fluorophore molecule. All solutions were in $CO_2$-free deionized water (pH 7) unless otherwise noted. The microemulsions were equilibrated under constant stirring for 5 minutes before being combined to form a microemulsion mixture (Microemulsion C) which served as a microreactor for the coprecipitation of the ICG-doped CPNPs. Microemulsion C was stirred for 2 minutes before the dispersant, 225 μL of $10^{-3}$ M sodium citrate, was added and stirred for an additional 10 minutes. Finally, the micelles were disrupted with 50 mL of pH 7 ethanol before laundering via a van der Waals HPLC procedure. (Nano Lett., 2008, 8 (12), pp 4108-4115.; Nano Lett., 2008, 8 (12), pp 4116-4121; ACS Nano, 2008, 2 (10), pp 2075-2084). The ethanol was adjusted to pH 7 with small additions of 1 M aqueous KOH.

The particles were washed by first loading the sample solution onto a chromatography column containing silica microspheres (Stellar Phases Inc., ~20 μm diameter, 60 Å pores). The system was then flushed with pH adjusted ethanol (pH 7) and monitored at the characteristic absorption wavelength of ICG (785 nm) using a UV-Vis absorption detector (Shimadzu SPD-6A; Shimadzu Scientific, Kyoto, Japan). This washing step was concluded only when the detector reached baseline, indicating the removal of residual free dye. The nanoparticles, which remained bound on the column, were then eluted with a 7:3 ethanol:water solution prepared with $CO_2$-free deionized water and adjusted to pH 7 (using 1 M KOH). The first major peak, corresponding to the elution of the doped particles, was collected.

The size, morphology and state of dispersion of the nanoparticles were characterized using a Philips 420 TEM on carbon support film on a 300-mesh copper specimen grid (#CF300CU; Electron Microscopy Sciences, Hatfield, Pa.). Each TEM specimen was prepared by dropping as-prepared CPNP in 70:30 ethanol:water on the TEM grid. Imaging was conducted at 120 keV with current densities below 70 pA/cm$^2$ to avoid beam damage to the organic-inorganic composite nanoparticles.

Example 22

Attachment of PEGamine to Carboxylic Acid Functionalized CPNPs

The as-synthesized particles with carboxylate functional groups were surface passivated with polyethylene glycol (PEG) via a secondary functionalization scheme. A 4 mL aliquot of the carboxylate-CPNPs ($5\times10^{13}$ particles) were chemically conjugated with methoxypolyethylene glycol amine (mPEG-amine) through an ethyl-N-(3-dimethylaminopropyl)-N' hydrochloride carbodiimide (EDAC) reaction. (Sharma, R. K.; Das, S.; Maitra, A. *Journal of Colloid and Interface Science* 2004, 277, (2), 342-346). The sample was first stirred at 550 rpm on a combination magnetic stir/hot plate set to 50° C. In a drop wise manner, 1 mL of EDAC (1 mg/mL) followed by 1 mL of mPEG-amine (10 mg/mL), both in aqueous solutions of $CO_2$-free DI water (pH 7), were added to the sample under continuous stirring, amounting to a calculated 6-fold excess for monolayer surface coverage. The particles were reacted for 15 hours at 50° C. to form amide linkages between the carboxylate surfaces and the mPEG-amine. The mixture was then filtered through a centrifuge filter (Microsep 100K Omega; Pall Life Science, East Hills, N.Y.) at 1000 g for 40 minutes (Marathon 22K Centrifuge; Fischer Scientific, Pittsburgh, Pa.) to remove any excess EDAC and unreacted mPEG-amine. TEM characterization of the retentate showed that the PEG-CPNPs remained well dispersed after the centrifugation wash.

Example 23

Optical Characterization of ICG-CPNPs

For all optical measurements, samples were placed in a low-volume fluorescence cuvette (9F-SOG-10-GL14-S; Starna Cells, Inc., Atascadero, Calif.), and held by a modified cuvette holder. Absorption spectra were recorded on a Perkin-Elmer Lambda 950 UV-Vis-NIR spectrophotometer (Perkin Elmer, Waltham, Mass.). The dye-doped particle absorption at 785 nm was compared to a standard curve of absorption vs. ICG concentration to identify the apparent encapsulate content, not accounting for any matrix effects. Next, the release of the encapsulated fluorophore was induced with the addition of a 10:1 volume ratio of a $10^{-3}$ M solution of ethylenediaminetetraacetic acid (EDTA) to the particle suspension. EDTA is a chelating agent that sequesters the divalent $Ca^{2+}$ ion from the nanostructure, dissolving the calcium phosphate particles. The 785 nm absorption value of the released ICG was compared to a second standard curve in an EDTA-salt solution, isotonic to the solvent environment after nanoparticle dissolution. This procedure gave the true fluorophore concentration encapsulated within the particles.

Fluorescence spectra were recorded using an in-house spectroscopy system in which emitted radiation was collected at 90 degrees with a 10× microscope objective (N.A. 0.3) coupled into a fiber optic cable leading to the spectrometer (Ocean Optics HR-2000-USB). A high power 785 nm diode laser (450 mW/cm$^2$) was used as the excitation source (RL785; Renishaw plc, Gloucestershire, UK). Solvent influence was recorded on both free ICG and doped nanoparticle suspensions of comparable fluorophore content. Aliquots of each were diluted 1:10 into the test solvent and kept in the dark. Measurements were conducted precisely 10 minutes after the sample introduction.

Quantum efficiency measurements were conducted following the comparative method of Williams et al. (Williams, A. T. R.; Winfield, S. A.; Miller, J. N. *Analyst* 1983, 108, 1067-1071), for which a reference sample with identical absorbance at the same excitation wavelength of the unknown analyte is assumed to absorb the same number photons as the latter. Hence, the ratio of the integrated fluorescence intensities of the test solution to the reference of known efficiency yields the ratio of the quantum efficiency values, provided they are recorded under identical conditions. (Russin, J. T.; Altinoğlu, E. İ.; Adair, J. H.; Eklund, P. C. to be submitted). Hexamethylindotricarbocyanine (HITC) was selected as the standard fluorophore due to its similar absorption at the excitation wavelength of ICG; its quantum yield is well documented at 0.28 in methanol. (Duggan, J. X.; DiCesare, J.; Williams, J. F., Investigations on the use of laser dyes as quantum counters for obtaining corrected fluorescence spectra in the near infrared. In *New Directions in Molecular Luminescence*, Eastwood, D., Ed. American Society for Testing and Materials: ASTM STP 822, 1983; pp 112-126). Each measurement was conducted in duplicate on two separate occasions using freshly prepared stock solutions and a new set of standard data. This comparative quantum efficiency determination was developed for molecular systems, and as such, does not take into account scattering influences characteristic of particulate suspensions. However, the measured values are presented as a conservative approximation of quantum efficiency for the encapsulated fluorophore, as we expect adjustments for the attenuated light that actually reaches the encapsulated molecules within the highly scattering particle geometry would show a larger fluorescent ratio and thus yield higher efficiency values than reported.

The decay of the fluorescence with time for ICG was generated by recording the fluorescent spectra of both the free dye solution and doped nanoparticle suspension of equivalent fluorophore concentration at five second intervals under continuous illumination of the 785 nm laser. A set of measurements for each sample was conducted both at full laser power (100 mW) and at a reduced 11.6 mW power using an absorptive neutral density filter of +1.0 optical density (NE 10A; Thor Labs, Newton, N.J.). A 120 µL volume of each analyte was used to ensure simultaneous illumination over the entire analyte volume. Free ICG samples were diluted from the same $10^{-3}$ M stock solution. Measurements were recorded in duplicate using fresh solutions for each run.

Example 24

In Vivo Animal Studies

Four-week-old female nude mice (approximate weight of 15 grams) were purchased from Harlan (Indianapolis, Ind.). All animal manipulations were performed with sterile technique and were approved by the Pennsylvania State University Institutional Animal Care and Use Committee.

Human breast adenocarcinoma cells (MDA-MB-231; American Type Culture Collection; Manassas, Va.) were cultured in DMEM supplemented with 10% FBS. Exponentially growing cells were removed from the plate by trypsin/EDTA detachment, re-suspended in PBS, and injected subcutaneously into both the right and left flank of the nude mice at approximately $10^6$ cells per mouse. Tumors were allowed to grow to ~5 mm in diameter before the imaging trial was commenced.

Four different samples were prepared: ICG-CPNPs, both carboxylate terminated and PEGylated, a carboxylate terminated blank CPNP suspension, and a $10^{-4}$ M solution of free ICG in deionized $H_2O$ (pH 7). The latter two controls were designed to roughly match the estimated concentration of CPNPs ($10^{13}$ particles/mL) and ICG content ($10^{-5}$M) in the injected solutions, respectively.

ICG-CPNP aliquots for systemic injection were prepared in a 1 to 10 volume dilution in PBS. A 200 µL aliquot of each was injected into the tail vein of four of the nude mice. Near-infrared transillumination images were recorded using an In Vivo FX whole animal imaging station (Kodak; Rochester, N.Y.). The animals were placed into the imaging chamber, and anesthesia was induced and maintained by inhalation of 5% IsoSol (isoflurane) vapor (Vedco, St. Joseph, Mo.) in 100% oxygen.

Each mouse was positioned flat on its abdomen side-by-side for simultaneous imaging. A 3 minute exposure was recorded under NIR excitation using a 755 and 830 nm bandpass excitation and emission filter set, respectively. Next, an X-Ray image (1 second exposure) was recorded of the mice in the same position to be used as an underlying reference. The separate NIR fluorescence and X-Ray images were then merged to illustrate signal distribution relative to anatomy. This anesthesia and imaging procedure was repeated for each time point over a period of 96 hours. The NIR images were pseudocolored and merged with the underlying X-Ray images using Kodak MI imaging software (v.4; Kodak; Rochester, N.Y.). The imaging studies were conducted on 20 mice for a total of 5 separate study groups.

Example 25

Ex Situ Tissue Imaging

Fluorescence signal intensity as a function of tissue depth was imaged for both free and encapsulated ICG of matching absorbance ($10^{-4}$ M bulk ICG content) using a basic Sony DSC-P200 point-and-shoot camera (F3.5, 7 second exposure). The camera was modified to record wavelengths in the NIR by replacing the stock internal ICG/AA optics (LPC, LLD). The 100 µL aliquots were held in a 25 mm section of Tygon tubing (1 mm inner diameter) and front-face illuminated with a 780 nm 15 mW low divergence laser diode (LDM-5; Laserex Tech) fixed at 20° to the image plane. The camera was fitted with two 850 nm bandpass filters (FB850-40; Thor Labs) and positioned 20 cm from the tissue surface to capture the images. Kodak MI imaging software (v.4; Kodak) was used to pseudocolor the NIR image files and remove background noise. Porcine muscle tissue was purchased from a local butcher.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

What is claimed is:

1. A method of treating tumors or imaging targeted tissue in a subject, comprising:
   administering to the subject in need thereof an effective amount of a photosensitizer (PS) encapsulated in a calcium phosphate nanoparticle (CPNP); and
   exposing the tumor or tissue of the subject to a photoactivating amount of light at a wavelength that activates the PS for a sufficient amount of time to obtain a desired response.

2. The method of claim 1 wherein the PS is a near-infrared PS.

3. The method of claim 1 wherein the photosensitizer comprises indocyanine green, Cy3 Amidite, Cascade Blue©, 10-(3-Sulfopropyl)acridinium betaine (SAB), a fluorescein sodium salt, rhodamine WT, a coumarin or a porphyrin.

4. The method of claim 1 wherein the nanoparticle comprises on its surface a carboxylate, PEG, or amine functional group.

5. The method of claim 1 wherein the nanoparticle comprises on its surface a targeting moiety.

6. The method of claim 5 wherein the targeting moiety comprises a ligand or an antibody.

7. The method according to claim 1 wherein the nanoencapsulated near-infrared photosensitizer is administered topically, intravenously, orally, locally, subcutaneously, intramuscularly, or intraperitoneally.

8. The method according to claim 1 wherein the PS accumulates in the tumor.

9. The method according to claim 1 wherein the subject is a mammal.

10. The method according to claim 1 wherein the subject is a human.

11. The method according to claim 1 wherein the desired response is inhibition of tumor growth.

12. The method according to claim 1 wherein the desired response is a protective response against tumor challenge in the subject.

13. The method according to claim 1 wherein the desired response is eradication of distant tumors or metastasized tumors not directly targeted with the photosensitizer (PS) encapsulated in the CPNP.

14. The method according to claim 1 wherein the tumor is a solid tumor.

15. The method according to claim 1 wherein the subject is suffering from leukemia or a lymphoma.

16. The method according to claim 1 wherein the desired response is the production of an increased amount of reactive oxygen species by the nano-encapsulated PS as compared to an amount of reactive oxygen species produced by a control wherein the PS is not nano-encapsulated.

17. The method according to claim 1 wherein the desired response is the production of an increased amount of endogenous pro-apoptotic lipids by the nano-encapsulated PS as compared to an amount of endogenous pro-apoptotic produced by a control wherein the photosensitizer is not nano-encapsulated.

18. The method according to claim 17 wherein the endogenous pro-apoptotic lipids comprise ceramide, dihydroceramide or combinations thereof.

19. The method according to claim 1 wherein the radiation comprises light, ultrasound, magnetic force, electromagnetic radiation in the ultra violet or visible electromagnetic spectrum or near infrared.

20. The method according to claim 1 further comprising imaging the tumor or target tissue using an effective amount of the encapsulated PS to obtain imaging data of the tumor or target tissue.

21. The method according to claim 20 further comprising analyzing the imaging data to quantify a dosing schedule for the PS encapsulated in the CPNP photodynamic treatment of the tumor.

22. The method according to claim 20 comprising imaging the target tissue or tumor prior to, concomitant with, or subsequent to treating the tumor or tissue with the encapsulated PS.

23. The method according to claim 20 further comprising imaging deep target tissue or tumor cells.

24. The method according to claim 23 further comprising imaging deep target tissue or tumor cells at a depth of about 3 cm to about 10 cm.

25. The method according to claim 1 wherein the CPNP further comprises an agent for the treatment of cancer.

26. The method according to claim 1 wherein the PS is used to image vessels to obtain data for determining atherosclerosis, restenosis or graft disease.

* * * * *